United States Patent [19]

Nadzan et al.

[11] Patent Number: 5,128,346
[45] Date of Patent: Jul. 7, 1992

[54] DERIVATIVES OF D-GLUTAMIC ACID AND D-ASPARTIC ACID

[75] Inventors: Alex M. Nadzan, Libertyville; James F. Kerwin, Mundelein; Chun W. Lin, Wood Dale, all of Ill.

[73] Assignee: Abbott Laboratories, Abbott Park, Ill.

[21] Appl. No.: 571,945

[22] Filed: Aug. 23, 1990

Related U.S. Application Data

[60] Division of Ser. No. 234,525, Aug. 22, 1988, Pat. No. 4,971,978, which is a continuation-in-part of Ser. No. 99,866, Sep. 21, 1987, abandoned.

[51] Int. Cl.$^5$ .................. H01N 43/42; C07D 209/04
[52] U.S. Cl. ..................... 514/307; 514/309; 514/311; 514/314; 514/365; 514/374; 514/376; 514/381; 514/382; 514/397; 514/406; 514/407; 514/414; 514/419; 546/307; 546/309; 546/311; 546/314; 548/181; 548/213; 548/215; 548/225; 548/243; 548/251; 548/252; 548/336; 548/374; 548/454; 548/455; 548/484; 548/491
[58] Field of Search ............. 548/491, 495, 374, 215, 548/181, 213, 214, 225, 236, 240, 243, 247, 251, 252, 336, 454, 455, 484; 546/147, 141, 169; 514/307, 311, 314, 365, 369, 372, 374, 376, 378, 380, 381, 397, 398, 399, 406, 407, 414, 418, 419

[56] References Cited

U.S. PATENT DOCUMENTS

| | | | |
|---|---|---|---|
| 4,568,489 | 2/1986 | Floyd | 548/492 |
| 4,634,716 | 1/1987 | Parsons et al. | 548/215 |
| 4,665,193 | 5/1987 | Ryono et al. | 548/492 |
| 4,668,797 | 5/1987 | Urbach et al. | 548/492 |
| 4,877,785 | 10/1989 | Hanson et al. | 548/215 |

Primary Examiner—C. Warren Ivy
Assistant Examiner—Raymond Covington
Attorney, Agent, or Firm—Richard A. Elder; Steven R. Crowley; Steven F. Weinstock

[57] ABSTRACT

A compound of the formula:

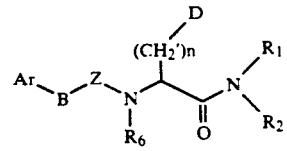

wherein $R_1$ and $R_2$ are substituents; $R_6$ is hydrogen, loweralkyl, cycloalkyl, loweralkenyl, arylalkyl, (substituted aryl)alkyl, or (heterocyclic)alkyl; B is a bond, an alkylene group, an alkenylene group, an alkadienylene group or a heteroatom containing linking group; D is a substituted acyl group or tetrazolyl; Z is CO, C(S) or S(O)$_2$; Ar is a heterocyclic group; and n is 1 to 3.

Also disclosed are a composition and a method for antagonizing CCK, a composition and method for treating or preventing gastrointestinal, central nervous, appetite regulating and pain regulating systems, a composition and method for treating or preventing hyperinsulinemia, methods of making the compounds and intermediates useful in making the compounds.

9 Claims, No Drawings

DERIVATIVES OF D-GLUTAMIC ACID AND D-ASPARTIC ACID

This is a division of application Ser. No. 07/234,525, filed Aug. 22, 1988 U.S. Pat. No. 4,971,998, which is a continuation-in-part of application Ser. No. 07/099,866, filed Sep. 21, 1987 abandoned.

TECHNICAL FIELD

This is a continuation-in-part of U.S. patent application Ser. No. 099,866, filed Sep. 21, 1987.

The present invention relates to novel organic compounds and compositions which antagonize cholecystokinin, processes for making such compounds, synthetic intermediates employed in these processes, a composition and a method for antagonizing CCK, and a composition and a method for treating gastrointestinal disorders, cancers of the gall bladder and pancreas, hyperinsulinemia, central nervous system disorders, or pain, or regulating appetite with such compounds.

BACKGROUND OF THE INVENTION

Cholecystokinins (CCK) are a family of amino acid polypeptide hormones. $CCK_{33}$, a 33 amino acid fragment of CCK was first isolated from hog intestine. (Matt and Jorpes, *Biochem. J.* 125 628 (1981)). Recently the $CCK_{33}$ fragment has been found in the brain, where it appears to be the precursor of two smaller fragments, an octapeptide $CCK_8$ and a tetrapeptide $CCK_4$. (Dockray, *Nature* 264 4022 (1979)).

$CCK_8$, the carboxyl terminal octapeptide fragment of CCK, is the most potent peptide in the CCK family and is the predominant form of CCK in the brain. (Larson and Rehfeld, *Brain Res.* 165 41 (1981)). The localization of CC fragments in the cortex of the brain suggests that CCK may be an important neuromodulator of memory, learning and control of primary sensory and motor functions. CCK and its fragments are believed to play an important role in appetite regulation and satiety. (Della-Fera, *Science* 206 471 (1979); Gibbs et al., *Nature* 289 599(1981); and Smith, *Eating and Its Disorders*, eds., Raven Press, New York, 67 (1984)).

CCK antagonists are useful in the treatment and prevention of CCK-related disorders of the gastrointestinal (GI), central nervous (CNS) and appetite regulatory systems of animals, especially man. CCK antagonists are also useful in potentiating and prolonging opiate induced analgesia and thus have utility in the treatment of pain. (Faris et al., *Science* 226 1215 (1984)).

Previously four distinct chemical classes of CCK receptor antagonists have been reported. The first class comprises derivatives of cyclic nucleotides as represented by dibutyryl cyclic GMP (N. Barlos et al., *Am. J. Physiol.*, 242, G 161 (1982) and references therein). The second class is represented by C terminal fragments of CCK (see Jensen et al. *Biochem. Biophys. Acta*, 757, 250 (1983) and Spanarkel J. Biol. Chem. 758, 6746 (1983)). The third class comprises amino acid derivatives of glutamic acid and tryptophan as indicated by proglumide and benzotript (see Hans et al. *Proc. Natl. Acad. Sci. U.S.A.*, 78, 6304 (1981) and Jensen et al. *Biochem. Biophys. Acta.* 761, 269 (1983)). The fourth and most recent class is comprised of 3-substituted benzodiazepines, represented by L-364,718 (see: Evans et al. *Proc. Natl. Acad. Sci. U.S.A.*, 83 4918 (1986)).

With the exception of the benzodiazepine based class, all of these compounds are relatively weak antagonists of CCK demonstrating $IC_{50}$ values between $10^{-4}$ and $10^{-6}$ M. The benzodiazepine CCK antagonists or their metabolites may have undesirable effects in vivo due to their interaction with benzodiazepine receptors.

The C-terminal pentapeptide fragment of CCK is the same as the C-terminal pentapeptide fragment of another polypeptide hormone, gastrin. Gastrin, like CCK, exists in both the GI and CNS systems. Gastrin antagonists are useful in the treatment and prevention of gastrin-related disorders of the GI system such as ulcers, Zollinger-Ellison syndrome and central G cell hyperplasia. There are no known effective receptor antagonists of the in vivo effects of gastrin. (Morely, *Gut Pept. Ulcer Proc.*, Hiroshima Symp. 2nd, 1, (1983)).

SUMMARY OF THE INVENTION

It has now been found that the compounds of the invention are antagonists of cholecystokinin (CCK) and bind specifically to CCK receptors. These CCK antagonists are useful in the treatment and prevention of CCK-related disorders of the gastrointestinal, central nervous and appetite regulatory systems of animals and humans. These compounds are useful in the treatment and prevention of gastrointestinal ulcers, cancers of the gall bladder and pancreas, pancreatitis, hyperinsulinemia, Zollinger-Ellison syndrome, central G cell hyperplasia, irritable bowel syndrome, the treatment or prevention of neuroleptic disorders, tardive dyskinesia, Parkinson's disease, psychosis, Gilles de la Tourette syndrome, disorders of appetite regulatory systems, the treatment of pain and the treatment of substance abuse.

DISCLOSURE OF THE INVENTION

In accordance with the present invention, there are cholecystokinin antagonists of the formula:

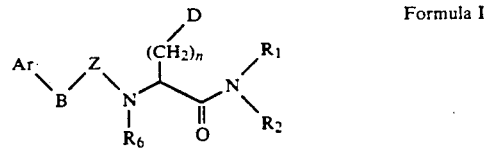

Formula I wherein
$R_1$ and $R_2$ are independently selected from
1) hydrogen,
2) $C_1$-$C_8$ loweralkyl,
3) cycloalkyl,
4) loweralkenyl,
5) —(CH$_2$)$_m$(C(O))$_r$cycloalkyl wherein m and r are not both 0,
6) —(CH$_2$)$_m$CN,
7) —(CH$_2$)$_m$OR$_9$ wherein R$_9$ is loweralkyl, aryl, substituted aryl wherein the aryl group is substituted with one, two or three substituents independently selected from loweralkyl, alkoxy, thioalkoxy, carboxy, carboalkoxy, nitro, trihalomethyl, hydroxy, amino, and NH(loweralkyl), arylalkyl or (substituted aryl)alkyl wherein substituted aryl is as defined above,
8) adamantyl,
9) —(CH$_2$)$_m$C(O))$_4$NR$_6$R$_7$ wherein R$_6$ and R$_7$ are independently selected from hydrogen, loweralkyl, cycloalkyl, loweralkenyl, —(CH$_2$)$_m$aryl, —(CH$_2$)$_m$(substituted aryl) wherein substituted aryl is as defined above, and —(CH$_2$)$_m$heterocyclic, 10) cyclic groups wherein $R_1$ and $R_2$ taken together with the adjacent nitrogen atom are morpholinyl, pyrrolidinyl, piperazinyl, piperidinyl or other substituted cyclic groups represented by

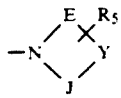

wherein E and J are independently selected from $(CH_2)_p$, $(CH=CH)_r$, $CH_2C(O)$, $C(O)CH_2$, $QCH_2$, $CH_2Q$, $C(O)Q$, and $QC(O)$ wherein Q is S, O, or $NR_{10}$ wherein $R_{10}$ is hydrogen,
—$(C(O))_r(C_1-C_8$loweralkyl),
—$(C(O))_r$cycloalkyl,
—$(C(O))_r$loweralkenyl,
—$(C(O))_r$loweralkynyl, thioalkoxy,
—$(C(O))_r(CH_2)_m$aryl,
—$(C(O))_r(CH_2)_m$(substituted aryl) wherein substituted aryl is as defined above, —$(CH_2)_m$carboxyl,
—$(CH_2)_s(C(O))_r$aryl,
—$(CH_2)_s(C(O))_r$(substituted aryl),
—$(CH_2)_m$carboalkoxy,
—$(CH_2)_m$carboxamide,
—$(CH_2)_m$carboaryloxy, —$C(X)_3$ wherein X is halogen, —$(C(O))_r(CH_2)_sR_{11}$ wherein $R_{11}$ is hydrogen, loweralkyl, loweralkenyl, cycloalkyl, —$(CH_2)_m$aryl, —$(CH_2)_m$substituted aryl) wherein substituted aryl is as defined above, —$(CH_2)_m$heterocyclic, nitro, halogen, —CN, —OH, —$NH_2$, —NHOH, —$NR_6R_7$ wherein $R_6$ and $R_7$ are as previously defined, —$NR_4OH$ wherein $R_4$ is hydrogen, —$(C(O))_r$loweralkyl, —$(C(O))_r$loweralkenyl, —$(C(O))_r$cycloalkyl, —$(C(O))_r$loweralkynyl, —$(C(O))_r(CH_2)_m$aryl, —$(C(O))_r(CH_2)_m$(substituted aryl)
wherein substituted aryl is as defined above, —$(CH_2)_mOR_4$ wherein $R_4$ is as defined above, or —$(CH_2)_mSR_4$ wherein $R_4$ is as defined above; Y is S, O, $CH_2$ or $NR_{10}$; and $R_5$ is one, two or three substituents independently selected from hydrogen,
—$(C(O))_r(C_1-C_8$loweralkyl),
—$(C(O))_r$cycloalkyl, decahydronaphthyl,
—$(C(O))_r$loweralkenyl,
—$(C(O))_r$loweralkynyl, thioalkoxy,
—$(C(O))_r(CH_2)_m$aryl,
—$(C(O))_r(CH_2)_m$substituted aryl) wherein substituted aryl is as defined above, —$(CH_2)_s(C(O))_r$aryl,
—$(CH_2)_s(C(O))_r$(substituted aryl) wherein substituted aryl is as defined above —$(CH_2)_m$carboxyl,
—$(CH_2)_m$carboalkoxy,
—$(CH_2)_m$carboxamide,
—$(CH_2)_m$carboaryloxy, —$C(X)_3$,
—CN, —OH, $NH_2$, NHOH, $NR_6R_7$ wherein $R_6$ and $R_7$ are as defined above, —$(CH_2)_mOR_4$, —$(CH_2)_mSR_4$ and —$NR_4OH$ wherein $R_4$ is as defined above;

11) —$(C(R_5)_2)_m$aryl wherein $R_5$ is as defined above with the proviso that not all $R_5$ substituents are hydrogen, 12) —$(C(R_5)_2)_m$(substituted aryl) wherein $R_5$ is defined as above with the proviso that not all $R_5$ substituents are hydrogen and wherein substituted aryl is as defined above, and 13) —$(C(R_5)_2)_mC(O)R_3$, wherein $R_5$ is as defined above and wherein $R_3$ is —OH, —$OR_4$ wherein $R_4$ is as defined above, —$NR_6R_7$ wherein R and $R_7$ are as defined above, —$NHR_4$ wherein $R_4$ is as defined above, or $NR_4OH$ wherein $R_4$ is as defined above;

B is
1) $(CH_2)_m$,
2) $(CR_5=CR_5)_g$ wherein $R_5$ is as defined above,
3) $LCH_2$ wherein L is O, S, or $NR_5$ wherein $R_5$ is as defined above,
4) $CH_2L$ wherein L is as defined above, or
5) $NR_5$ wherein $R_5$ is as defined above;

D is
1) —$C(O)R_3$ wherein $R_3$ is as defined above or
2)

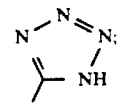

Z is
1) C(O),
2) C(S), or
3) $S(O)_2$;
Het is a heterocyclic group,
n is 1 to 3, m is 0 to 4, p is 0 to 2, r is 0 to 1 and s is 1 to 4; or pharmaceutically acceptable salts thereof.

The compounds of the invention wherein n=1–3, D is —$C(O)R_3$ wherein $R_3$ is OH or —$NR_6R_7$ wherein $R_6$ and $R_7$ are independently selected from hydrogen, loweralkyl, cycloalkyl, $C_{2-4}$ loweralkenyl, benzyl, phenethyl and naphthylmethyl; $R_1$ and $R_2$ are independently selected from hydrogen, loweralkyl, cycloalkyl, $C_{2-4}$ loweralkenyl, benzyl, phenethyl and naphthylmethyl; Z is C=O; B is a bond or a $C_{1-5}$ alkylene, $C_{2-5}$ alkenylene or $C_{4-6}$ alkadienylene group; and Het is thienyl, furyl, pyrrolyl pyrazolyl, thiazolyl, isothiazolyl, oxazolyl, isoxazolyl, pyrrolidinyl, pyrrolinyl, imidazolidinyl, imidazolinyl, pyrazolidinyl, triazolyl, tetrazolyl, tetrahydrofuryl, pyranyl, pyridyl, pyrazinyl, pyrimidinyl, pyridazinyl, piperidyl, piperazinyl, morpholinyl, triazinyl, thiazinyl, benzothienyl, benzofuryl, isobenzofuryl, indolyl, isoindolyl, indazolyl, purinyl, quinolyl, isoquinolyl, naphthyridinyl, quinoxadinyl, chromanyl, indolinyl, isoimdolinyl, or chromenyl, unsubstituted or substituted by at least one substituent selected from halogen, hydroxyl, amino, carboxyl, $C_{1-8}$alkyl, oxo, $C_{1-8}$alkoxy, phenyl, naphthyl, chlorophenyl, benzyl, phenethyl, naphthylmethyl, (2,3,4- or 3,4,5 )trimethoxybenzyl, amino di-$C_{1-4}$alkylamino-$C_{1-4}$alkyl, hydroxy-substituted $C_{1-4}$alkyl, $C_{-5}$alkanoyloxy, strylcarbonyl, 3,4,5 -trimethoxystyrylcarbonyl, benzyloxycarbonylamino, benzyloxycarbonylaminomethyl, benzoylamino, 3,4,5 -trimethoxybenzoylamino, pyrrolidinylcarbonylmethyl, piperidylcarbonylmethyl, piperazinylcarbon-ylmethyl and morpholinylcarbonylmethyl are disclosed as anti ulcer agents in U.S. Pat. No. 4,610,983.

The term "loweralkyl" as used herein refers to straight or branched chain alkyl radicals containing from 1 to 8 carbon atoms including but not limited to methyl, ethyl, n-propyl, iso-propyl, n butyl, iso-butyl, sec butyl, n pentyl, 2 methylbutyl, 2,2-dimethylpropyl, n-hexyl, 2-methylpentyl, 2,2-dimethylbutyl, n-heptyl, n-octyl and the like.

The term "cycloalkyl" as used herein refers to an alicyclic ring having 3 to 8 carbon atoms, including, but not limited to cyclopropyl, cyclopentyl, cyclohexyl and the like.

The term "loweralkenyl" or "alkylene group" as used herein refers to a $(CH_2)_y$ radical where y is 1 to 8, such as methylene, ethylene, propylene, tetramethylene and the like.

The term "loweralkynyl" as used herein refers to a lower alkyl radical which contains at least one carbon-carbon triple bond.

The term "alkenylene group" as used herein refers to a $C_2$-$C_8$ chain of carbon atoms which contains at least one carbon-carbon double bond, such as vinylene, propenylene, butenylene and the like.

The term "alkadienylene group" as used herein refers to a $C_4$-$C_8$ chain of carbon atoms containing at least two carbon-carbon double bonds, such as 1,3-butadienylene and the like.

The term "halogen" as used herein refers to F, Cl, Br or I.

The terms "alkoxy" and "thioalkoxy" as used herein refer to $R_8O-$ and $R_8S-$ respectively, wherein $R_8$ is a loweralkyl group.

The term "alkoxyalkyl" as used herein refers to an alkoxy group appended to a loweralkyl radical, including, but not limited to methoxymethyl, 2-methoxyethyl and the like.

The term "aryl" or "aryl group" as used herein refers to phenyl, naphthyl, indanyl, fluorenyl, (1,2,3,4)-tetrahydronaphthyl, indenyl or isoindenyl.

The term "substituted aryl" as used herein refers to an aryl group substituted with one, two or three substituents independently selected from loweralkyl, alkoxy, thioalkoxy, carboxy, carboalkoxy, nitro, trihalomethyl, hydroxy, amino, and NH(loweralkyl).

The term "arylalkyl" as used herein refers to an aryl group appended to a loweralkyl radical, including, but not limited to benzyl, phenethyl, naphthylmethyl and the like.

The term "(substituted aryl)alkyl" as used herein refers to a substituted aryl group appended to a loweralkyl radical, including, but not limited to halobenzyl, alkoxynaphthylmethyl and the like.

The term "heterocyclic" or "heterocyclic group" as used herein refers to mono-, bi-, and tricyclic ring systems containing from one to four heteroatoms selected from the group consisting of nitrogen, sulfur, and oxygen; and having from 0 to 7 double bonds. Preferred heterocyclics are: thienyl, furyl, pyrrolyl, imidazolyl, pyrazoloyl, thiazolyl, isothiazolyl, oxazolyl, isoxazolyl, oxadiazolyl, oxatriazolyl, pyrrolidinyl, pyrrolinyl, imidazolidinyl, imidazolinyl, pyrazolidinyl, triazolyl, tetrazolyl, tetrahydrofuryl, pyranyl, pyronyl, pyridyl, pyrazinyl, pyrimidinyl, pyridazinyl, piperidyl, piperazinyl, pyrimidinyl, triazinyl, oxadiazinyl, isoxazinyl, oxathiazinyl, thiazinyl, oxadiazinyl, azepinyl, thiapinyl, thionaphthyl, benzofuryl, isobenzofuryl, indolyl, oxyindolyl, isoindolyl, indazolyl, indolinyl, 7-azaindolyl, isoindazolyl, anthranyl, benzopyranyl, coumarinyl, isocourmarinyl, purinyl, quinolyl, isoquinolyl, naphthyridinyl, cinnolinyl, quinazolinyl, pyridopyridyl, benzoxazinyl, diazepinyl, quinoxadinyl, chromenyl, chromanyl, isochromanyl, carbolinyl, xanthenyl, and acridinyl and

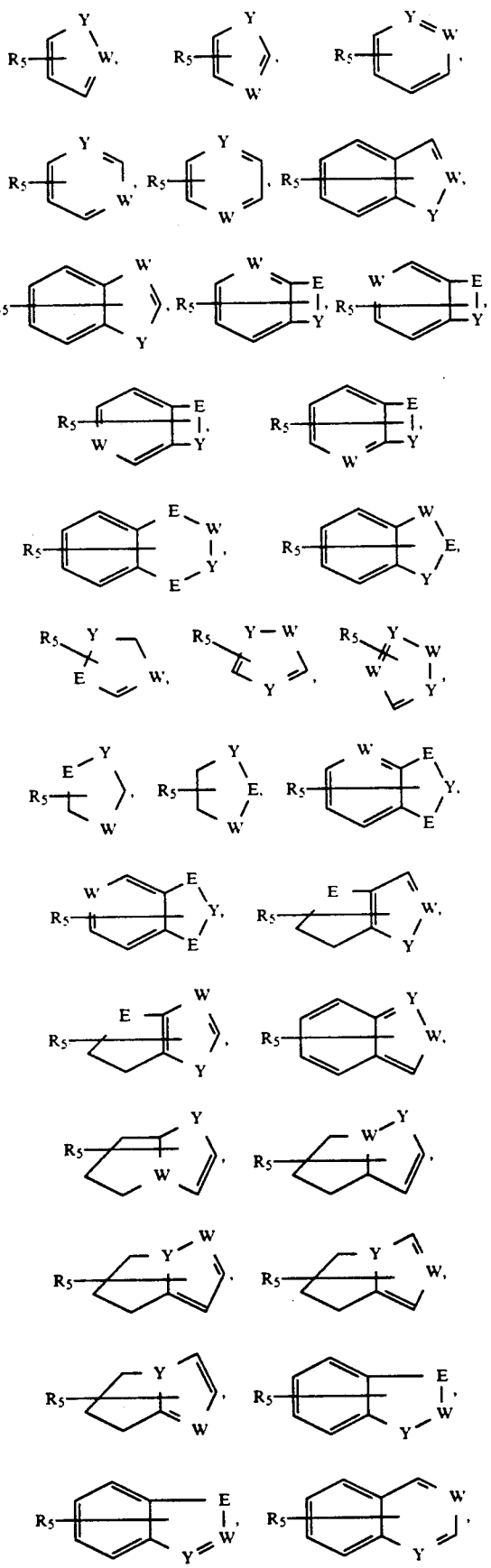

-continued

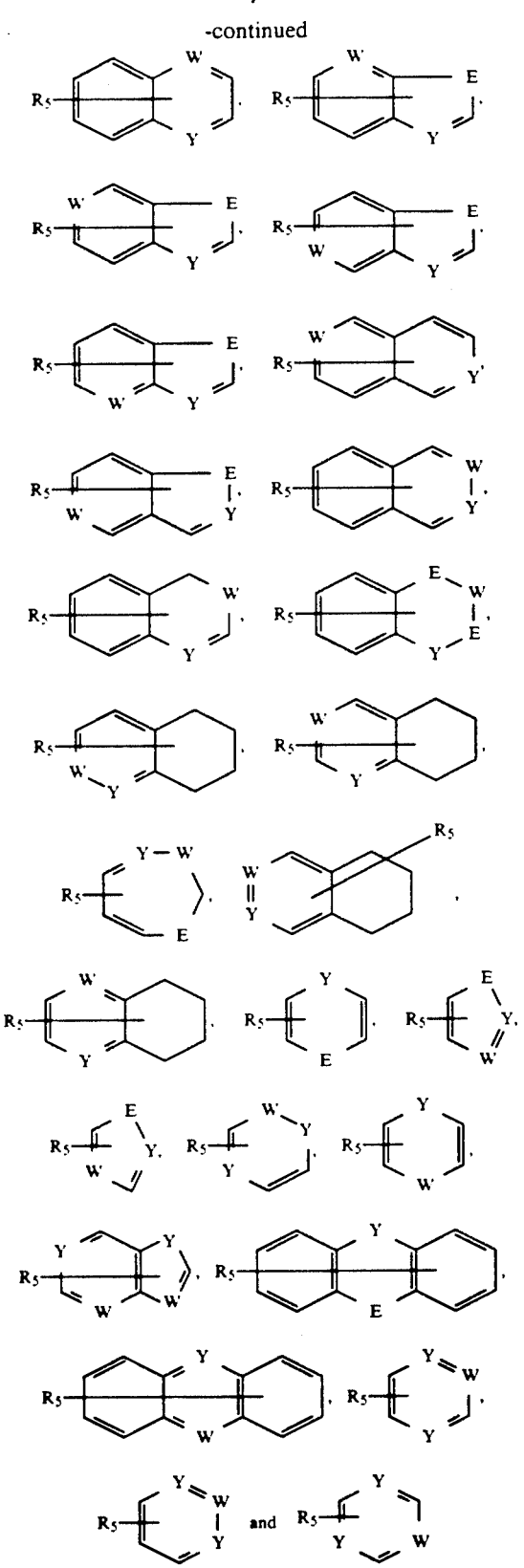

wherein E is selected from, $(CH_2)_p$, $(CH=CH)_r$, $C(O)CH_2$, $CH_2C(O)$, $QCH_2$, $CH_2Q$, $C(O)Q$, and $YC(O)$ wherein Q is S, O or $NR_{10}$ wherein $R_{10}$ is hydrogen, $-(C(O))(C_1-C_8 \text{loweralkyl})$, $-(C(O))$-cycloalkyl, $-(C(O))$-loweralkenyl, $-(C(O))$-lower alkynyl, thioalkoxy, $-(C(O))_q(CH_2)_m$aryl, $-(C(O))(CH_2)_m$(substituted aryl) wherein substituted aryl is as defined above, $-(CH_2)_m$carboxyl, $-(CH_2)_s(C(O))$aryl, $-(CH_2)_s(C(O))$(substituted aryl), $-(CH_2)_m$carboalkoxy, $-(CH_2)_m$carboxamide, $-(CH_2)_m$carboaryloxy, $-C(X)_3$ wherein X is halogen, $-(C(O))(CH_2)_sR_{11}$ wherein $R_{11}$ is hydrogen, loweralkyl, loweralkenyl, cycloalkyl, $-(CH_2)_m$aryl, $-(CH_2)_m$(substituted aryl) wherein substituted aryl is as defined above, $-(CH_2)_m$heterocyclic, nitro, halogen, CN, OH, $NH_2$, NHOH, $NR_6R_7$ wherein $R_6$ and $R_7$ are as previously defined, $NR_4OH$ wherein $R_4$ is hydrogen, $-(C(O))$-loweralkyl, $-(C)(O))$-loweralkenyl, $-(C(O))$-cycloalkyl, $-(C(O))$-loweralkynyl, $-(C(O))(CH_2)_m$aryl, $-(C(O))(CH_2)_m$(substituted aryl) wherein substituted aryl is as defined above, $-(CH_2)_mOR_4$ wherein $R_4$ is as defined above, or $-(CH_2)_mSR_4$ wherein $R_4$ is as defined above; with the proviso that Y and W are not both C; Y and W are independently selected from S, O, C, CH, $CH_2$ and $NR_{10}$ with the proviso that Y is not C, CH or $CH_2$ when W is C, CH or $CH_2$; and wherein $R_5$ is one, two or three substituents independently selected from hydrogen, $-(C(O))(C_1-C_6 \text{loweralkyl})$, $-(C(O))$-cycloalkyl, decahydronaphthyl, $-(C(O))$-loweralkenyl, $-(C(O))$-loweralkynyl, thioalkoxy, $-(C(O))(CH_2)_m$aryl, $-(C(O))(CH_2)_m$(substituted aryl), $-(CH_2)_m$carboxyl, $-(CH_2)_s(C(O))$aryl, $-(CH_2)_s(C(O))$(substituted aryl), $-(CH_2)_m$carboalkoxy, $-(CH_2)_m$carboxamide, $-(CH_2)_m$carboaryloxy, $-C(X)_3$ wherein X is halogen, $-(CO)(CH_2)_mR_6$ wherein $R_6$ is as previously defined, nitro, halogen, $-CN$, $-OH$, $-NH_2$, $-NHOH$, $-NR_6R_7$ wherein $R_6$ and $R_7$ are as previously defined, $-NR_4OH$ wherein $R_4$ is as previously defined, $-(CH_2)_mOR_4$ wherein $R_4$ is as defined above, $-(CH_2)_mSR_4$ wherein $R_4$ is as defined above; m is 0 to 4, p is 0 to 2, r is 0 to 1 and s is 1 to 4.

The symbols used to define the heterocyclic groups in which $R_5$ is attached to a bond which extends across 2 or 3 rings is meant to indicate that $R_5$ groups may be bonded to one, two or three of the rings of the heterocyclic ring system.

The term "arlyoxy" as used herein refers to $R_9O-$, wherein $R_9$ is an aryl or substituted aryl group.

The term "N-protecting group" or "N-protected" as used herein refers to those groups intended to protect the N-terminus of an amino acid or peptide or to protect an amino group against undersirable reactions during synthetic procedures or to prevent the attack of exopeptidases on the compounds or to increase the solubility of the compounds and includes but is not limited to sulfonyl, acyl, acetyl, pivaloyl, t-butyloxycarbonyl (Boc), carbonylbenzyloxy (Cbz), benzoyl or an L- or D-aminoacyl residue, which may itself be N-protected similarly.

The term "O-protecting group" as used herein refers to a substituent which protects hydroxyl groups against undesirable reactions during synthetic procedures and includes but is not limited to substituted methyl ethers, for example methoxymethyl, benzylozymethyl, 2-methoxyethoxymethyl, 2-(trimethylsilyl)ethoxymethyl, benzyl and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The terms "Glu" and "Asp" as used herein refer to glutamic acid and aspartic acid respectively.

The compounds of the invention may be made as shown in Scheme I. Compounds with DL, L, or D configuration may be used in the synthetic schemes.

As illustrated in Scheme I, N-protected omega-benzyl esters of alpha aminodicarboxylic acids 1 (preferably Boc (gamma-benzyl ester) D glutamic acid or Cbz-(gamma-benzyl ester)-D glutamic acid) are coupled with a primary or secondary amine (preferably dialkylamines, diaryl amines, or alkylaryl amines) using bis(2-oxo-3-oxazolidinyl)phosphinic chloride (BOPCl) or a conventional peptide coupling reagent (isobutyl chloroformate (IBCF), phosphorus pentachloride (PCl$_5$) and the like). The product amide 2 (P is Boc) is deprotected (preferably with hydrochloric acid (HCl) in dioxane) to provide the hydrochloride salt 3, or 2 is dideprotected (P is Cbz) to provide the free amine 4 (preferably using a transfer hydrogenolysis technique). The hydrochloride 3 is coupled with an arylcarboxylic acid (preferably indole-2-carboxylic acid or quinoline-3-carboxylic acid) using 1-ethyl 3 (3-dimethylaminopropyl)carbodiimide (EDCI) and triethyl amine in dimethylformamide (DMF) as solvent. Other conventional peptide coupling techniques may also be used. Substituents R'CH$_2$ can be introduced using the appropriate aldehyde (R'CHO) and amine hydrochloride 3 in a reductive amination reaction (preferably sodium cyanoborohydride or sodium borohydride in methanol or other alcohols as solvents) to provide compound 3a which can be coupled in analogous fashion to 3 to provide 5. Alternatively, the hydrochloride 3 can be directly alkylated with an alkylating agent (R'CH$_2$X wherein X is Cl, Br, I, OTs and the like) to provide the substituted amine 3a. The product amide 5 is debenzylated utilizing transfer hydrogenation techniques (preferably cyclohexadiene and palladium on carbon (Pd/C) in ethanol or other alcohols) to provide acid 6. Acid 6 also can be obtained from 5 through standard saponification conditions (aqueous hydroxide in alcohol, THF or dioxane). Alternatively the product 6 is obtained by coupling the amine 4 with active esters of arylcarboxylic acids (preferably indole 2-carboxy-2,4,6-trichlorophenyl ester). The acid 6 and alcohol (R$_4$OH) are coupled using dicyclohexylcarbodiimide (DCC) or other conventional peptide coupling reagent to provide ester 7. Acid 6 and secondary amine (NHR$_6$R$_7$) likewise are coupled with DCC (or other conventional peptide coupling reagent) to provide product 8. Alternatively the primary amine (R$_4$NH$_2$) can be used in place of the secondary amine to provide product 9. Product 9 is also obtained by the direct reaction of benzyl ester 5 and the primary amine (R$_4$NH$_2$) at high temperatures and/or pressures.

Reaction of hydrochloride 3 with arylsulfonylchloride in the presence of base (preferably an organic tertiary amine such as triethyl amine or N-methylmorpholine) provides product 10. Sulfonamide 10 is debenzylated in a similar fashion to 5 via either transfer hydrogenation conditions or saponification in alcoholic hydroxide. Reaction of hydrochloride salt 3 with a beta arylacrylic acid (preferably 3-(3'-pyridyl)-beta-acrylic acid) utilizing DCC (or other conventional peptide coupling technique) provides benzyl ester 12, which can be deprotected via either transfer hydrogenation conditions or saponification to provide product acid 13.

In addition, the hydrochloride salt 3 can be coupled, in the presence of base, with acylating agents that are available to one skilled in the art of organic synthesis, including, but not limited to isocyanates, isothiocyanates, acylcyanides, chloroformates and the like. These can be deprotected as previously outlined via hydrogenolysis or saponification to provide ureas, thioureas, carbamates and the like.

The N-carbobenzyloxy protected asparagine or glutamine 14 (preferably of the enantiomerically pure R configuration) is converted to its corresponding nitrile 15 by reaction with phosphorus oxychloride and pyridine (alternatively DCC and pyridine). The acid nitrile 15 is coupled with an appropriate amine (preferably dialkyl, diaryl, or alkylarylamine) using DCC (or a conventional coupling reagent) to yield the amide 16. The nitrile 16 is converted to the tetrazole 17 via reaction with sodium azide (NaN$_3$) in dimethylformamide (DMF). The tetrazole 17 is deprotected using standard hydrogenation (hydrogen atmosphere over palladium on carbon as catalyst) or transfer hydrogenation conditions to provide amine 18, which is reacted with an active ester of the desired arylcarboxylic acid to provide product 19.

SCHEME I

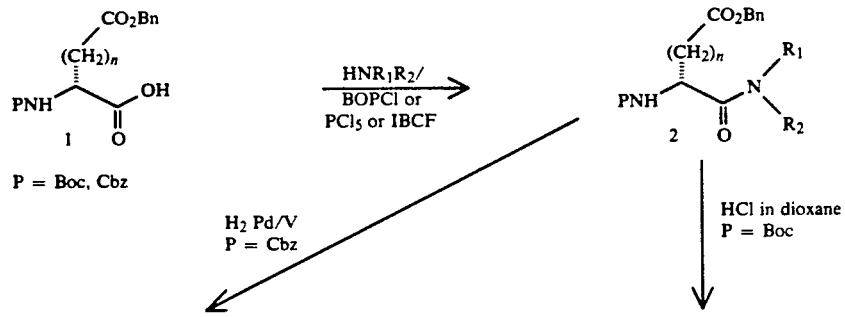

P = Boc, Cbz

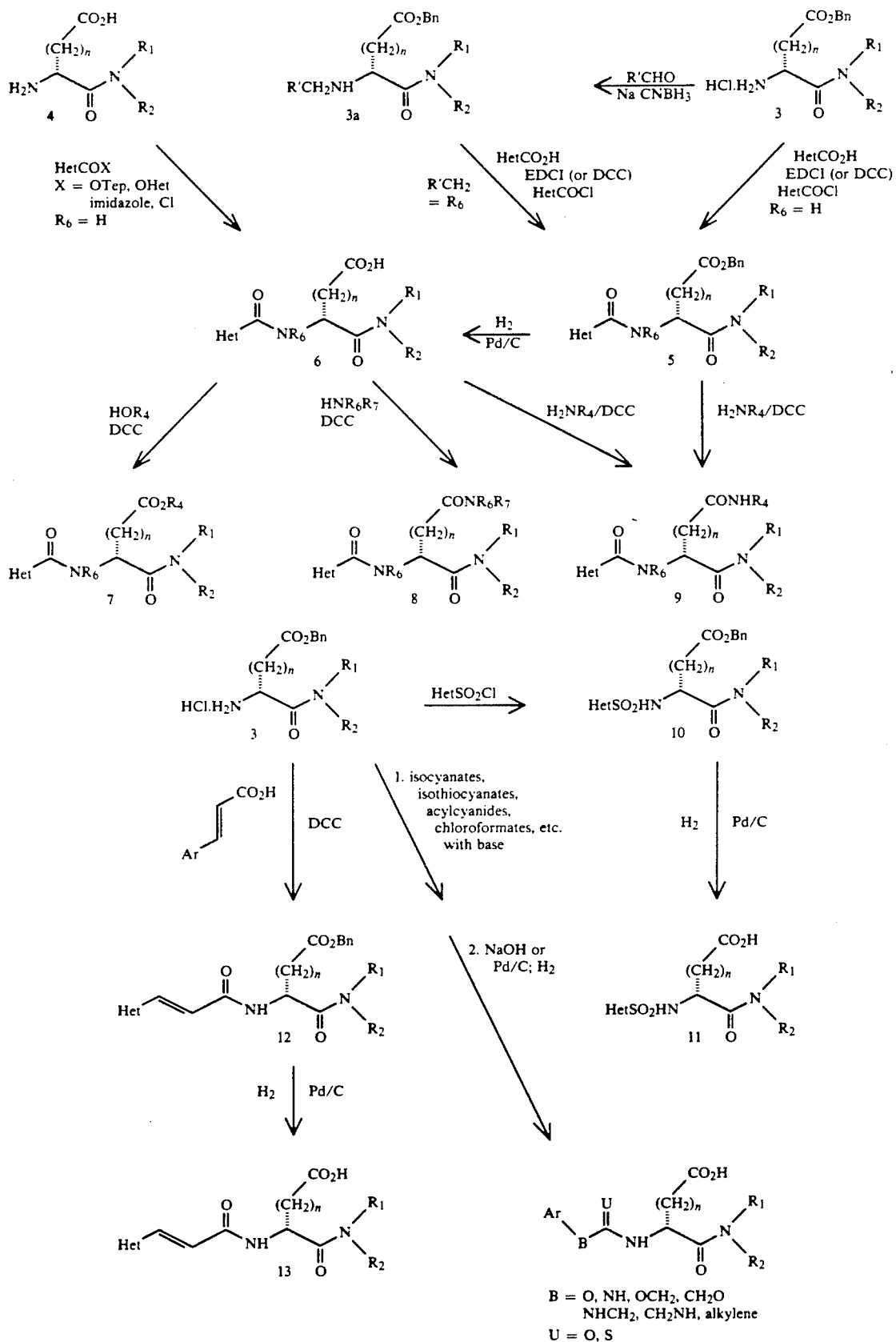
SCHEME I

-continued
SCHEME I

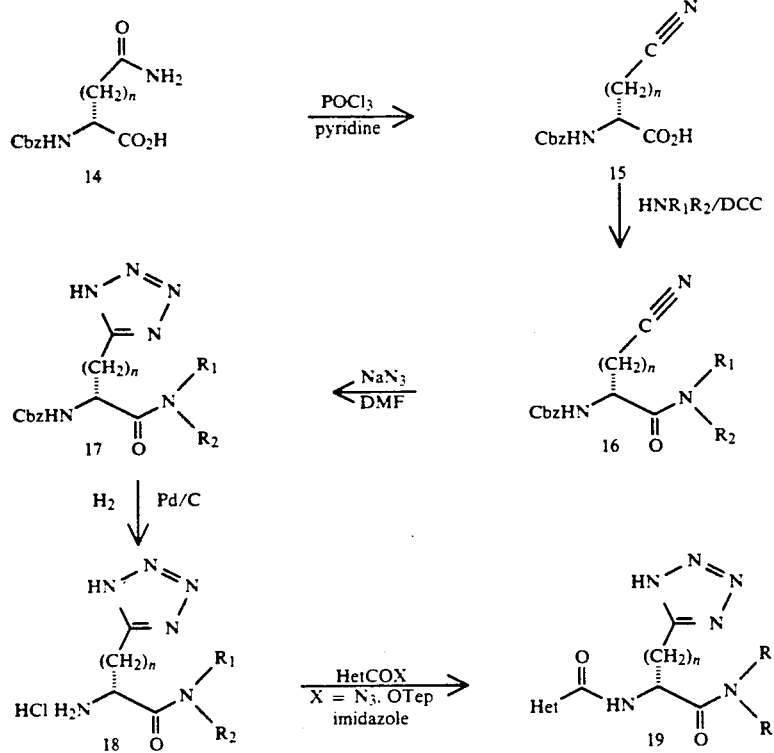

The following examples will serve to further illustrate preparation of the novel compounds of the invention.

EXAMPLE 1

N-Boc-(γ-benzyl ester)-R-Glu-di-n-pentylamide

To the solution of Boc-(γ-benzyl ester)-R-Glutamic acid (4.0 g, 11.9 mmol) in tetrahydrofuran (THF) (100 mL) was added bis (2-oxo-3-oxazolidinyl)-phosphinic chloride (BOPCl) (3.1 g, 11.9 mmol) and di-n-pentylamine (6 mL, 30 mmol) at room temperature. The reaction mixture was allowed to stir overnight. The solvents were evaporated and the residue dissolved in ethyl acetate (300 mL) and washed with 1 N hydrochloric acid (HCl), saturated NaHCO$_3$ (sodium bicarbonate), H$_2$O and brine and dried over magnesium sulfate (MgSO$_4$). After evaporation of solvents the product was subjected to flash chromatography using ethyl acetate (EtOAc)-hexane (2:8) as the elutant. The pure oily product was isolated in 78.1% yield (4.5 g). $[\delta]_D = -26.1°$ (c=1.3, methanol (MeOH)). MS(CI) m/e 477(m+H)$^+$, 421, 381, 363, 325, 299, 282. $^1$H NMR(CDCl$_3$, 300MHz) δ 0.9(m,6H), 1.3(m,8H), 1.4(s,9H), 1.6(m,4H), 1.7(m,2H), 2.5(m,2H), 3.1-3.2(m,2H), 3.5(m,2H), 4.6(m,1H), 5.1(s,2H), 5.4(d,1H,J=9Hz), 7.4(s,5H).

EXAMPLE 2

(γ-Benzyl ester)-R-Glu-di-n-pentylamide hydrochloride t-Butyloxycarbonyl derivative of example 1, (1.2 g, 2.5 mmol) was dissolved in 5 mL of 4M HCl in dioxane and the mixture was stirred for 30 min. The solvents were evaporated and the residue was triturated several times with ether and the volatiles were evaporated. The product was filtered and washed several times with diethyl ether. Yield 0.9 g (96%). MS(CI) m/e 377(m+H)$^+$, 359, 269, 241. $^1$H NMR(DMSO$_{d6}$, 300MHz) δ 0.8-0.9(m,6H), 1.15-1.35(m,8H), 1.4-1.6(m,4H), 1.90-2.05(m,2H), 2.45-2.70(m,2H), 3.05(m,1H), 3.15(m,1H), 3.30(H$_2$O), 3.35-3.55(m,2H), 4.23(m,1H), 5.1(bs,2H), 7.37(bs,5H), 8.2-8.4(bs,2H).

EXAMPLE 3

N-(2'-Indolylcarbonyl)-(γ-benzyl ester)-R-Glu-di-n-pentylamide

To a solution of hydrochloride of example 2 (7 g, 17 mmol) and N-methylmorpholine (NMM) (3.8 mL, 34.5 mmol) in dimethylformamide (DMF) at 0° C. was added indole-2-carboxylic acid (2.75 g, 17 mmol), 1-hydroxybenzotriazole (HOBt) (4.9 g, 6.3 mmol) followed by 1-ethyl-3-(3-dimethylaminopropyl) carbodiimide (EDCI) (3.25 g, 17 mmol). The reaction mixture was allowed to warm to ambient temperature and was stirred overnight. The solvent was concentrated under vacuo and after addition of water, the mixture was extracted successively with N hydrochloric acid, water, saturated solution of sodium bicarbonate and brine. The solution was dried over magnesium sulfate and filtered. Purification was accomplished by crystallization from ethyl acetate and hexane providing 7.55 g (85.6%) of product. $[\delta]D = +24.00°$ (c=0.5, MeOH). mp=84°-86° C. MS(CI) m/e 520(m+H)$^+$, 429, 286, 144. $^1$H NMR(CDCl$_3$, 300MHz) δ 0.85-0.95(m,6H), 1.2-1.4 (m,8H), 1.50-1.66(m,4H), 2.0(m,1H), 2.20(m,1H), 2.40-2.65(m,2H), 3.1(m,1H), 3.25(m,1H), 3.48-3.62(m,2H), 5.05(d,1H,J TM 12Hz), 5.14 (d,1H,J=12Hz), 5.18(dt,1H,J=3,9Hz), 6.95(d,1H,J=2Hz), 7.15(dt,1H,J=1,7.5Hz), 7.3(m,2H), 7.35(m,5H), 7.4(d,1H,J=7.5 Hz), 7.65(d,1H,J=7.5Hz), 9.22(bs,1H) Analysis calculated for $C_{31}H_{41}N_3O_4 \cdot H_2O$: C 71.03, H 7.98, N 8.02; Found: C 71.05, H 7.98, N 8.03.

EXAMPLE 4

N-(2,-Indolylcarbonyl)-R-Glu-$N^\alpha,N^\alpha$-di-n-pentylamide

To a suspension of 0.9 g 10% palladium on carbon (Pd/C) in methanol (10 mL) and cyclohexadiene (3 mL) was added under nitrogen atmosphere ($N_2$) a solution of benzyl ester of example 3 (1.3 g, 2.5 mmol) in methanol by cannula. The reaction mixture was stirred overnight at ambient temperature. The mixture was filtered through celite and washed several times with methanol. The filtrate and washings were combined and concentrated under vacuo. The product was purified by flash chromatography using chloroform ($CHCl_3$)-methanol and ammonium hydroxide ($NH_4OH$) 90:10:1 as elutant. Lyophilization provided product in 83.8% yield (0.9 g). mp=78°-79° C. $[\delta]D=+2.8°$ (c=1.0, MeOH). MS(FAB) m/e 430(m+H)+, 273, 245, 226. 1H NMR(DMSO$_{d6}$,300MHz) δ 0.8–0.9(m,6H), 1.12–1.38(m,8H), 1.39–1.5(m,4H), 1.56–1.81(m,2H), 1.85–2.0(m,2H), 2.3(t,J=6Hz,2H), 3.18(m,1H), 3.54–3.62(m,2H), 4.85(m,1H), 7.03(t,J=7Hz,1H), 7.18(t,J=7Hz,1H), 7.25(s,1H), 7.43(d,=9Hz,1H), 7.61(d,J=9Hz,1H), 8.8(d,J=8Hz,1H), 11.6(bs,1H). Analysis calculated for $C_{24}H_{35}N_3O_4 \cdot H_2O$ C 65.77, H 8.18, N 9.59. Found: C 65.99, H 8.01, N 9.76.

EXAMPLE 5

N-(2,-Quinolycarbonyl)-(γ-benzyl ester)-R-Glu-di-n-pentylamide

To a solution of hydrochloride of example 2 (0.25 g, 0.61 mmol) and N-methylmorpholine (0.14 mL, 1.2 mmol) in DMF (5 mL) at 0° C. was added HOBt (0.16 g, 1.2 mmol) and quinoline-2-carboxylic acid (0.11 g, 0.61 mmol) followed by EDCI (0.125 g, 0.65 mmol). The reaction mixture was stirred overnight at room temperature. The solvent was evaporated. After addition of water, the mixture was extracted with ethyl acetate. Combined ethyl acetate extracts were washed with 1.0 N hydrochloric acid, water, a saturated solution of sodium bicarbonate and brine. The solution was dried over magnesium sulfate. The ethyl acetate was evaporated and residue was purified by chromatography using hexane and ethyl acetate as elutant. The product was isolated in 33% yield (0.1 g). MS(CI) m/e 532(m+H)+, 347, 156, 128, 91. 1H NMR(CDCl$_3$,300MHz) δ 0.85–0.95(m,6H), 1.2–1.45(m,8H), 1.6(m,4H), 2.05(m,1H), 2.25(m,1H), 2.46–2.68(m,2H), 3.1(m,1H), 3.3(m,1H), 3.6(m,2H), 5.12(s,2H), 5.25(dt,J=3,9Hz,1H), 7.4(m,5H), 7.6(dt,J=1,6Hz,1H), 7.78(dt,J=1,6Hz,1H), 7.9(d,J=9Hz,1H), 8.15(d,J=9Hz,1H), 8.25(d,J=3Hz,1H), 8.30(d,J=9Hz,1H), 9.1(d,J=9Hz,1H).

EXAMPLE 6

N-(2,-Quinolylcarbonyl)-R-Glu-$N^\alpha,N^\alpha$-di-n-pentylamide

To a suspension of 0.1 g 10% Pd/C in methanol (3 mL) and cyclohexadiene (1 mL) was added under inert atmosphere ($N_2$) a solution of benzyl ester of example 5 (0.09 g, 0.170 mmol) in methanol by cannula. The reaction mixture was stirred overnight at ambient temperature. The mixture was filtered through celite and washed several times with methanol. The filtrate and washings were combined and concentrated in vacuo. The product was purified by flash chromatography using chloroform-methanol and ammonium hydroxide 90:10:1 as elutant. Lyophilization provided product in 60% yield (0.045 g). MS(CI) m/e 442(m+H)+, 332, 286, 257, 156, 128. 1H NMR(CDCl$_3$, 300MHz) δ 0.82–0.92(m,6H), 1.2–1.4(m,8H), 1.50–1.68(m,4H), 2.0(m,1H), 2.2(m,1H), 2.5(m,2H), 3.1(m,1H), 3.25(m,1H), 3.48–3.70(m,2H), 5.2(dt,J=3,9Hz,1H), 7.60(dt,J=1,6Hz,1H), 7.75(dt,J=1,6Hz,1H), 7.85(d,J=6Hz,1H), 8.18(d,J=9Hz,1H), 8.25(d,J=6Hz,1H), 8.31(d,J=9Hz,1H), 9.2(d,J=6Hz,1H). Analysis calculated for $C_{25}H_{35}N_3O_4 \cdot 0.5 H_2O$: C 66.64, H 7.95, N 9.33. Found: C 66.65, H 7.87, N 9.21.

EXAMPLE 7

N-(2'-Indolylcarbonyl)-(γ-benzyl ester)-S-Glu-di-n-pentylamide

To a solution of hydrochloride prepared analogously as in example 2 (0.92 g, 2.23 mmol) and N-methylmorpholine (0.5 mL, 4.5 mmol) in DMF at 0° C. was added indole-2-carboxylic acid (0.36 g, 2.23 mmol), HOBt (0.45 g, 3.35 mmol) followed by EDCI (0.44 g, 2.23 mmol). The reaction mixture was allowed to warm to ambient temperature and was stirred overnight. The solvent was concentrated in vacuo. After addition of ethyl acetate and water, the mixture was extracted with 1.0 N hydrochloric acid, water, a saturated solution of sodium bicarbonate and brine. The solution was dried over magnesium sulfate and filtered. Purification was accomplished by crystallization from ethyl acetate and hexane providing 0.8 g (69.1 %) of product. mp=83°-84° C. $[\alpha]_D=-23.55°$ (c=1.0, MeOH). MS(CI) m/e 520(m+H)+. 1H NMR(CDCl$_3$, 300MHz) δ 0.8–0.9(m,6H), 1.2–1.45(m,8H), 1.52–1.6(m,4H), 2.0(m,1H), 2.2(m,1H), 2.4–2.65(m,2H), 3.1(m,1H), 3.25(m,1H), 3.5–3.68(m,2H), 5.1(d,J=4Hz,1), 5.15(d,J=12Hz,1H), 5.2(m,1H), 6.9(d,J=3Hz,1H), 7.15(t,J=9Hz,1H), 7.3(m,1H), 7.35(m,6H), 7.4(d,J=9Hz,1H), 7.65(d,J=9Hz,1H), 9.2(s,1H).

EXAMPLE 8

N-(2'-Indolylcarbonyl)-S-Glu-$N^\alpha,N^\alpha$-di-n-pentylamide

To a suspension of 0.5 g 10% Pd/C in methanol (10 mL) and cyclohexadiene (3 mL) was added under inert atmosphere ($N_2$) solution of benzyl ester of example 7 (0.8 g, 1.55 mmol) in methanol by cannula. The reaction mixture was stirred overnight at ambient temperature. The mixture was filtered through celite and washed several times with methanol. The filtrate and washings were combined and concentrated in vacuo. The product was purified by flash chromatography using chloroform-methanol and ammonium hydroxide 90:10:1 as elutant. Lyophilization provided product in 89.5 % yield (0.6 g). mp=76°-74° C. $[\delta]_D=-6.5°$ (c=0.8, MeOH). MS(CI) m/e 430(m+H)+, 273, 245, 144. 1H NMR(DMSO$_{d6}$,300MHz) δ 0.8–0.9(m,6H), 1.12–1.45(m,8H), 1.48–1.5(m,4H), 1.53–1.75(m,2H), 1.80–2.0(m,2H), 2.3(t,J=6Hz,2H), 3.0–3.13(m,2H), 4.85(m,1H), 7.03(t,J=9Hz,1H), 7.18(t,J=9Hz,1H), 7.25(s,1H), 7.4(d,J=9Hz,1H), 7.6(d,J=9Hz,1H), 8.6(d,J=9Hz,1H), 11.6(s,1H), 12.2(bs,1H). Analysis calculated for $C_{24}H_{35}N_3O_4 \cdot 0.33 H_2O$: C 66.19, H 8.25, N 9.65. Found: C 66.39, H 8.23, N 9.65.

EXAMPLE 9

N-(2'-Quinoxalylcarbonyl)-(r-benzyl ester)-R-Glu-di-n-pentylamide

To the stirred solution of hydrochloride of example 2 (0.37 g, 0.9 mmol) and pyridine (0.2 mL, 2 mmol) in anhydrous DMF (2 mL) at 0° C. was added dropwise a solution of 2-quinoxalyl chloride (0.8 g, 0.95 mmol) in DMF (2 mL) over 2 hours. The reaction was monitored by tlc using hexane-ethylacetate mixture in 2:1 ratio. Solvents were evaporated and the residue diluted with ethyl acetate and washed successively with 1.0 N hydrochloric acid, water, a solution of saturated bicarbonate and brine. The solution was dried over magnesium sulfate. The product was purified by chromatography (EtOAc/hexane) to provide 0.355 g (74%). MS(CI) m/e 533(m+H)+, 377, 348. $^1$H NMR(CDCl$_3$, 300MHz) δ 0.82–0.98(t,J=6Hz,6H), 1.23–1.45(m,8H), 1.5–1.7(m,4H), 2.05(m,1H), 2.3(m,1H), 2.5–2.65(m,2H), 3.1(m,1H), 3.3(m,1H), 3.5–3.72(m,2H), 5.15(s,2H), 5.25(dt,J=4,9Hz,1H), 7.35(m,5H), 7.85(m,2H), 8.15(dd,J=1.5,12Hz,2H), 8.78(d,J=9Hz,1H), 9.62(s,1H).

EXAMPLE 10

N-(2'-Quinoxalylcarbonyl)-R-Glu-N$^a$,N$^a$-di-n-pentylamide

To a suspension of 0.08 g 10% Pd/C in absolute ethanol (EtOH, 4 mL) and cyclohexadiene (1 mL) was added under inert atmosphere (N$_2$) solution of benzyl ester of example 9 (0.08 g, 0.15 mmol) in ethanol via cannula. The reaction mixture was stirred overnight at ambient temperature. The mixture was filtered through celite and washed several times with ethanol. The filtrate and washings were combined and concentrated under vacuo. The product was purified by flash chromatography using chloroform-methanol and ammonium hydroxide 90:10:1 as elutant. Lyophilization provided product in 90.0% yield (0.06 g). [α]$_D$= +12.67° (c=0.6, MeOH). MS(CI) m/e 443(m+)+, 258. $^1$H NMR (CDCl$_3$, 300MHz) δ 0.78–0.98(m,6H), 1.2–1.4(m,8H), 1.48–1.65(m,4H), 1.8(m,1H), 2.25(m,1H), 3.05(m,1H), 3.25(m,1H), 3.5–3.75(m,2H), 4.18(m,2H), 5.3(t,J=9Hz,1H), 7.8(m,2H), 8.1(m,2H), 8.9(d,J=9Hz,1H), 9.5(s,1H).

EXAMPLE 11

N-(3'-Indolylcarbonyl)-(γ-benzyl ester)-R-Glu-di-n-pentylamide

To the stirred solution of hydrochloride of example 2 (1.15 g, 2.8 mmol) in DMF at 0° C. and N-methylmorpholine (0.65 mL, 5.6 mmol) was added HOBt (0.75 g, 5.6 mmol) and quinoline-3-carboxylic acid (0.45 g, 2.9 mmol) followed by EDCI (0.57 g, 3.0 mmol). The reaction was allowed to warm to ambient temperature over 2 hours and stirred overnight. Solvent was evaporated and to the residue was added water and ethyl acetate. The organic extracts were washed successively with 1 N hydrochloric acid, water, a solution of saturated sodium bicarbonate and brine. The solution was dried over magnesium sulfate and filtered. The product was purified by chromatography using ethyl acetate and hexane as eluant. Product was obtained in 56.6% yield (0.85 g). MS(CI) m/e 520(m+)+, 363, 335, 279. $^1$H NMR(CDCl$_3$, 300MHz) δ 0.85–0.95(m,6H), 1.2–1.42(m,8H), 1.5–1.7(m,4H), 1.88–2.02(m,1H), 2.25(m,1H), 2.6(m,2H), 3.1(m,1H), 3.28(m,1H), 3.6(m,2H), 5.1(s,2H), 5.3(dt,J=3,9Hz,1H), 7.1(d,J=7.5Hz,1H), 7.25(m,2H), 7.3(m,5H), 7.5(m,1H), 7.8(d,J=2Hz,1H), 8.1(m,1H), 8.9(s,1H).

EXAMPLE 12

N-(3'-Indolylcarbonyl)-R-Glu-N$^a$,N$^a$-di-n-pentylamide

To a suspension of 0.3 g 10% Pd/C in absolute ethanol (5 mL) and cyclohexadiene (2 mL) was added under inert atmosphere (N$_2$) a solution of benzyl ester of example 11 (0.41 g, 0.79 mmol) in ethanol by cannula. The reaction mixture was stirred overnight at ambient temperature. The mixture was filtered through celite and washed several times with ethanol. The filtrate and washings were combined and concentrated under vacuo. The product was purified by flash chromatography using chloroform-methanol and ammonium hydroxide 90:10:1 as elutant. Lyophilization provided product in 65% yield (0.22 g). MS(CI) m/e 430(m+H)+, 269, 245. $^1$H NMR (DMSO$_{d6}$,300MHz) δ 0.8–0.9(m,6H, 1.15–1.32(m, 8H, 1.4–1.72(m,4H), 1.78–1.9 (m, 2H), 2.20(m, 2H), 3.1–3.4(m,2H), 3.6(m,2H), 4.95(m,1H), 7.12(m,2H), 7.41(d,J=9Hz,1H), 7.93(d,J=7Hz,1H), 8.1(d,J=6Hz,1H), 8.18(d,J=2Hz,1H), 11.5(s,1H, 12.15(bs, 1H). Analysis calculated for C$_{24}$H$_{35}$N$_3$O$_4$: C 67.10, H 8.21, N 9.78. Found: C 66.97, H 8.30, N 9.75.

EXAMPLE 13

N-(1',2',3',4'-Tetrahydroquinoxalyl-2'-carbonyl)-R-Glu-N$^a$,N$^a$-di-n-pentylamide To a suspension of 0.3 g 10% Pd/C in absolute ethanol (5 mL) and formic acid (80%) (1 mL) was added under inert atmosphere (N$_2$) a solution of benzyl ester of example 9 (0.355 g, 0.67 mmol) and 0.15 g ammonium formate in ethanol via cannula. The reaction mixture was stirred overnight at ambient temperature. The mixture was filtered through celite and washed several times with methanol. The filtrate and washings were combined and concentrated in vacuo. The product was purified by flash chromatography using chloromethanol and ammonium hydroxide 90:10:1 as elutant. Lyophilization provided product in 67% yield (0.2 g). [α]$_D$= +12.67° (c=0.6, MeOH). MS(CI) m/e 447(m+H)+. $^1$H NMR(CDCl$_3$,300MHz) δ 0.84–0.96(m,6H), 1.20–1.38(m,8H), 1.42–1.70(m,4H), 1.9–2.02(m,2H), 2.30(m,2H), 3.05(m,1H), 3.18(m,1H), 3.38–3.6(m,4H), 3.7(d,J=3Hz,1H), 3.73(d,J=3Hz,1H), 4.1(m,1H), 5.0(dt,J=2,12Hz,1H), 6.7(d,J=6Hz,1H), 6.15(d,J=6Hz,1H), 6.2(m,2H), 7.85(d,J=9Hz,1). Analysis calculated for C$_{24}$H$_{38}$N$_4$O$_4$ 0.9 H$_2$O: C62.29, H 8.64, N 12.11. Found: C 62.03, H 8.31, N 12.47.

EXAMPLE 14

N-(3'-Quinolylcarbonyl)-(γ-benzyl ester)-R-Glu-di-n-pentylamide

To a solution of hydrochloride of example 2 (0.41 g, 1 mmol) and N-methylmorpholine (0.22 mL, 2 mmol) in DMF at 0° C. was added quinoline-3-carboxylic acid (0.17 g, 1 mmol), HOBt (0.27 g, 2 mmol) followed by EDCI (0.2 g, 1.05 mmol). The reaction mixture was allowed to warm to ambient temperature and then stirred overnight. The solvent was evaporated and water was added to the residue. The mixture was extracted with ethyl acetate. Combined ethyl acetate extracts were washed successively with 1 N hydrochloric acid, water, a saturated solution of sodium bicarbonate, brine and the solution dried over magnesium sulfate then filtered and concentrated in vacuo. Purification by chromatography using ethyl acetate and hexane as elutants provided 0.4 g (75%) of product. MS(CI) m/e 531(m)+, 374, 347, 156, 128, 91. $^1$H NMR(CDCl$_3$,300MHz) δ 0.85-0.98(m,6H), 1.2-1.42(m,8H), 1.5-1.7(m,4H), 2.02-2.28(m,2H), 2.50(m,2H), 3.15(m,1H), 3.35(m,1H), 3.5-3.62(m,2H), 5.15(s,2H), 5.30(dt,J=3,9Hz,1H), 7.35(m,5H), 7.65(t,J=7.5Hz,1H) 7.85(t,J=7.5Hz,1H), 7.96(d,J=9Hz,1H), 8.1(d,J=9Hz,1H), 8.26(d,J=9Hz,1H), 8.82(s,1H), 9.4(d,J=0.5Hz,1H).

EXAMPLE 15

N-(3'-Quinolylcarbonyl)-R-Glu-N$^\alpha$,N$^\alpha$-di-n-pentylamide

To a suspension of 0.3 g 10% Pd/C in methanol (10 mL) and cyclohexadiene (3 mL) was added under inert atmosphere (N$_2$) a solution of benzyl ester of example 14 (0.4 g, 0.75 mmol) in methanol via cannula. The reaction mixture was stirred overnight at ambient temperature. The mixture was filtered through celite and washed several times with methanol. The filtrate and washings were combined and concentrated in vacuo. The product was purified by flash chromatography using chloroform-methanol and ammonium hydroxide 90:10:1 as elutant. Lyophilization provided product in 60% yield (0.21 g). [α]$_D$= −2.4° (c=0.5, MeOH). MS(FAB) m/e 464(m+Na)+, 442(m+H)+, 285, 257. $^1$H NMR(CDCl$_3$, 300MHz) δ 0.8-0.95(m,6H), 1.18-1.4(m,8H), 1.45-1.7(m,4H), 2.02(m,1H), 2.2(m,1H), 2.54(m,2H), 3.1(m,1H), 3.25(m,1H), 3.5(m,2H), 5.23(m,1H), 7.55(t,J=9Hz,1H), 7.75(t,J=9Hz,1H), 7.8(d,J=9Hz,1H), 8.08(d,J=9Hz,2H), 8.62(d,J=2Hz,1H), 9.3(d,J=2Hz,1H). Analysis calculated for C$_{25}$H$_{35}$N$_3$O$_4$ 0.75 H$_2$O C 65.98, H 8.09, N 9.23. Found: C 65.92, H 8.21, N 8.86.

EXAMPLE 16

Boc-(β-benzyl ester)-R-Asp-di-n-pentylamide

Boc-(β-benzyl ester)-R-Aspartic acid (1.06 g, 3.29 mmol) was stirred at 0° C. in 35 mL of methylene chloride (CH$_2$Cl$_2$) under inert atmosphere. Dipentyl amine (7.0 mL) was added to the mixture followed by the addition of BOPCl (1.0 g). The reaction was maintained at 0° C. and when product had formed by tlc the mixture was taken up in ethyl acetate. The organic solvents were washed several times with water then twice with a 1.0 N hydrochloric acid solution, lastly with a saturated sodium bicarbonate solution. The mixture was dried over magnesium sulfate, filtered and concentrated in vacuo. The residue was purified using a chromatotron and ethyl acetate/hexane mixtures as the elutants to provide 974 mg of product. $^1$H NMR(CDCl$_3$, 300MHz) δ 7.35(m,5H), 5.3(bd,J=9Hz,1H), 5.13(d,J=12Hz,1H), 5.08(d,J=12Hz,1H), 4.95(m,1H), 3.39(m,2H), 3.10-3.30(m,2H), 2.82(dd,J=7,16Hz,1H), 2.63(dd,J=7,16Hz,1H), 1.45-1.65(m,4H), 1.42(bs,9H), 1.39(m,8H), 0.89(m,6H).

EXAMPLE 17

(β-Benzyl ester)-R-Asp-di-n-pentylamide hydrochloride

Boc-(β-benzyl ester)-R-Asp-di-n-pentyl amide (974 mg) was dissolved in 3.0 mL of a 4.0 N hydrochloric acid solution in dioxane. The reaction was monitored by tlc for disappearance of starting material. When reaction was complete the mixture was diluted with diethyl ether and hexane and volatiles removed in vacuo. This process was repeated three times leaving a thick clear oil which was used for subsequent reactions.

EXAMPLE 18

Hydrochloride salt of example 17 (270 mg, 0.67 mmol), indole 2-carboxylic acid (129 mg, 0.80 mmol), HOBt (100 mg, 0.74 mmol) and EDCI (165 mg, 0.86 mmol) were suspended in 8 mL of anhydrous dimethylformamide at 0° C. Triethyl amine (TEA) (200 μL) was added and the reaction mixture stirred under nitrogen allowing warming to ambient temperature overnight. The mixture was taken up in ethyl acetate and washed with water, 1.0 N hydrochloric acid solution, and saturated sodium bicarbonate solution. The organic solution was dried over magnesium sulfate, filtered and the residue purified by chromatography utilizing a chromatotron and ethyl acetate/hexane elutant mixtures to provide 223 mg of product. mp=94°-5° C. [α]$_D$= +44.8° (c=0.125, MeOH). MS(CI) m/e 506(m+)+, 407, 363, 346, 321. $^1$H NMR(CDCl$_3$, 300MHz) δ 9.18(bs,1H), 7.63(bd,J=7.5Hz,1H), 7.42(bd,J=7.5Hz,1H), 7.32(m,7H), 7.14(dt,J=1.5,7.5Hz,1H), 6.85(s,1H), 5.48(dt,J=6,9Hz,1H), 5.12(m,2H), 3.15-3.50(m,4H), 2.92(dd,J=6,15Hz,1H), 2.29(dd,J=6,15Hz,1H), 1.45-1.60(m,4H), 1.2-1.35(m,8H), 0.88(m,6H). C,H,N Analysis calculated for C$_{30}$H$_{39}$N$_3$O$_4$ 0.3 EtOAc: C 70.43, H 7.84, N 7.90; Found C 70.31, H 8.08, N 7.67.

EXAMPLE 19

N-(2'-Indolylcarbonyl)-R-Asp-N$^\alpha$,N$^\alpha$-di-n-pentylamide

To a suspension of 97 mg of 10% Pd on carbon in ethanol under nitrogen atmosphere was added 100 μL of cyclohexadiene. To this mixture was then added 112 mg of the benzyl ester of example 18 and 400 μL of cyclohexadiene. The reaction was monitored by tlc for the disappearance of starting material. When reaction was complete the mixture was filtered through celite and the volatiles removed in vacuo. The residue was lyophilized to provide product. mp=183°-5° C. [α]$_D$= +27.1° (c=0.17, acetone). MS(FAB) m/e 438(m+Na)+, 416(m+H)+, 373, 317, 273, $^1$H NMR(DMSO$_{d6}$,300MHz) δ 11.63(s,1H), 8.87(d,J=9Hz,1H), 7.60(d,J=7.5Hz,1H), 7.42(d,J=7.5Hz,1H), 7.24(d,J=1.5Hz,1H), 7.18(dt,J=1.5,7.5Hz,1H), 7.02(t,J=7.5Hz,1H), 5.25(m,1H), 3.2-3.5(bs,H$_2$O), 2.84(dd,J=8,16Hz,1H), 1.58(bs,2H), 1.43(m,2H), 1.15-1.30(m,8H), 0.85(t,J=7.5Hz,3H), 0.77(t,J=7.5Hz,3H). C,H,N Analysis calculated for C$_{23}$H$_{33}$N$_3$O$_4$ 0.4 H$_2$O: C 65.33, H 8.06, N 9.94; Found C 65.32, H 8.16, N 9.72.

EXAMPLE 20

N-(2'-Quinolylcarbonyl)-(β-benzyl ester)-R-Asp-di-n-pentyl amide (β-Benzyl ester)-R-Asp-dipentyl amide hydrochloride (105 mg, 0.26 mmol), quinoline-2-carboxylic acid (57 mg, 0.33 mmol), HOBt (36 mg) and EDCI (55 mg, 0.28 mmol) were suspended in 5 mL of dimethyl formamide stirring at 0° C. under nitrogen. To this mixture was added 400 μL of triethyl amine and the reaction mixture was allowed to stir overnight while warming to ambient temperature. The reaction mixture was taken up in ethyl acetate and washed with one portion of water, two portions of 1.0 N hydrochloric acid and a saturated sodium bicarbonate solution. The organics were dried over magnesium sulfate, filtered and the volatiles removed in vacuo. The residue was purified by chromatography to provide 99.5 mg of product. MS(EI) m/e 517(m)+, 362, 333, 156, 128, 91. $^1$H NMR(CDCl$_3$, 300MHz) δ 8.87(d,J=9.7Hz,1H), 8.32(d,J=7.5Hz,1H), 8.25(d,J=9Hz,1H), 8.12(bd,J=9Hz,1H), 7.87(d,J=7.5Hz,1H), 7.78(dt,J=1.5,9Hz,1H), 7.62(dt,J=1.5,9Hz,1H), 7.25-7.35(m,5H), 5.55(m,1H), 5.17(d,J=12Hz,1H), 5.10(d,J=12Hz,1H), 3.4(m,3H), 3.25(m,1H), 3.10(dd,J=7.5,16Hz,1H), 2.84(dd,J=6,16Hz,1H), 1.55(m,4H), 1.20-1.35(m,8H), 0.88(t,J=7Hz,3H), 0.80(t,J=7Hz,3H).

EXAMPLE 21

N-(2'-Quinolylcarbonyl)-R-Asp-N$^\alpha$,N$^\alpha$-di-n-pentylamide

The β-Benzyl ester of example 20 (93 mg, 0.18 mmol) in 2 mL of ethanol were added to 87 mg of 10% palladium on carbon stirring in 4 mL of ethanol under a nitrogen atmosphere. Cyclohexadiene (500 μL) was added and the reaction was monitored for disappearance of starting material. When this had occurred the reaction mixture was filtered through celite and the residue concentrated and then lyophilized from water to provide product (56 mg). mp=91°-3° C. [δ]$_D$= +1.25° (c=0.08, MeOH). MS(FAB) m/e 472(m+2Na-H)+, 450(m+Na)+, 428(m+H)+. $^1$H NMR(CDCl$_3$, 300MHz) δ 9.05(d,J=7.5Hz,1H), 8.28(d,J=9Hz,1H), 8.22(d,J=9Hz,1H), 8.12(bd,J=7.5Hz,1H), 7.83(bd,J=7.5Hz,1H), 7.75(bt,J=7.5Hz,1H), 7.61(bt,J=7.5Hz,1H), 5.50(dt,J=6,9Hz,1H), 3.35-3.50(m,3H), 3.25(m,1H), 3.04(dd,J=6,16Hz,1H), 2.85(dd,J=5,16Hz,1H), 2.5(bs,1H), 1.60(m,4H), 1.25(m,8H), 0.88(t,J=7.5Hz,3H), 0.80(t,J=7.5Hz,3H). C,H,N Analysis calculated for C$_{24}$H$_{33}$N$_3$O$_4$ 0.5 H$_{20}$: C 66.02, H 7.85, N 9.63; Found C 66.18, H 7.81, N 9.49.

EXAMPLE 22

N-(2'-Indolylcarbonyl)-R-Gln-N$^\alpha$,N$^\alpha$-di-n-pentylamide

Ammonia was bubbled into a solution of N-(2'-indoylcarbonyl)-(γ-benzyl ester)-R-Glu-di-n-pentyl amide (50 mg) in methanol at −78° C. and the reaction vessel sealed. Stirring continued over 48 hrs with warming to ambient temperature. The volatiles were evaporated in vacuo and product isolated as a white solid (37 mg). mp=71°-4° C. [α]$_D$= −2.8° (c=0.5, acetone). MS(FAB) m/e 429(m+)+, 396, 272, 244. $^1$H NMR(DMSO$_{d6}$,300MHz) δ 11.6(bs,1H), 8.57(bd,J=7.5Hz,1H), 7.61(d,J=7.5Hz,1H), 7.41(d,J=7.5Hz,1H), 7.30(m,2H), 7.17(bt,J=7.5Hz,1H), 7.03(bt,J=7.5Hz,1H), 6.82(bs,1H), 4.84(m,1H), 3.35(bm,H$_2$O), 3.08(m,1H), 2.20(m,2H), 1.75-1.90(m,2H), 1.70(m,1H), 1.6(m,1H), 1.45(m,2H), 1.2-1.33(m,8H), 0.86(m,6H). C,H,N Analysis calculated for C$_{24}$H$_{36}$N$_4$O$_3$ 0.2 H$_2$O: C 66.68, H 8.49, N 12.97; Found C 66.64, H 8.43, N 12.91.

EXAMPLE 23

N-(2'-Indolylcarbonyl)-(γ-methyl ester)-R-Glu-di-n-pentylamide

To a solution of N-(2'-Indolylcarbonyl)-R-Glu-di-n-pentylamide (38 mg) stirring in ethyl acetate at ambient temperature was added an excess of diazomethane solution in ether. The excess diazomethane was destroyed by acetic acid (HOAc) addition and the product was isolated by concentration and filtration through a plug of silica gel providing 28 mg of methyl ester. mp=93°-4° C. [δ]$_D$= +11.1° (c=0.045, MeOH). MS(CI) m/e 444(m+)+, 287, 269, 158. $^1$H NMR(CDCl$_3$, 300MHz) δ 9.12(bs,1H), 7.66(d,J=7.5Hz,1H), 7.42(bd,J=7.5Hz,1H), 7.22-7.32(m,2H), 7.13(dt,J=1.5,7.5Hz,1H), 6.95(m,1H), 5.25(dt,J=4,9Hz,1H), 3.68(s,3H), 3.58(m,2H), 3.27(m,1H), 3.10(m,1H), 2.40-2.60(m,2H), 2.2(m,1H), 1.9(m,1H), 1.5-1.7(m,4H), 1.25-1.4(m,8H), 0.91(m,6H). C,H,N Analysis calculated for C$_{25}$H$_{37}$N$_3$O$_4$ 0.5 H$_2$O: C 66.33, H 8.47, N 9.28. Found C 66.24, H 8.22, N 9.18.

EXAMPLE 24

N-Boc-(γ-benzyl ester)-R-Glu-benzylamide

To a solution of Boc-(γ-benzyl ester)-R-glutamic acid (258 mg) and BOPCl (250 mg) in methylene chloride (7 mL) at 0° C. and under nitrogen atmosphere was added benzyl amine (90 μL). The reaction mixture was allowed to stir overnight and reach ambient temperatures. The mixture was taken up in ethyl acetate and extracted with two portions of water, two portions of 0.5 N hydrochloric acid, and one of saturated aqueous sodium bicarbonate solution. The solution was dried over magnesium sulfate and filtered. The solution was concentrated and chromatography of the residue provided 65 mg of product. MS(CI) m/e 427(m+)+, 399, 371. $^1$H NMR(CDCl$_3$, 300MHz) δ 7.23-7.46(m,10H), 6.50(bs,1H), 5.23(bs,1H), 5.12(s,2H), 4.43(bd,J=6Hz,2H), 4.18(m,1H), 2.4-2.6(m,2H), 2.18(m,1H), 1.96(m,1H), 1.41(bs,9H).

EXAMPLE 25

N-(3'-Quinolylcarbonyl)-(γ-benzyl ester)-R-Glu-benzylamide

Boc-(γ-benzyl ester)-R-Glu-di-n-pentyl amide (58 mg) was treated with 4.0 mL of 4.5 M hydrochloric acid in dioxane at 0° C. until starting material was consumed by tlc analysis. The volatiles were evaporated in vacuo and the residue was stirred with 3-quinolinecarboxylic acid (68 mg), EDCI (74 mg), and HOBt (22 mg) in 4 mL of anhydrous DMF under nitrogen at 0° C. To this reaction was added triethyl amine (75 μL) and the reaction was allowed to warm to ambient temperature overnight. The mixture was taken up in ethyl acetate and extracted with two portions of water, one portion of 1.0 N hydrochloric acid and once with saturated sodium bicarbonate solution. The organic solution was dried over magnesium sulfate and filtered. Removal of the volatiles in vacuo and trituration of the residue with ethyl acetate provided 44 mg of product. mp=160°-62° C. [α$_D$= −15.0° (c=0.08, acetone). MS(CI) m/e 482(m+)+, 374, 347. $^1$H NMR(CDCl$_3$, 300MHz) δ 9.25(m,1H), 8.83(m,1H), 8.08(m,2H), 7.89(m,1H), 7.71(m,1H), 7.4(m,10H), 4.87(bs,6H), 4.7(m,1H), 2.58(bt,J=7.5Hz,2H), 2.30(m,1H), 2.20(m,1H). C,H,N Analysis calculated for C$_{29}$H$_{27}$N$_3$O$_4$ 0.833 H$_2$O: C 70.13, H 5.82, N 8.46; Found C 70.06, H 5.46, N 8.62.

EXAMPLE 26

N-Boc-(γ-benzyl ester)-R-Glu-dibenzylamide

To a solution of Boc-(γ-benzyl ester)-R-Glutamic acid (715 mg) and BOPCl (750 mg) stirring in 15 mL of methylene chloride at 0° C. was added dibenzyl amine (800 mg). The reaction mixture was allowed to stir overnight and warm to ambient temperature. The reaction mixture was taken up in ethyl acetate and extracted twice with 0.5 N hydrochloric acid solution and then with aqueous saturated sodium bicarbonate solution. The solution was dried over magnesium sulfate and filtered. The mixture was concentrated in vacuo and the residue purified by chromatography utilizing ethyl acetate and hexane as the elutants to provide 571 mg of product. MS(CI) m/e 516(m)+, 460, 443, 416, 369, 325, 292, 236. $^1$H NMR(CDCl$_3$,300MHz) δ 7.35(m,11H), 7.18(m,4H), 5.45(bd,J=9Hz,1H), 5.1(m,2H), 4.7–4.9(m,3H), 4.45(d,J=16Hz,1H), 4.3(d,J=16Hz,1H), 2.45(m,2H), 2.10(m,1H), 1.82(m,1H), 1.43(bs,9H).

EXAMPLE 27

(γ-Benzyl ester)-R-Glu-dibenzylamide hydrochloride

Boc-(γ-benzyl ester)-R-Glu-dibenzylamide (571 mg) was treated with 7.0 mL of a 4.5 M solution of hydrochloric acid in dioxane at −20° C. under nitrogen atmosphere. The reaction was stirred 3 hours at which time tlc indicated no more starting material. The mixture was concentrated in vacuo and the residue triturated with diethyl ether. The volatiles again were evaporated in vacuo and diethyl ether added to the residue. Filtration provided the product as a white solid (475 mg).

EXAMPLE 28

N-(2′-Indoylcarbonyl)-(γ-benzyl ester)-R-Glu-dibenzylamide

EDCI (129 mg), HOBt (10 mg), 2-indolecarboxylic acid (117 mg) and hydrochloride salt of example 27 (236 mg) were suspended in 5 mL of anhydrous DMF under nitrogen at −20° C. To this mixture was added triethyl amine 170 μL and reaction mixture stirred overnight allowing the reaction to warm to ambient temperature. The reaction mixture was taken up in ethyl N hydrochloric acid and once with saturated aqueous sodium bicarbonate solution. The solution was dried over magnesium sulfate and filtered. Concentration of the solution in vacuo and chromatography of the residue provided 240 mg of product. Crystallization of a small sample from ethyl acetate/hexane provided an analytically pure sample. mp=94°–6° C. [α]$_D$= +4.5° (c=0.11, MeOH). MS(FAB) m/e 560(m+)+, 363, 335, 234. $^1$H NMR(CDCl$_3$, 300MHz) δ 9.05(bs,1H), 7.68(d,J=7.5Hz,1H), 7.29–7.45(m,14H), 7.20(m,5H), 7.0(m,1H), 5.38(dt,J=3,9Hz,1H), 5.10(d,J=15Hz,1H), 5.05(d,J=15Hz,1H), 4.95(d,J=15Hz,1H), 4.82(d,J=15Hz,1H), 4.45(d,J=15Hz,1H), 4.22(d,J=15Hz,1H), 2.40–2.60(m,2H), 2.25(m,1H), 2.03(m,1H). C,H,N analysis calculated for C$_{35}$H$_{33}$N$_3$O$_4$ C 75.11, H 5.95, N 7.51; Found C 75.63, H 6.00, N 7.55.

EXAMPLE 29

N-(2′-Indolylcarbonyl)-R-Glu-N$^α$,N$^α$-dibenzylamide (210 mg) was stirred in 3 mL of methanol and 3.0 mL of 1.0 N sodium hydroxide (NaOH) solution was added at room temperature. The reaction was stirred until tlc analysis indicated the complete disappearance of starting material. The mixture was then concentrated in vacuo and the residue taken up in ethyl acetate and portioned with saturated sodium bicarbonate solution. The aqueous solution was separated and acidified with hydrochloric acid to pH 2.0. This solution was extracted three times with equal portions of ethyl acetate and these extracts were combined and dried over magnesium sulfate. Filtration and evaporation of the volatiles in vacuo provided a residue which when triturated with hexane gave product. mp=111°–3° C. [δ]$_D$= −5.4° (c=0.13, acetone). MS(FAB) m/e 470(m+)+, 273, 234. $^1$H NMR(DMSO$_{d6}$,300MHz) δ 11.65(bs,1H), 8.75(d,J=7.5Hz,1H), 7.63(d,J=7.5Hz,1H), 7.15–7.45(m,14H), 7.05(t,J=7.5Hz,1H), 5.10(m,1H), 4.90(d,J=16Hz,1H), 4.71(d,J=15Hz,1H), 4.50(d,J=16Hz,1H), 4.17(d,J=15Hz,1H), 2.37(bt,J=7Hz,2H), 2.0(m,2H). C,H,N Analysis calculated for C$_{28}$H$_{27}$N$_3$O$_4$ 0.4 H$_2$O: C 70.53, H 5.88, N 8.82; Found C 70.49, H 5.79, N 8.79.

EXAMPLE 30

Methyl N-Boc-γ-benzyl ester)-R-Glutamic acid (692 mg), EDCI (583

N-Boc-(γ-benzyl ester)-R-Glutamic acid (692 mg), EDCI (583 mg), HOBt (220 mg), and R-phenylglycine methyl ester hydrochloride (384 mg) were suspended in 15 mL of anhydrous DMF at −20° C. under nitrogen atmosphere. Triethylamine (700 μL) was added and the reaction mixture was allowed to stir overnight with warming to ambient temperature. The mixture was taken up in a large volume of ethyl acetate and extracted with water, 1.0 N solution of hydrochloric acid, and saturated sodium bicarbonate solution. The solution was dried over magnesium sulfate and then filtered. Evaporation of the volatiles in vacuo and chromatography of the residue provided 832 mg of product. MS(FAB) m/e 485(m+)+, 429, 385, 367, 277. $^1$H NMR(CDCl$_3$, 300MHz) δ 7.36(bm,11H), 5.54(d,J=7.5Hz,1H), 5.23(m,1H), 5.15(m,2H), 4.26(m,1H), 3.72(s,3H), 2.54(dt,J=3,7.5Hz,2H), 2.18(m,1H), 1.98(m,1H), 1.42(s,9H).

EXAMPLE 31

Methyl N-(2′-Indolylcarbonyl)-(γ-benzyl ester)-R-Glutamyl-R-phenylglycinate

Boc-(γ-benzyl ester)-R-Glu-R-phenylglycine methyl ester (832 mg) was treated with 6.0 mL of 4.5 M hydrochloric acid in dioxane at 0° C. When tlc analysis of the reaction mixture indicated complete consumption of the starting material the solvents were removed in vacuo. Several times ether and hexane were added to the residue and solvents evaporated in vacuo. The resulting oily product was used without further purification. Hydrochloride salt (260 mg), 2-indolecarboxylic acid (121 mg), EDCI (163 mg), and HOBt (96 mg) were suspended in 7.0 mL anhydrous DMF at −10° C. and triethyl amine (210 μL) was added. The reaction mixture was stirred and warmed to ambient temperature overnight. The mixture was taken up in a large volume of ethyl acetate and extracted with two portions of water, two portions of 1.0 N hydrochloric acid solution, and saturated sodium bicarbonate solution. The solution was dried over magnesium sulfate and filtered and the volatiles evaporated in vacuo. Chromatography of the residue utilizing ethyl acetate and hexane mixtures as the elutants provided 262 mg of product. mp=177°–8° C. [δ]$_D$= −71.9° (c=0.32 DMSO-MeOH (1/1)). MS(CI) m/e 528(m+)+, 436, 420, 395, 363, 294, 277. $^1$H NMR(CDCl$_3$, 300MHz) δ 9.25(bs,1H), 7.75(m,1H), 7.67(d,J=7.5Hz,1H), 7.26–7.40(m,13H), 7.14(t,J=7.5Hz,1H), 6.94(s,1H), 5.55(d,J=7.5Hz,1H), 5.12(m,2H), 4.88(m,1H), 3.74(s,3H), 2.65(m,2H), 2.25(m,2H). C,H,N Analysis calculated for C$_{30}$H$_{29}$N$_3$O$_6$ C 68.28, H 5.54, N 7.97; Found: C 68.29, H 5.66, N 8.08.

EXAMPLE 32

Methyl N-(3'-Quinolylcarbonyl)-(γ-benzyl ester)-R-Glutamyl-R-phenylglycinate

Hydrochloride salt used in example 31 (373 mg), 3-quinolinecarboxylic acid (168 mg), EDCI (210 mg) and HOBt (96 mg) were suspended in 9.0 mL of anhydrous DMF stirring at $-10°$ C. under nitrogen atmosphere. Triethyl amine (280 μL) was added and the resulting mixture stirred overnight warming to ambient temperature. The mixture was taken up in a large volume of ethyl acetate and extracted twice with portions of water, twice with 1.0 N hydrochloric acid solutions, and once with saturated sodium bicarbonate. The solution was then dried over magnesium sulfate and filtered. Evaporation of the volatiles and chromatography of the residue utilizing ethyl acetate and hexane mixtures as the elutants provided 367 mg of product mp=144°-6° C. $[\delta]_D = +69.56°$ c=0.11, MeOH). MS(CI) m/e 540(m+H)+, 432, 375, 347, 294. ¹H NMR(CDCl₃,300MHz) δ 9.32(d,J=3Hz,1H), 8.58(m,1H), 8.15(d,J=7.5Hz,1H), 7.9(d,J=7.5Hz,1H), 7.83(m,1H), 7.60(m,3H), 7.34(m,10H), 5.55(d,J=7Hz,1H), 5.18(m,2H), 4.83(m,1H), 3.73(s,3H), 2.60-2.85(m,2H), 2.20-2.40(m,2H). C,H,N Analysis calculated for $C_{31}H_{29}N_3O_6$ C 68.99, H 5.42, N 7.79; Found: C 68.88, H 5.45, N 7.78.

EXAMPLE 33

N-(6,-Quinolylcarbonyl)-(γ-benzyl ester)-R-Glu-di-n-pentyl amide

Hydrochloride salt of example 2 (190 mg), EDCI (138 mg), HOBt (86 mg), and 6-quinolinecarboxylic acid (99.6 mg) were suspended in 6.0 mL of anhydrous DMF at 0° C. under a nitrogen atmosphere. Triethyl amine (165 μL) was added and the reaction mixture stirred overnight with warming to ambient temperature. The reaction mixture was poured into a large volume of ethyl acetate and this solution was extracted twice with water, twice with 1.0 N hydrochloric acid solution, and once with saturated sodium bicarbonate solution. The solution was dried over magnesium sulfate and filtered. Evaporation of the volatiles in vacuo and chromatography of the residue provided 245 mg of product. $[\delta]_D = +16.9°$ (c=0.61, MeOH). MS(CI) m/e 532(m+H)+, 424, 398, 375, 347, 264. ¹H NMR(CDCl₃, 300MHz) δ 8.97(dd,J=1.5,5Hz,1H), 8.30(s,1H), 8.18(dd,J=1.5,9Hz,1H), 8.10(bs,2H), 7.71(bd,J=8Hz,1H), 7.44(m,1H), 7.30-7.35(m,5H), 5.25(dt,J=3.5,9Hz,1H), 5.14(bs,2H), 3.60(m,2H), 3.30(m,1H), 3.12(dt,J=7.5,14Hz,1H), 2.45-2.70(m,2H), 2.25(m,1H), 2.04(m,1H), 1.68(m,2H), 1.55(m,2H), 1.2-1.4(m,8H), 0.92(m,6H).

EXAMPLE 34

N-(6'-Quinolylcarbonyl)-R-Glu-Nα,Nα-d-n-pentylamide

To a suspension of 249 mg of palladium on carbon (10%) in 5 mL of ethanol under nitrogen atmosphere was added 100 μL of cyclohexadiene, followed by 154 mg of benzyl ester of example 33 in 5 mL of ethanol. To this reaction mixture was added an additional 400 μL of cyclohexadiene and the reaction was monitored for consumption of starting material. The reaction mixture was filtered through celite and the volatiles removed in vacuo. Crystallization from ethyl acetate and hexane gave 114 mg of product. mp=146°-8° C. $[\alpha]_D = -18.9°$ (c=0.095, acetone) MS(CI) m/e 442(m+)+, 398, 323, 304, 294, 257, 173, 158. ¹H NMR(CDCl₃, 300MHz) δ 8.94(dd,J=1.5,4.5Hz,1H), 8.27(d,J=1.5Hz,1H), 8.10-8.18(m,2H), 8.02(d,J=9Hz,1H), 7.70(d,J=7.5Hz,1H), 7.42(dd,J=4.5,8.5Hz,1H), 5.24(m,1H), 3.45-3.65(m,2H), 3.2-3.35(m,1H), 3.05-3.17(m,1H), 2.55(m,2H), 2.23(m,1H), 2.05(m,1H), 1.65(m,2H), 1.55(m,2H), 1.25-1.40(m,8H), 0.90(m,6H). C,H,N analysis calculated for $C_{25}H_{35}N_3O_4$ 0.33 $H_2O$: C 67.08, H 8.04, N 9.39; Found: C 67.10, H 7.96, N 9.34.

EXAMPLE 35

Methyl N-(t-Butyloxycarbonyl)-(γ-benzyl ester)-R-Glutamyl S-phenylglycinate

N-(t-Butyloxycarbonyl)-(γ-benzyl ester)-R-glutamic acid (2.13 gram) and methyl-S-phenylglycinate hydrochloride were reacted in a fashion similar to that in example 21 to provide 1.00 grams (33% yield) of product after chromatography. mp=91°-92° C. $[\alpha]_D = +54.6°$ (c=0.52, acetone). MS(FAB) m/e 485(m+H)+, 429, 385, 367, 350, 345, 325, 277. ¹H NMR(CDCl₃,300MHz) δ 7.33(m,10H), 7.23(m,1H), 5.53(d,J=7.5Hz,1H), 5.25(m,1H), 5.13(s,2H), 4.25(m,1H), 3.72(s,3H), 2.52(m,1H), 2.40(m,1H), 2.14(m,1H), 1.94(m,1H), 1.42(bs,9H).

EXAMPLE 36

Methyl N-(2'-Indolylcarbonyl)-(γ-benzylester)-R-Glutamyl-S-phenylglycinate

Boc-(γ-benzyl ester)-R-Glu-S-phenylglycine methyl ester (362 mg) was treated with 8.0 mL of 4.5 M hydrochloric acid in dioxane at $-10°$ C. under nitrogen atmosphere. Reaction progress was monitored by tlc and when starting material was consumed the solvents were removed in vacuo. EDCI (212 mg), HOBt (100 mg), and indole-2-carboxylic acid (133 mg) were added to this residue and the contents dissolved in 15 mL of anhydrous DMF at 0° C. Triethyl amine (260 μL) was added and the reaction was allowed to stir overnight under nitrogen warming to ambient temperature. The reaction mixture was poured into ethyl acetate and extracted twice with portions of water, twice with portions of 1.0 N HCl solution and once with saturated sodium bicarbonate solution. The solution was dried over magnesium sulfate, filtered, and concentrated in vacuo. Chromatography of the residue provided 230 mg of the desired product. mp=179°-81° C. $[\delta]_D = +49.4°$ (c=0.34, MeOH). MS(CI) m/e 528(m+H)+, 437, 420, 395, 294. ¹H NMR(CDCl₃, 300MHz) δ 9.38(bs,1H), 7.8(d,J=7.5Hz,1H), 7.65(d,J=7.5Hz,1H), 7.3-7.45(m,13H), 7.14(dt,J=1.5,7.5Hz,1H), 6.98(m,1H), 5.58(d,J=7.5Hz,1H), 5.1(s,2H), 4.92(m,1H), 3.71(s,3H), 2.62(m,1H), 2.41(m,1H), 2.15-2.32(m,2H). C,H,N Analysis calculated for $C_{30}H_{29}N_3O_6$ C 68.28, H 5.54, N 7.97; Found: C 68.38, H 5.63, N 7.74.

EXAMPLE 37

Methyl N-(2'-Indolylcarbonyl)-R-Glutamyl-S-phenylglycinate

To a suspension of 81 mg of palladium (10%) on carbon in 2 mL of ethanol under nitrogen atmosphere were added cyclohexadiene (100 μL) followed by a solution of benzyl ester of example 36 in 2.0 mL of ethanol. An additional 400 μL of cyclohexadiene was added and the reaction stirred at room temperature until starting material was consumed by tlc analysis. The reaction mixture was filtered through celite and the filtrate concentrated in vacuo. The residue was lyophilized to provide 36 mg of final product. mp=133°-9° C. $[\alpha]_D = +18.4°$ (c=0.065, acetone). MS(FAB) m/e 438 (m+)+, 391, 273, 245. 1H NMR(DMSO$_{d6}$,300MHz) δ 11.63(bs,1H), 9.43(bs,1H), 8.92(d,J=7.5Hz,1H), 7.61(d,J=7.5Hz,1H), 7.40(m,7H), 7.23(bs,1H), 7.18(t,J=7.5Hz,1H), 7.03(t,J=7.5Hz,1H), 5.47(m,1H), 4.55(m,1H), 3.62(s,3H), 3.25-3.50(H$_2$O), 2.21(bt,J=7.5Hz,2H), 1.93(m,2H). C,H,N Analysis calculated for $C_{23}H_{23}N_3O_6$ 1.33 H$_2$O: C 59.85, H 5.56, N 9.11; Found C 59.76, H 5.16, N 8.74.

EXAMPLE 38

N-(2'-Indolylcarbonyl)-R-Glu-N$^\alpha$-(2'-biphenylamide)

To a solution of Boc(r-benzyl ester)-R-Glutamic acid (337 mg, 1.0 mmol) and 2-aminobiphenyl (423 mg, 2.5 mmol) in THF (15 mL) at 4° C. were added TEA (140 mL, 1.0 mmol) and BOPCl (254 mg, 1.0 mmol) and the reaction was allowed to warm to room temperature overnight. The reaction mixture was poured into EtOAc and extracted with portions of 1 M phosphoric acid (H$_3$PO$_4$); 1 M Na$_2$CO$_3$ (sodium carbonate); H$_2$O then dried over MgSO$_4$. Evaporation of the solvent gave a pink oil. Flash chromatography on silica gel eluted with 8:1 hexanes-ethyl acetate gave: 246 mg, (0.51 mmol, 51% yield). R$_f$=0.46 (2:1 hexanes-EtOAc); 0.24 (4:1 hexanes-EtOAc). The material above was treated with HCl-dioxane (1.5 mL, 6 mmol) under an N$_2$ atmosphere for 4 hours at room temperature. The reaction was evaporated in vacuo and then placed under high vacuum overnight. R$_f$=0.63 (100:60:18:33 EtOAc-pyridine-HOAc-H$_2$O). The HCl salt (0.51 mmol), 2-indole carboxylic acid (97 mg, 0.60 mmol), HOBt (81 mg, 0.60 mmol) and TEA (167 μL, 1.2 mmol) were dissolved in CH$_2$Cl$_2$ (8 mL) and treated with EDCI (115 mg, 0.66 mmol) at room temperature overnight. The solvent was evaporated in vacuo and the residue was dissolved in EtOAc and extracted with successive portions of 1 M H$_3$PO$_4$ (3×), 1 M Na$_2$CO$_3$ (3×), H$_2$O-brine, then dried over MgSO$_4$, filtered and evaporated. The oily residue was crystallized from give 209 mg, (0.394 mmol, 77%, R$_f$=0.23 (2/1 hexane-EtOAc)). The benzyl ester (190 mg, 0.36 mmol) in MeOH (10 mL) and acetic acid (HOAc, 5 mL) was treated with 10% Pd/C (prewetted with MeOH under N$_2$ atmosphere, 25 mg) under 1 atmosphere H$_2$ (balloon) for 1.5 hours at room temperature. The catalyst was filtered, the solvent was evaporated in vacuo and the residue was recrystallized from aqueous ethanol. Yield: 127 mg, (0.29 mmol, 81%). R$_f$=0.28 (80:20:1 CHCl$_3$—MeOH—NH$_4$OH). mp=136°-42° C. (becomes translucent). $[\alpha]_D = +7.5°$ (1.2, MeOH). MS(FAB+) m/e 442(m+)+, 464(m+Na)+, 273(-168), 245(-196). $^1$H NMR(DMSO$_{d6}$,300MHz) δ 1.83-1.96(m,1H), 1.98-2.10(m,1H), 2.30(brt,2H), 4.50(m,1H;dd(+D$_2$O),J=5,9Hz), 7.05(dt,1H), 7.12-7.40(m,9H), 7.46(d,1H), 7.63(d,J=7Hz,1H), 7.68(d,J=5Hz,1H), 8.55(d,J=7Hz,1H), 9.30(s,1H), 11.6(s,1H), 12.16(brs,1H). Analysis calculated for $C_{26}H_{23}N_3O_4$ H$_2$O: C 69.32, H 5.37, N 9.33, Found: C 69.58, H 5.27, N, 9.33.

EXAMPLE 39

Boc-(γ-benzyl ester)-R-Glu-(diphenylmethyl)amide

BOPCl (255 mg, 1.0 mmol) was added to a solution of Boc-(γ-benzyl ester)-R-Glutamic acid (337 mg, 1.0 mmol) and diphenylmethylamine (431 mL, 2.5 mmol) in dry THF cooled to 4° C. The reaction was allowed to attain room temperature overnight. The reaction mixture was poured into EtOAc and extracted successively with 1 M H$_3$PO$_4$ (3×), 5% NaHCO$_3$ (3×), H$_2$O (3×) then dried over MgSO$_4$, filtered and the solvent evaporated in vacuo. The crude product was chromatographed on flash silica gel eluted with 4:1 hexanes/ethyl acetate. Yield: 181 mg, (0.36 mmol), 36%. MS(CI) m/e 503(m+H)+, 520(m+NH$_4$)+, 447(-56), 403(-100), 312-(-191). $^1$H NMR(CDCl$_3$, 300MHz) δ 1.42(s,9H), 1.90-2.03(m,1H), 2.12-2.23(m,1H), 2.37-2.6(m,2H), 4.21(m,1H), 5.12(s,2H), 5.25(brd,J=7Hz,1H), 6.20(d,J=8Hz,1H), 7.02(brd,J=7Hz,1H), 7.20-7.33(m,15H). C,H,N Analysis calculated for $C_{30}H_{34}N_2O_5$: C 71.69, H 6.82, N 5.58; Found: C 71.46, H 6.89, N 5.58.

EXAMPLE 40

(γ-Benzyl ester)-R-Glu-(diphenylmethyl)amide hydrochloride

Boc-(γ-benzyl ester)-R-Glu-(diphenylmethyl)amide (100 mg, 0.20 mmol) was dissolved in 4 N HCl-dioxane (1.0 mL, 4 mmol) under N$_2$. After 2 hours, the solvent was evaporated. R$_f$0.21 (18:1 CHCl$_3$—EtOH). Product was used directly in the next step. Rf=0.80 (90:10:1, CHCl$_3$—MeOH—NH$_4$OH).

EXAMPLE 41

N-(2'-Indolylcarbonyl)-(γ-benzyl ester)-R-Glu-(diphenylmethyl)amide

EDCI (42.1 mg, 0.22 mmol) was added to a cooled (4° C.) solution of indole-2-carboxylic acid (36 mg, 0.22 mmol), hydrochloride salt of example 40 (0.2 mmol), HOBt (30 mg, 0.22 mmol) and TEA (62 mL, 0.44 mmol) in 4 mL dry CH$_2$Cl$_2$. The reaction was allowed to reach ambient temperature. After 3 days, the reaction mixture was poured into EtOAc and extracted successively with 1 M H$_3$PO$_4$ (3×), 1 M Na$_2$CO$_3$ (3×), H$_2$O (3×), then dried over MgSO$_4$, filtered and evaporated. The crude product was recrystallized from EtOAc. Yield: 73 mg, (0.13 mmol), 67%. R$_f$=0.19 (2:1 hexanes-ethyl acetate). MS(CI) m/e 546(m+)+, 455(-91), 438(-108). $^1$H NMR(CDCl$_3$, 300MHz) δ 9.07(s,1H), 7.66(d,1H), 7.45(d,1H), 7.12-7.41(m,19H), 6.45(m,1H), 6.21(dd,1H,d(+D20),J=7Hz), 5.12(d,J=12Hz,1H), 5.08(d,J=12Hz,1H), 4.72-4.80(m,1H), 2.65-2.76(m,1H), 2.42-2.52(m,1H), 2.15-2.32(m,2H).

EXAMPLE 42

N-(2'-Indolylcarbonyl)-R-Glu-N$^\alpha$-(diphenylmethyl)amide

N-(2'-Indolylcarbonyl)-(γ-benzyl ester)-R-Glu-(diphenylmethyl) amide (60 mg, 0.11 mmol) was dissolved into MeOH (10 mL) and 1 N NaOH (220 μL) was added at room temperature. After 5 hours, an additional 220 μL of 1 N NaOH was added and the reaction was refrigerated for 3 days. The solvent was evaporated in vacuo. The residue in H$_2$O was extracted with EtOAc (3×) then acidified with 6 N HCl and reextracted with EtOAc (3×). The latter EtOAc extractions were combined and washed until neutral to pH paper, then dried over MgSO$_4$ and evaporated in vacuo. The crude product was recrystallized from aqueous ethanol. R$_f$=0.35 (80:20:1 CHCl$_3$—MeOH—NH$_4$OH). mp=224°-5° C. [δ]$_D$= −24.4° (c=0.53, MeOH). MS(FAB+) m/e 456(m+H)+, 911(2m+H)+. $^1$H NMR(CDCl$_3$, 300MHz) δ 1.95-2.07(m,2H), 2.24-2.40(m,2H), 4.62(m,1H), 6.14(d,J=8Hz,1H), 7.03(dt,1H), 7.18(dt,1H), 7.22-7.36(m,11H), 7.43(dd,J=7,≦1Hz,1H), 7.62(d,J=8Hz,1H), 8.02(d,J=7Hz,1H), 8.98(d,J=8Hz,1H), 11.63(s,1H), 12.04(brs,1H). C,H,N Analysis calculated for: C$_{27}$H$_{25}$N$_3$O$_4$ 0.75 H$_2$O: C 69.14, H 5.70, N 8.96; Found: C 69.01, H 5.52, N 8.58.

EXAMPLE 43

Boc-(γ-benzyl ester)-R-Glu-(2'-indanyl)amide

BOPCl (254 mg, 1.0 mmol) was added to a solution of Boc-(γ-benzyl ester)-R-glutamic acid (337 mg, 1.0 mmol), 2-aminoindane (425 mg, 2.5 mmol) and TEA (348 μL, 2.5 mmol) in dry THF at room temperature. The reaction mixture was stirred overnight after which the solvent was removed in vacuo. The residue was dissolved into EtOAc and extracted with 1 M H$_3$PO$_4$ (3×), 1 M Na$_2$CO$_3$ (3×), brine (3×) then dried over MgSO$_4$, filtered and evaporated in vacuo. The crude product was crystallized from hexanes-CHCl$_3$. Yield: 335 mg, (0.69 mmol, 69%). R$_f$=0.26 (2:1 hexanes-ethyl acetate).

EXAMPLE 44

(γ-Benzyl ester)-R-Glu-(2'-indanyl)amide hydrochloride

Boc-(γ-benzyl ester)-R-Glu-2'-indanylamide (300 mg, 0.61 mmol) was dissolved in HCl-dioxane (3 mL, 12 mmol) at room temperature under N$_2$. The solvent was removed after 30 minutes and the crude product was placed under high vacuum overnight.

EXAMPLE 45

N-(2'-Indolylcarbonyl)-(γ-benzyl ester)-Glu-(2,-indanyl)amide

EDCI (124 mg, 0.65 mmol) was added to a solution of indole-2-carboxylic acid (105 mg, 0.65 mmol), hydrochloride salt from example 44 (0.61 mmol assumed), HOBt (88 mg, 0.65 mmol) and TEA (181 μL, 1.3 mmol) in dry CH$_2$Cl$_2$ (10 mL). The reaction was stirred overnight then poured into EtOAc and extracted successively with 1 N H$_3$PO$_4$ (3×), 1 M Na$_2$CO$_3$ (3×), H$_2$O (2×), brine (1×) then dried over MgSO$_4$, filtered and evaporated in vacuo. The crude product was mixed with EtOAc, cooled to −20° C. and filtered. Yield: 235 mg, (0.47 mmol, 78%). R$_f$=0.17 (2:1 hexanes-EtOAc).

EXAMPLE 46

N-(2'-Indolylcarbonyl)-R-Glu-N$^α$-(2'-indanyl)amide

Benzyl ester of example 45 (215 mg, 0.43 mmol) was dissolved into 2:1 MeOH—EtOAc (30 mL) and treated with 10% palladium on carbon (50 mg, prewetted with MeOH under N$_2$) under one atmosphere H$_2$ (balloon). After 2 hours, the catalyst was filtered and the filtrate was evaporated to dryness in vacuo. The crude product was recrystallized from 80% aqueous ethanol. R$_f$ 0.21 (80:20:1 CHCl$_3$—MeOH—NH$_4$OH). mp=184-5° C. [α]$_D$= −60.2° (c=1.13, MeOH). MS(FAB+) m/e 406(m+H)+, 289(−117), 273(−133), 245(−161). $^1$H NMR(DMSO$_{d6}$,300MHz) δ 1.85-2.05(m,2H), 2.22-2.39(m,2H), 2.73-2.85(m,2H), 3.13-3.23(m,2H), 4.40-4.52(m,2H), 7.04(t,J=7Hz,1H), 7.12-7.26(m,6H), 7.42(d,J=9Hz,1) 7.62(d,J=8Hz,1H), 8.38(d,J=7Hz,1H), 8.48(d,J=8Hz,1H), 11.59(s,1H), 12.15(brs,1H). C,H,N Analysis calculated for: C$_{23}$H$_{23}$N$_3$O$_4$: C 68.13, H 5.72, N 10.36; Found: C 67.89, H 5.63, N 10.18.

EXAMPLE 47

Boc-(γ-benzyl ester)-R-Glu-(3'-quinolyl)amide

BOPCl (254 mg, 1.0 mmol) was added to a cooled (4° C.) solution of Boc-(γ-benzyl ester)-R-Glutamic acid (337 mg, 1.0 mmol) and 3-aminoquinoline (361 mg, 2.5 mmol) and TEA (153 μL, 1.1 mmol), in dry THF (15 mL). The reaction was allowed to reach ambient temperature. After 3 days, additional TEA (153 μL) and BOPCl (30 mg) was added and stirring continued for 1 day. The solvent was evaporated in vacuo and the residue, dissolved in EtOAc, was extracted successively with 1 M H$_3$PO$_4$ (3×), 1 M Na$_2$CO$_3$ (3×), brine (3×), then dried over MgSO$_4$, filtered and evaporated. Yield: 344 mg, (0.74 mmol, 74%). R$_f$=0.31 (18:1 CHCl$_3$—EtOH).

EXAMPLE 48

(γ-Benzyl ester)-R-Glu-(3,-quinolyl)amide

Boc-(γ-benzyl ester)-R-Glu-(3'-quinolyl)amide (334 mg, 0.74 mmol) was mixed with HCl-dioxane (3.7 mL, 15 mmol) under an N$_2$ atmosphere at ambient temperature. Additional HCl-Dioxane (3.7 mL) was added after 1 hour. After 2 hours, the solvent was evaporated and the residue was placed under high vacuum overnight. R$_f$=0.10 (18:1 CHCl$_3$—EtOH).

EXAMPLE 49

N-(2'-Indolylcarbonyl)-(γ-benzyl ester)-R-Glu-(3,-quinolyl)amide

EDCI (143 mg, 0.75 mmol) was added to a cooled (4° C.) solution of indole-2-carboxylic acid (121 mg, 0.75 mmol), hydrochloride salt of example 48 (0.74 mmol assumed), HOBt (101 mg, 0.75 mmol), TEA (209 μL, 1.5 mmol) in CH$_2$Cl$_2$ (15 mL). The reaction was allowed to attain ambient temperature overnight. The solvent was evaporated in vacuo and the residue was dissolved in EtOAc and extracted with 1 M H$_3$PO$_4$ (3×), 1 M Na$_2$CO$_3$ (3×), brine (3×) then dried over MgSO$_4$, filtered and the solvent evaporated in vacuo. The crude product was recrystallized from EtOAc-hexanes to give: 174 mg, (0.34 mmol) 46%. R$_f$=0.22 (1:2 hexanes-EtOAc). mp=175-7° C. [α]$_D$= −3.7° (c=0.83, MeOH). MS(CI) m/e 507(m+H)+, 399(−108), 272(−235), 256(−251). $^1$H NMR(CDCl$_3$,300 MHz) δ 2.32-2.41(m,2H), 2.58-2.68(m,1H), 2.33-2.43(m,1H), 4.89(brq,1H), 5.12(d,J=14Hz,1H), 5.17(d,J=14Hz,1H), 7.08(d,J<1Hz,1H), 7.13(dt,1H), 7.26(s,1H), 7.30(s,5H), 7.41(d,J=8Hz,1H), 7.48(dt,J=1,8Hz,1H), 7.60(dt,J=1,7Hz,1H), 7.68(brt,J=9Hz,1H), 7.82(d,J=7Hz,1H), 8.02(d,J=8Hz,1H), 8.66(d,J=2Hz,1H), 8.79(d,J=2Hz,1H), 9.37(s,1H), 9.54(s,1H). C,H,N Analysis calculated for C$_{30}$H$_{26}$N$_4$O$_4$ H$_2$O: C 69.89, H 5.28, N 10.87; Found: C 69.78, H 5.22, N 10.88.

EXAMPLE 50

N-(2'-Indolylcarbonyl)-R-Glu-$N^\alpha$-(3,-quinolyl)amide

N-(2'-Indolylcarbonyl)-(γ-benzyl ester)-R-Glu-(3'-quinolyl)amide (150 mg, 0.30 mmol) was dissolved in MeOH (10 mL) and then treated with 5% palladium on barium sulfate (Pd/BaSO$_4$) (50 mg) under 1 atmosphere H$_2$ (balloon). After 4 hours, the catalyst was removed by filtration and the solvent was evaporated in vacuo. The crude product was recrystallized from aqueous methanol to give: 69 mg, (0.16 mmol, 55%). $[\alpha]_D = -43.8°$ (c=1.04, 1:1 DMF-MeOH). MS(FAB+) m/e 417(m+H)$^+$, 307(−110), 277(140), 257(−160). $^1$H NMR(DMSO$_{d6}$,300MHz) δ 2.03−2.25(m,2H), 2.35−2.5(m,2H), 4.68(m,1H;dd(D$_2$O),J=5,9Hz), 7.05(dt,J=1,7Hz,1H), 7.20(dt,J=1,7Hz,1H), 7.32(d,J=1Hz,1H), 7.43(d,J=8Hz,1H), 7.58(dt,J=1,8Hz,1H), 7.63−7.68(m,2H), 7.95(dt,J=1,9Hz,2H), 8.72(d,J=2Hz,1H), 8.74(d,J=8Hz,1H), 8.97(d,J=2Hz,1H), 10.16(s,1H), 11.12(brs,1H), 12.23(brs,1H). C,H,N Analysis calculated for C$_{23}$H$_{20}$N$_4$O$_4$ H$_2$O: C 65.63, H 4.90, N 13.31; Found: C 65.84, H 4.93, N 13.14.

EXAMPLE 51

Boc-(γ-benzyl ester)-R-Glu-(1'-adamantyl)amide

BOPCl (254 mg, 1.0 mmol) was added to a cooled solution (4° C.) of Boc-(γ-benzyl ester)-R-Glutamic acid (337 mg, 1.0 mmol), 1-aminoadamantane (378.3 mg, 2.5 mmol), and TEA (153 μL, 1.1 mmol) in dry THF (15 mL). The reaction was allowed to reach ambient temperature overnight. The solvent was evaporated in vacuo and the residue, dissolved in ethyl acetate, was extracted successively with 1 M H$_3$PO$_4$ (3×), 1 M Na$_2$CO$_3$ (3×), brine (3×) then dried over MgSO$_4$, filtered and evaporated in vacuo. Yield: 276 mg, (0.59 mmol, 59%). R$_f$=0.75 (2:1 hexanes-EtOAc). MS(CI) m/e 471(m+H)$^+$, 415(−56), 387(−84), 370(−101). $^1$H NMR(CDCl$_3$,300MHz) δ 7.33−7.38(m,5H), 5.78(s,1H), 5.22(bdd, J=2,7Hz,1H), 5.12(s,2H), 4.36−4.49(m,1H), 3.91−4.12(m,2H), 2.37−2.59(m,2H), 2.05−2 12(m,6H), 1.96(bd,J=2Hz,7H), 1.82−1.92(m,1H), 1.64−1.68(m,9H).

EXAMPLE 52

(γ-Benzyl ester)-R-Glu-(1,-adamantyl)amide hydrochloride

Boc-(γ-benzyl ester)-R-Glu-(1'-adamantyl)amide (276 mg, 0.59 mmol) was mixed with HCl-dioxane (3.0 mL, 12 mmol) under an N$_2$ atmosphere at ambient temperature. After 30 minutes, the solvent was evaporated and the residue was placed under high vacuum overnight. R$_f$=0.70 (80:20:1 CHCl$_3$—MeOH—NH$_4$OH).

EXAMPLE 53

N-(2'-Indolylcarbonyl)-(γ-benzyl ester)-R-Glu-(1'-adamatyl)amide

EDCI (115 mg, 0.6 mmol) was added to a cooled (4° C.) solution of indole-2-carboxylic acid (97 mg, 0.60 mmol), hydrochloride salt of example 52 (0.59 mmol assumed), HOBt (81 mg, 0.6 mmol), and TEA (132 μL, 1.2 mmol) in CH$_2$Cl$_2$ (10 mL). The reaction was allowed to attain ambient temperature overnight. The solvent was evaporated and the residue was dissolved in EtOAc and extracted with 1 M H$_3$PO$_4$ (3×), 1 M Na$_2$CO$_3$ (3×), brine (3×). The crude product was chromatographed on flash silica gel eluted with a step gradient of 4:1 to 2:1 hexanes-ethyl acetate. Yield: 179 mg, (0.35 mmol), 59%. R$_f$=0.24 (2:1 hexanes-ethyl acetate).

EXAMPLE 54

N-(2'-Indolylcarbonyl)-R-Glu-$N^\alpha$-(1,-adamantyl)amide

N-(2'-Indolylcarbonyl)-(γ-benzylester)-R-Glu-(1'-adamantyl)amide (176 mg, 0.35 mmol) was dissolved in MeOH (10 mL) and then treated with 5% Pd/BaSO$_4$ (100 mg) under H$_2$ atmosphere (balloon). After 3 hours, the catalyst was removed by filtration and the solvent was evaporated in vacuo. The crude product was recrystallized from aqueous methanol to give: 117 mg, (0.28 mmol, 79%). $[\alpha]_D = -11.6°$ (c=0.98, MeOH). MS(FAB+') m/e 424(m+H)$^+$, 408(−16), 273(−151), 246(−178). $^1$H NMR(DMSO$_{d6}$,300 MHz) δ 1.62(brs,6H), 1.93(brs,7H), 2.01(brs,4H), 2.26−2.42(m,2H), 4.43(m,1H,+D$_2$O:dd,J=6,8Hz), 7.03(dt,J=8Hz,1), 7.19(dt,J=1,7Hz,1H), 7.23(d,J=2Hz,1H), 7.42(d,J=8Hz,1H), 7.45(s,1H), 7.52(d,J=8Hz,1H), 8.33(d,J=8Hz,1), 11.11(brs,1H), 12.17(brs,1H). C,H,N Analysis calculated for C$_{24}$H$_{29}$N$_3$O$_4$ H$_2$O: C 67.35, H 6.95, N 9.82; Found: C 67.12, H 6.97, N 9.73.

EXAMPLE 55

Boc-(γ-benzyl ester)-R-Glu-(1',2'-diphenylethyl)amide

BOPCl (254 mg, 1.0 mmol) was added to a cooled solution (4° C.) of Boc-(γ-benzyl ester)-R-Glutamic acid (337 mg, 1.0 mmol), 1,2-diphenylethylamine (484 μL, 2.5 mmol), and TEA (153 μL, 1.1 mmol) in dry THF (15 mL). The reaction was allowed to reach ambient temperature overnight. After 3 days, the solvent was evaporated in vacuo and the residue, dissolved in ethyl acetate, was extracted successively with 1 M H$_3$PO$_4$ (3×), 1 M Na$_2$CO$_3$ (3×), brine (3×) then dried over MgSO$_4$, filtered and evaporated in vacuo. The crude product was recrystallized from hexanes-ethyl acetate. Yield: 277 mg, (0.54 mmol, 54%). R$_f$=0.46 (2:1 hexanes-ethyl acetate).

EXAMPLE 56

(γ-Benzyl ester)-R-Glu-(1',2'-diphenylethyl)amide hydrochloride

Boc-(γ-benzyl ester)-R-Glu-(1,2'-diphenylethyl)amide (247 mg, 0.48 mmol) was mixed with HCl-dioxane (2.5 mL, 10 mmol) under an N$_2$ atmosphere at ambient temperature. After 1 hour, the solvent was evaporated and the residue was placed under high vacuum overnight. R$_f$=0.63, 0.69 (90:10:1 CHCl$_3$—MeOH—NH$_4$OH).

EXAMPLE 57

N-(2'-Indolylcarbonyl)-(γ-benzyl ester)-R-Glu-(1',2'-diphenylethyl)amide

EDCI (95 mg, 0.48 mmol) was added to a cooled (4° C.) solution of indole-2-carboxylic acid (77 mg, 0.48 mmol), hydrochloride salt of example 56 (0.48 mmol assumed), HOBt (65 mg, 0.48 mmol), and TEA (139 μL, 1.0 mmol) in anhydrous CH$_2$Cl$_2$ (10 mL). The reaction was allowed to attain ambient temperature overnight. After 3 days, the solvent was evaporated and the residue, dissolved in EtOAc, was extracted with 1 M H$_3$PO$_4$ (3×), 1 M Na$_2$CO$_3$ (3×), brine (3×) then dried over MgSO$_4$, filtered and the solvent evaporated in vacuo. Yield: 253 mg, (0.45 mmol, 94%). R$_f$=0.20 (2:1 hexanes—EtOAc). MS(FAB+) m/e 560(m+H)+, 363(−197).

EXAMPLE 58

N-(2,-Indolylcarbonyl)-R-Glu-N$^\alpha$-(1',2'-diphenylethyl)amide

N-(2,-Indolylcarbonyl)-($\gamma$-benzyl ester)-R-Glu-(1',2'-diphenyl ethyl)amide (176 mg, 0.35 mmol) was dissolved in MeOH (50 mL) with warming and, after returning to ambient temperature, was evaporated in vacuo and the residue, dissolved in EtOAc, was extracted with 1 M H$_3$PO$_4$ (3×), brine (3×) then dried over MgSO$_4$, filtered and the solvent evaporated in vacuo. The tlc indicated two slightly resolved spots were present (18:1 CHCl$_3$—EtOH). The crude product was chromatographed on flash silica gel eluted with 18:1 CHCl$_3$—EtOH to give 71 mg, (0.15 mmol, 54%). A small amount of each isomer was isolated pure and MS(FAB+) showed them to be methyl esters. The combined product was redissolved in MeOH and again treated with 1 N NaOH (0.5 mL, 0.5 mmol) until both methyl esters were consumed (determined by tlc as above). The solvent was then evaporated in vacuo and the residue, dissolved in H$_2$O, was acidified with 6 N HCl and extracted into EtOAc (3×). The combined layers were washed with H$_2$O until neutral to pH paper then dried over MgSO$_4$, filtered and evaporated in vacuo. The crude product was chromatographed by Prep HPLC (C18 column; with a gradient of 25–80% CH$_3$CN over 10 minutes with 0.05 M NH$_4$OAc, pH 4.5, as the aqueous buffer). [$\alpha$]D = +7.5° (c=1.07, DMF). mp=218–219.5° C. MS(FAB+) m/e 470(m+H)+, 284(−186), 273(−197). $^1$H NMR(CD$_3$OD,300MHz): $\delta$ (1:1 mixture of diastereomers) 1.8–2.1(m,2H), 2.14–2.21(m,1H), 2.31(t,J=7Hz,1H), 2.95–3.18(m,2H), 4.06–4.14(m,1H), 5.15(t,J=7Hz,0.5H), 5.22(dd,J=5,10Hz,0.5H), 6.98–7.47(m,14H), 7.08(d,J=7Hz,0.5H), 7.63(d,J=7Hz,0.5H). C,H,N Analysis calculated for C$_{28}$H$_{27}$N$_3$O$_4$ 1.5 H$_2$O: C 67.73, H 6.09, N 8.46; Found: C 67.59, H 5.77, N 8.32.

EXAMPLE 59

N-(N$^i$-Methyl-2'-Indolylcarbonyl)-($\gamma$-benzyl ester)-R-Glu-di-n-pentylamide EDCI (96 mg, 0.50 mmol) was added to a cooled (4° C.) solution on N-methylindole-2-carboxylic acid (88 mg, 0.50 mmol), hydrochloride salt of example 2 (206 mg, 0.50 mmol), HOBt (68 mg, 0.50 mmol), and TEA (140 $\mu$L, 1.0 mmol) in CH$_2$Cl$_2$ (15 mL). The reaction was allowed to attain ambient temperature overnight. The solvent was evaporated and the residue was dissolved in EtOAc and extracted with 1 M H$_3$PO$_4$ (3×), 1 M Na$_2$CO$_3$ (3×), brine (3×) then dried over MgSO$_4$, filtered and the solvent evaporated in vacuo. Yield: 262 mg, (0.49 mmol, 98%). R$_f$=0.86 (18:1 CHCl$_3$—EtOH).

EXAMPLE 60

N-(N$^i$-Methyl-2,-Indolylcarbonyl)-R-Glu-N$^\alpha$,N$^\alpha$-dipentylamide The benzyl ester of example 59 (245 mg, 0.46 mmol) was dissolved in MeOH (20 mL) and then treated with 5% Pd/BaSO$_4$ (50 mg) under 1 atmosphere H$_2$ (balloon). After 2 hours, the catalyst was removed by filtration and the solvent was evaporated in vacuo. The crude product was dried under high vacuum overnight. R$_f$=0.42 (80:20:1 CHCl$_3$—MeOH—NH$_4$OH).

mp=132°–133° C. [$\alpha$]$_D$+8.4° (c=1.09, MeOH). MS(FAB+) m/e 444(m+H)+, 287(−157), 269(−175), 259(−185). $^1$H NMR(DMSO$_{d6}$,300MHz) $\delta$ 0.83–0.87(m,6H), 1.17–1.33(m,8H), 1.41–1.52(m,2H), 1.52–1.70(brm,2H), 1.85–1.94(brm,1H), 2.36(t,J=7Hz,2H), 3.08(quintet,1H), 3.25–3.50(m,3H), 3.96(s,3H), 4.87(m,1H), 7.11(t,J=7Hz,1H), 7.22(s,1H), 7.28(dt,J=1,7Hz,1H), 7.52(d,J=8Hz,1H), 7.64(d,J=8Hz,1H), 8.54(d,J=8Hz,1H), 12.20(bs,1H). C,H,N Analysis calculated for C$_{25}$H$_{37}$N$_3$O$_4$: C 67.69, H 8.41, N 9.47; Found: C 67.52, H 8.34, N 9.43.

EXAMPLE 61

Boc-($\gamma$-benzyl ester)-R-Glu-(9'-fluorenyl)amide

BOPCl (254 mg, 1.0 mmol) was added to a cooled solution (4° C.) of Boc-($\gamma$-benzyl ester)-R-Glutamic acid (337 mg, 1.0 mmol), 9-aminofluorene (453 mg, 2.5 mmol), and TEA (153 $\mu$L, 1.1 mmol) in dry THF (15 mL). The reaction was allowed to reach ambient temperature overnight after which additional BOPCl (50 mg) and TEA (30 $\mu$L) were added. After several hours, the solvent was evaporated in vacuo and the residue was dissolved in EtOAc and extracted successively with 1 M H$_3$PO$_4$ (3×), 1 M Na$_2$CO$_3$ (3×), brine (3×) then dried over MgSO$_4$, filtered and evaporated in vacuo. The crude product was reprecipitated from hexanes-ethyl acetate Yield: 163 mg, (0.33 mmol, 33%). R$_f$=0.41 (2:1 hexanes—EtOAc). MS(CI) m/e 501(m+H)+, 445(−56), 401(−100). $^1$H NMR(CDCl$_3$,300MHz) $\delta$ 7.70(d,J=7Hz,2H), 7.52(d,J=7Hz,2H), 7.40(t,J=7Hz,2H), 7.26–7.32(m,9H), 6.40(bd,J=8Hz,1H), 6.18(d,J=8Hz,1H), 5.32(bd,J=6Hz,1H), 5.10(s,2H), 4.18–4.27(m,1H), 2.45–2.67(m,2H), 2.18–2.30(m,1H), 1.98–2.10 (m,1H), 1.49(s,9H).

EXAMPLE 62

($\gamma$-Benzyl ester)-R-Glu-(9'-fluorenyl)amide hydrochloride

Boc-($\gamma$-benzyl ester)-R-Glu-(9,-fluorenyl)amide (158 mg, 0.32 mmol) was mixed with HCl-dioxane (2.0 mL, 8.0 mmol) under an N$_2$ atmosphere at ambient temperature. After 90 minutes, the product was precipitated with the addition of ether and the resulting solid collected and dried in vacuo. Yield: 133 mg, (0.31 mmol, 97%). R$_f$=0.10 (100:60:18:33 EtOAc-pyridine-acetic cid-H$_2$O).

EXAMPLE 63

N-(2'-Indolylcarbonyl)-($\gamma$-benzyl ester)-R-Glu-(9'-fluorenyl)amide

EDCI (69 mg, 0.35 mmol) was added to a cooled (4° C.) solution of indole-2-carboxylic acid (56 mg, 0.35 mmol), hydrochloride salt from example 62 (133 mg, 0.31 mmol), HOBt (47 mg, 0.35 mmol) and TEA (98 $\mu$L, 0.7 mmol) in CH$_2$Cl$_2$ (10 mL). The reaction was allowed to attain ambient temperature overnight. The solvent was evaporated and the residue was dissolved in ethyl acetate and extracted with 1 M H$_3$PO$_4$ (3×), 1 M Na$_2$CO$_3$ (3×), brine (3×). The crude product was recrystallized from ethyl acetate to give: 115 mg, (0.119 mmol), 57%. R$_f$=0.62 (1:1 hexanes-ethyl acetate).

EXAMPLE 64

N-(2'-Indolylcarbonyl)-R-Glu-N$^\alpha$-(9'-fluorenyl)amide

N-(2,-Indolylcarbonyl)-($\gamma$-benzyl ester)-R-Glu-(9'-fluorenyl) amide (104 mg, 0.18 mmol) was dissolved in 3:1 MeOH—EtOAc (20 mL) and then treated with 5% Pd/BaSO$_4$ (50 mg) under 1 atmosphere H$_2$ (balloon) overnight. The catalyst was removed by filtration and the solvent was evaporated in vacuo. The crude product was recrystallized from aqueous ethanol. R$_f$=0.15 (80:20:1 CHCl$_3$—MeOH—NH$_4$OH). mp=265-8° C. [$\alpha$]$_D$= -35.2° (c=1.07, 1:1 DMF—MeOH). MS(CI) m/e 454(m+H)$^+$, 436(-18), 273(-181). $^1$H NMR(DMSO$_{d6}$,300MHz) $\delta$ 1.98-2.17(m,2H), 2.37-2.44(m,2H), 4.52(brq,1H,+D$_2$O: dd,J=5,8Hz), 6.05(d,J=8Hz,1H), 7.04(t,J=7Hz,1H), 7.19(t,J=7Hz,1H), 7.27(d,J=1Hz,1H), 7.33(d,J=7Hz,2H), 7.40-7.52(m,5H), 7.62(d,J=8Hz,1H), 7.36(d,J=7Hz,2H), 8.53(d,J=7Hz,1H), 8.70(d,J=8Hz,1H), 11.63(brs,1H). C,H,N Analysis calculated for: C$_{27}$H$_{23}$N$_3$O$_4$ H$_2$O: C 70.12, H 5.23, N 9.09; Found: C 70.17, H 5.17, N 9.05.

EXAMPLE 65

Cbz-($\gamma$-benzyl ester)-R-Glu-(1',3'-diphneyl-5'-pyrazyl)maide

Phosphorous pentachloride (PCl$_5$) (208 mg, 1.0 mmol) was added in one portion to a solution of Cbz-($\gamma$-benzyl ester)-R-Glutamic acid (371 mg, 1.0 mmol) in CH$_2$Cl$_2$(10 mL) at -20° C. After 20 minutes, 1,3-diphenyl-5-aminopyrazole (588 mg, 2.5 mmol) was added and the temperature was raised to 0° C. for 2 hours. The reaction mixture was poured into ethyl acetate and extracted successively with 1 N H$_3$PO$_4$(3$\times$), 1 M Na$_2$CO$_3$ (3$\times$), and H$_2$O (3$\times$) then dried over MgSO$_4$, filtered and the solvent evaporated in vacuo. The residue was chromatographed on flash silica eluted with a stepped gradient from 4:1 to 2:1 hexanes-ethyl acetate. Yield: 555 mg, (0.94 mmol, 74%). R$_f$=0.31 (2:1 hexanes-ethyl acetate). $^1$H NMR(CDCl$_3$,300MHz) $\delta$ 8.69(bs,1H), 7.87(dd, J~<1,7Hz,2H), 7.30-7.50(m,18H), 7.05(s,1H), 5.66(bd,J=7Hz,1H), 5.02-5.11(m,4H), 4.28-4.34(m,1H), 2.58-2.68(m,1H), 2.41-2.52(m,1H), 2.16-2.26(m,1H), 1.94-2.06(m,1H).

EXAMPLE 66

R-Glu-N$^\alpha$-(1',3'-diphenyl-5'-pyrazyl)amide

Cbz-($\gamma$-benzyl ester)-R-Glu-(1',3'-diphenyl-5'-pyrazyl)amide (417 mg, 0.70 mmol) and 10% Pd/C (100 mg, prewetted with MeOH under an N$_2$ atmosphere) were combined in ethanol (100 mL) under 1 atmosphere H$_2$ (balloon) overnight. The mixture was then filtered and rinsed with fresh solvent. Evaporation gave the deprotected product (260 mg, 0.70 mmol, quantitative). R$_f$=0.23 (8:1:1 butanol-AcOH—H$_2$O). The product was used directly in the next step.

EXAMPLE 67

N-(2-Indolylcarbonyl)-R-Glu-N$^\alpha$-(1',3'-diphenyl-5'-pyrazyl)amide

2-Indolecarboxy-2,4,6-trichlorophenyl ester (255 mg, 0.75 mmol) and R-Glu-(1',3'-diphenyl-5'-pyrazyl)amide (260 mg, 0.70 mmol) were dissolved in dry ethyl acetate (15 mL) and TEA (209 $\mu$L, 1.5 mmol) was added at room temperature. After one day, additional TEA (209 $\mu$L) was added. After 4 days, the reaction was diluted with ethyl acetate and then extracted successively with 1 M H$_3$PO$_4$(3$\times$), H$_2$O (3$\times$) and brine (1$\times$) then dried over MgSO$_4$, filtered and evaporated in vacuo. The residue was recrystallized from aqueous ethanol to give: 130 mg, (0.26 mmol, 36%). mp=261-5° C.(dec). [$\alpha$]$_D$= -0.3° (c=1.09, 1:1 DMF-MeOH). MS(FAB+) m/e 508(m+H)$^+$, 365(-143), 290(-218), 262(-216), 236(-272). $^1$H NMR(DMSO$_{d6}$,300MHz) $\delta$ 1.92-2.12(m,2H), 2.33(brt,J=7Hz,2H), 4.58(m 1H, dd(+D$_2$O),J~5,9Hz), 6.92(s,1H), 7.06(dt,J=1,8Hz,1H), 7.21(dt,J=1,7Hz,1H), 7.28(brs,1H), 7.35(brt,2H), 7.42-7.47(m,6H), 7.63(t,J=8Hz,3H), 7.37(d,J=7Hz,2H), 8.78(brd,J=6Hz,1H), 10.28(s,1H), 11.63(s,1H). C,H,N Analysis calculated for C$_{29}$H$_{25}$N$_5$O$_4$ H$_2$O: C 67.43; H 5.07, N 13.56; Found: C 67.69, H 5.13, N 13.40.

EXAMPLE 68

Boc-($\gamma$-benzyl ester)-R-Glu-($\alpha,\alpha$-dimethyl-$\beta$-phenylethyl)amide To a solution of Boc-($\gamma$-benzyl ester)-R-Glutamic acid (337 mg, 1.0 mmol) and $\alpha,\alpha$-dimethyl-$\beta$-phenyl ethylamine (373 mg, 2.5 mmol) in dry THF (15 mL) was added BOPCl (254 mg, 1.0 mmol) and TEA (1.1 mmol) and the reaction was stirred for 3 days. After evaporation of the solvent in vacuo, the residue was dissolved in ethyl acetate and extracted successively with 1 M H$_3$PO$_4$(3$\times$) 5% NaHCO$_3$(3$\times$), brine (3$\times$), then dried over MgSO$_4$, filtered and the solvent evaporated in vacuo. The oily residue was chromatographed on flash silica gel eluted with 4:1 hexane-ethyl acetate to yield: 303 mg, (0.65 mmol, 65%) as a colorless oil. R$_f$=0.46 (2:1 hexanes-ethyl acetate). MS(CI) m/e 469(m+H)$^+$, 413(-56), 369(-100), 278(-191). $^1$H NMR(CDCl$_3$,300MHz) $\delta$ 1.28(s,3H), 1.33(s,3H), 1.42(s,9H), 1.82-1.94(m,1H), 2.03-2.16(m,1H), 2.35-2.54(m,2H), 2.96(d,J=13Hz,1H), 3.07(d,J=13Hz,1H), 4.00(m,1H), 5.12(s,2H), 5.18(brd,1H), 5.80(s,1H), 7.12(dd,J=3,7Hz,2H), 7.2-7.28(m,3H), 7.35(s,5H).

EXAMPLE 69

($\gamma$-Benzyl ester)-R-Glu-($\alpha,\alpha$-dimethyl-$\beta$-phenylethyl)amide hydrochloride The Boc protected material of example 68 (260 mg, 0.56 mmol) was treated with HCl-dioxane (3 mL, 12 mmol) precooled in an ice bath. An additional 2 mL of HCl-dioxane was added after 2 hours and again at 3 hours at room temperature. After 3.5 hours, the solvent was evaporated and the residue was used directly. MS(CI) m/e 369(m+H)$^+$, 351(-18), 277(-92), 236(-133), 192 (-177). R$_f$=0.85 (80:20:1 CHCl$_3$—MeOH—NH$_4$OH), 0.46 (100:60:18:33 EtOAc-pyridine-HOAc-H$_2$O).

EXAMPLE 70

N-(2'-Indolylcarbonyl)-($\gamma$-benzyl ester)-R-Glu-($\alpha,\alpha$-dimethyl-$\beta$-phenylethyl)amide EDCI (115 mg, 0.6 mmol) was added to a solution of hydrochloride salt of example 69 (0.56 mmol assumed), indole-2-carboxylic acid (97 mg, 0.6 mmol), HOBt (81 mg, 0.6 mmol) and TEA (167 $\mu$L, 1.2 mmol) in CH$_2$Cl$_2$ (10 mL) cooled to 4° C. in an ice bath. The reaction was allowed to warm to ambient temperature overnight. The solvent was evaporated and the residue dissolved in ethyl acetate. This solution was extracted with portions of 1 M H₃PO₄, 1 M Na₂CO₃, H₂O, then dried over MgSO₄, filtered and the solvent evaporated. The residue was chromatographed on flash silica gel and eluted with 2:1 hexane-ethyl acetate to give 164 mg, (0.32 mmol, 57%). R$_f$=0.27 (2:1 hexanes-ethyl acetate).

EXAMPLE 71

N-(2'-Indolylcarbonyl)-R-Glu-N$^\alpha$-(α,α-dimethyl-β-phenethyl)amide

The benzyl ester of example 70 (164 mg, 0.32 mmol) was treated with 10% Pd/C (50 mg), prewetted with MeOH under an N₂ atm) in 10 mL MeOH under 1 atmosphere H₂ (balloon) for 1 hour. After filtration of the catalyst, the solvent was evaporated in vacuo. The residue was recrystallized from hot 80% aqueous ethanol to give 101 mg, (0.24 mmol 75% yield). mp=109°-114° C. [α]$_D$= −38.0° (c=0.70, MeOH). MS(FAB+) m/e 422(m+H)⁺, 273(−149), 245(−177). ¹H NMR(DMSO$_{d6}$,300MHz) δ 1.18(s,3H), 1.26(s,3H), 1.85-2.05(m,2H), 2.21-2.40(m,2H), 2.90(d,J=13Hz,1H), 3.07(d,J=13Hz,1H), 4.44(m,1H,dd,+(D20), J=6,9Hz), 7.05(dt,1H), 7.11-7.22(m,6H), 7.28(brs,1H), 7.41(s,1H), 7.44(d,J=8Hz,1H), 7.6 (d,J=8Hz,1H), 8.44(d,1H), 11.63(brs,1H), 12.18(brs,1H). C,H,N Analysis calculated for C₂₄H₂₇N₃O₄ 0.1 H₂O: C 64.92, H 6.70, N 9.46; Found: C 64.72, H 6.50, N 9.37.

EXAMPLE 72

N-Cbz-(γ-benzyl ester)-R-Glu-diphenylamide

PCl₅ (208 mg, 1.0 mmol) was added in one portion to a solution of Cbz(γ-benzyl ester)-R-Glutamic acid (371.4 mg, 1.0 mmol) in CH₂Cl₂ (10 mL) at −20° C. After 20 minutes, diphenylamine (423 mg, 2.5 mmol) was added and the temperature was raised to 0° C. for 2 hours. The reaction mixture was poured into ethyl acetate and extracted successively with 1 N HCl(3×), 1 M Na₂CO₃(3×), and H₂O(3×) then dried over MgSO₄, filtered and the solvent evaporated in vacuo. The residue was chromatographed on flash silica eluted with a stepped gradient from 4:1 to 2:1 hexanes-ethyl acetate. Yield: 405 mg, (0.77 mmol, 77%). R$_f$=0.31 (2:1 hexanes-ethyl acetate). MS(CI) m/e 522(m+H)⁺, 540(m+NH₄)⁺. ¹H NMR(CDCl₃,300MHz) δ 1.84-2.12(m,2H), 2.24-2.47(m,2H), 4.63(m,1H), 5.05(s,2H), 5.08(brs,2H), 5.60(d,J=8Hz,1H), 7.2-7.5(m,20H).

EXAMPLE 73

R-Glu-N$^\alpha$,N$^\alpha$-diphenylamide

Cbz-(γ-benzyl ester)-R-Glu-diphenyl amide (400 mg, 0.77 mmol) and 10% Pd/C (50 mg, prewetted with MeOH under an N₂ atmosphere) were combined in MeOH (15 mL) under 1 atmosphere H₂ (balloon) for 3 hours. The catalyst was then filtered and rinsed with fresh solvent. Evaporation gave the deprotected product (244 mg, 0.75 mmol, 98%). R$_f$=0.13 (80:20:1 CHCl₃—MeOH—NH₄OH). The product was used directly in the next step.

EXAMPLE 74

N-(2'-Indolylcarbonyl)-R-Glu-N$^\alpha$,N$^\alpha$-diphenylamide

2-Indolecarboxy-2,4,6-trichlorophenyl ester (29 mg, 0.084 mmol) and R-Glu-diphenyl amide (25 mg, 0.084 mmol) were dissolved in dry THF (4 mL) and TEA (22 μL, 0.16 mmol) was added at room temperature. The tlc at 3 hours showed no reaction and an additional 22 μL TEA was added. After 2 days, the THF was evaporated in vacuo and the residue, dissolved in ethyl acetate, was extracted successively with 1 M H₃PO₄(3×), H₂O(3×) and brine (1×) then dried over MgSO₄, filtered and evaporated in vacuo. The crude product was recrystallized from hot ethyl acetate-hexanes to give 12.1 mg, (0.027 mmol, 33% yield). R$_f$=0.14 (80:20:1 CHCl₃—MeOH—NH₄OH) MS(FAB+) m/e 442(m+H)⁻, 273(−168), 245(−196). ¹H NMR(CDCl₃—CD₃OD,300MHz) δ 2.03-2.20(m,2H), 2.38(dd,J=8,15Hz, 2H), 5.02(dd,J=5,8Hz,1H), 7.1(dJ<1Hz,1H), 7.13(d,J=7Hz,1H), 7.25-7.48(m,12H), 7.66(d,J=8Hz,1H). C,H,N Analysis calculated for C₂₆H₂₃N₃O₄ EtOAc: C 69.96, H 5.44, N 9.07; Found: C 69.72, H 5.57, N 8.90.

EXAMPLE 75

N-(3-(3,-Pyridyl)acryloyl)-(γ-benzyl ester)-R-Glu-N$^\alpha$,N$^\alpha$-di-n-pentylamide Hydrochloride salt (0.23 g, 0.56 mmol) of example 2, EDCI 0.12 g, 0.6 mmol); HOBt (0.075 g, 0.56 mmol) and 3-(3-pyridyl)acrylic acid (0.085 g, 0.56 mmol) were stirred at 0° C. under nitrogen in 10 mL of CH₂Cl₂). To this mixture was added NMM (0.12 mL, 1.1 mmol). The reaction mixture was stirred overnight and permitted to reach ambient temperature. The reaction mixture was poured into ethyl acetate and extracted twice with portions of 1.0 N hydrochloric acid, and once with saturated sodium bicarbonate solution. The organic solution was dried over magnesium sulfate and filtered. Evaporation of the volatiles in vacuo provided a residue which was purified by chromatography using ethyl acetate/hexane as the elutant provided 0.22 g (78% yield) of product. MS(CI) m/e 508(m+H)⁺. 1H NMR(CDCl₃,300MHz) δ 0.85-0.96(m,6H), 1.19-1.42(m,8H), 1.48-1.70(m,4H), 1.78-1.95(m,2H), 2.40-2.60(m,2H), 5.13(m,3H), 5.02(d,J=15Hz,1H), 6.98(d,J=9Hz,1H), 7.35(m,6H), 7.6(d,J=15Hz,1H), 7.80(d,J=9Hz,1H), 8.56(dd,J=1,6Hz,1H), 8.72(d,J=3Hz,1H).

EXAMPLE 76

N-(8,-Quinolylsulfonyl)-(γ-benzyl ester)-R-Glu-di-n-pentyl amide

To a mixture of hydrochloride salt (1.0 mmol) of example 2 and triethylamine (2.0 mmol) stirring in 10 mL of methylene chloride at 0° C. was added 8-quinolylsulfonyl chloride (1.0 mmol). The reaction mixture was allowed to warm to ambient temperature and continue stirring overnight. The reaction mixture was poured into ethyl acetate and extracted with 1.0 N hydrochloric acid and saturated sodium bicarbonate solution. The mixture was dried over magnesium sulfate and filtered. Evaporation of the volatiles in vacuo and chromatography of the residue provided product.

EXAMPLE 77

N-(8'-Quinolylsulfonyl)-R-Glu-N$^\alpha$,N$^\alpha$-di-n-pentyl amide

The product of example 76 was treated with sodium hydroxide solution in methanol as in example 29. Extraction of the acidified solution numerous times with ethyl acetate and subsequent drying, filtration, concentration, and trituration as in example 29 provided product.

EXAMPLE 78

Ethyl N-(t-Butyloxycarbonyl)-(γ-benzyl ester)-R-Glutamyl (N-benzyl)glycinate N-(t-Butyloxycarbonyl)-(γ-benzyl ester)-R-glutamic acid (5.17 grams, 15.3 mmol) and N-benzylglycine ethyl ester (9.12 grams, 47.2 mmol) were stirred in 100 mL of $CH_2Cl_2$ at $-10°$ to $0°$ C. under nitrogen. To this solution was added BOPCl (4.17 grams, 16.4 mmol) and the reaction mixture allowed to slowly warm to room temperature overnight. The mixture was taken up in ethyl acetate and extracted three times with dilute hydrochloric acid, once with saturated sodium bicarbonate solution and dried over magnesium sulfate. The solution was filtered and concentrated in vacuo. The residue was purified by chromatography using ethyl acetate and hexane as elutants to provide 6.59 grams of pure product (84% yield). MS(CI) m/e 513(m+H)+, 322, 305, 276. $^1H$ NMR(CDCl$_3$,300MHz) δ 7.25–7.40 (m,8H), 7.18–7.25(m,2H), 5.36(m,2H), 5.10(m,2H), 4.95(bd,J=15Hz,1H), 4.53(bd,J=15Hz,1H), 4.15(m,2.5H), 3.70(d,J=17Hz,0.5H), 2.40–2.60(m,2H), 2.20(m,1H), 1.82(m,1H), 1.43(bs,9H), 1.23(m,3H).

EXAMPLE 79

Ethyl (γ-benzyl ester)-R-Glutamyl(N-benzyl)glycinate hydrochloride

The ethyl ester product of example 78 (3.46 grams, 6.76 mmol) was stirred at 5° C. in 10 mL of 4.5 N hydrochloric acid in dioxane. When the reaction was complete by tlc, diethyl ether was added and the solvents removed in vacuo. The product was collected via filtration using diethyl ether. Yield 2.96 grams (97%). MS(FAB) m/e 413(m+H)+, 395, 378, 323, 305, 289. $^1H$ NMR(DMSO$_{d6}$,300MHz) δ 8.38(bs,1H), 7.25–7.40(m,10H), 5.11(bs,2H), 4.97(bd,J=17Hz,0.67H), 4.70(bd,J=17Hz,0.33H), 4.35–4.55(m,3H), 4.22(m,1H), 4.08(m,2H), 3.69(d,J=17Hz,1H), 3.35(bs,H$_2$O), 2.60–2.70(m,2H), 2.10(m,2H), 1.15(m,3H).

EXAMPLE 80

Ethyl N-(2'-Naphthoyl)-(γ-benzyl ester)-R-Glutamyl(N-benzyl) glycinate

The hydrochloride of example 79 (288 mg, 0.64 mmol) was coupled to 2-naphthoic acid in a similar manner to that in example 70 to provide product (322 mg, 88% yield) after purification by chromatography. mp=103°–105° C. [α]$_D$= −6.8° (c=0.25, MeOH-DMF 1:1). MS(CI) m/e 567(m+H)+, 374, 346. $^1H$ NMR(CDCl$_3$,300MHz) δ 8.35(s,1H), 7.85–7.95(m,4H), 7.56(m,2H), 7.20–7.40(m,10H), 5.49(dt,J=3.5,8.5Hz,0.67H), 5.20(m,0.33H), 5.11(m,2H), 5.03(d,J=16Hz,0.67H), 4.69(s,0.67H), 4.62(d,J=16Hz,0.67), 4.10–4.45(m,4H), 3.74(d,J=16Hz,1H), 2.30–2.70(m,3H), 2.00–2.10(m,1H), 1.23(m,3H). C,H,N analysis calculated for $C_{34}H_{34}N_2O_6$: C 72.07, H 6.05, N 4.94; found C 71.83, H 6.11, N 4.87.

EXAMPLE 81

Ethyl N-(2-Naphthoyl)-R-Glutamyl(N-benzyl)glycinate

The product of example 80 (167 mg) was subjected to hydrogenolysis as in example 21 utilizing cyclohexadiene as the reductant. Product was purified by chromatography over silica with 0.5% acetic acid in ethyl acetate solution and recovered by lyophilization to provide 121 mg (86% yield) of product. mp=56°–62° C. [α]D = −10.5° (c=0.76, MeOH). MS(CI) m/e 477(m+H)+, 284, 194, 155. $^1H$ NMR(DMSO$_{d6}$,300MHz) δ 8.92(bd,J=7.5Hz,0.33H), 8.83(bd,J=7.5Hz,0.67H), 8.52(bd,J=5.5Hz,1H), 8.00(m,4H), 7.63(m,2H), 7.46(bd,J=7Hz,1H), 7.23–7.40(m,4H), 5.12(m,1H), 5.07(bs,0.33H), 4.95(m,0.67H), 4.55(m,2H), 4.19(m,0.67H), 4.06(q,J=7Hz,1.33H), 3.96(m,0.33H), 3.64(bd,J=17Hz,0.67H), 2.43(m,1.33H), 2.35(m,0.67H), 1.90–2.10(m,2H), 1.16(t,J=7Hz,2H), 1.09(t,J=7Hz,1H). C,H,N analysis calculated for $C_{27}H_{28}N_2O_6$ 0.25 H$_2$O: C 67.42, H 5.97, N 5.82; found C 67.43, H 5.88, N 5.77.

EXAMPLE 82

Ethyl N-(3,-Quinolylcarbonyl)-(γ-benzylester)-R-Glutamyl (N-benzyl)glycinate The hydrochloride of example 79 (325 mg, 0.67 mmol) was coupled to quinoline-3-carboxylic acid in a similar manner to that in example 70 to provide product (331 mg, 87.7% yield) after purification by chromatography. [α]$_D$= +5.5° (c=0.86, MeOH). MS(CI) m/e 568(m+H)+, 375, 342. $^1H$ NMR(CDCl$_3$,300MHz) δ 9.34(d,J=2Hz,1H), 8.60(d,J=1.8Hz,1H), 8.17(d,J=7.5Hz,1H), 7.92(m,1H), 7.82(m,1H), 7.63(m,1H), 7.50(m,1H), 7.20–7.40(m,9H), 5.50(dt,J=1,4.5Hz,0.67H), 5.00–5.12(m,3H), 4.69(s,0.67H), 4.62(d,J=16Hz,0.67H), 4.10–4.45(m,3H), 3.74(d,J=16Hz,1H), 2.50–2.70(m,2H), 2.30–2.50(m,1H), 2.03–2.11(m,1H), 1.60(bs,H$_2$O), 1.26(m,3H). C,H,N analysis calculated for $C_{33}H_{33}N_3O_6$ 0.7 H$_2$O: C 8.31, H 5.98, N 7.24; found C 68.28, H 5.88, N 7.13.

EXAMPLE 83

Ethyl N-(3'-Quinolylcarbonyl)-R-Glutamyl(N-benzyl)glycinate

The product of example 82 (100 mg) was subjected to hydrogenolysis as in example 21 utilizing cyclohexadiene as the reductant. Product was purified by chromatography over silica with 0.5% acetic acid in ethyl acetate solution and recovered by lyophilization to provide 55.3 mg (66% yield) of product. mp=70°–79° C. [α]$_D$= −30.4° (c=0.23, acetone). MS(CI) m/e 478(m+H)+, 287, 257, 194, 156. $^1H$ NMR(DMSO$_{d6}$,300MHz) δ 9.29(d,J=2Hz,0.33), 9.25(d,J=2Hz,0.67H), 9.15(bd,J=7.5Hz,0.33), 9.05(bd,J=7.5Hz,0.67H), 8.91(d,J=2Hz,0.33H), 8.85(d,J=2Hz,0.67H), 8.10(m,2H), 7.88(m,1H), 7.72(m,1H), 7.45(bd,J=7Hz,1H), 7.22–7.37(m,4H), 5.13(m,1.33H), 4.96(m,0.67H), 4.58(m,2H), 4.22(m,0.67H), 4.08(q,J=7Hz,1.33H), 3.96(m,0.33H), 3.65(bd,J=17Hz,0.67H), 3.35(bs,H$_2$O), 2.33–2.48(m,2H), 1.92–2.12(m,2H), 1.17(t,J=7Hz,2H), 1.09(t,J=7Hz,1H). C,H,N analysis calculated for $C_{26}H_{27}N_3O_6$ 0.33 H$_2$O: C 64.59, H 5.77, N 8.69; found C 64.47, H 5.69, N 8.71.

EXAMPLE 84

Ethyl N-(4',8'-Dihydoxyquinolyl-2-carbonyl)-γ-benzylester)-R-Glutamyl(N-benzyl)glycinate The hydrochloride of example 79 (288 mg, 0.64 mmol) was coupled to 4,8-dihydroxyquinoline-2-carboxylic acid in a similar manner to that in example 20 to provide product (234 mg, 60% yield) after purification by chromatography. mp=71°-74° C. $[\alpha]_D = -10.7°$ (c=0.56, acetone). MS(CI) m/e 600(m+H)+, 407, 379. $^1$H NMR(CDCl$_3$,300MHz) δ 7.76(m,1H), 7.55(m,1H), 7.20-7.45(m,1H), 6.95(m,1H), 5.25(m,1H), 5.18(bs,2H), 5.07(bd,J=16Hz,1H), 4.70-4.90(m,1H), 4.62(dd,J=4.5,16Hz,1H), 4.53(bd,J=16Hz,1H), 4.18(m,2H), 3.69(bd,J=16Hz,1H), 2.55-2.85(m,2H), 2.50-2.68(m,1H), 2.44(m,2H), 1.23(bt,J=7.5Hz,3H).

EXAMPLE 85

Ethyl N-(4',8'-Dihydroxyquinolyl-2-carbonyl)-R-Glutamyl(N-benzyl)glycinate

The product of example 84 (57 mg, 0.095 mmol) was subjected to hydrogenolysis as in example 21 utilizing cyclohexadiene as the reductant and DMF (1 mL) to aid in solubilization of the substrate. Product was purified by chromatography over silica with 0.5% acetic acid in ethyl acetate solution and recovered by lyophilization to provide 30.3 mg (60% yield) of product. mp=103-109° C. $[\alpha]_D = -10.0°$ (c=0.13, MeOH). $[\alpha]_D = -10.0°$ (c=0.13, MeOH). MS(CI) m/e 510(m+H)+, 482, 464, 305. $^1$H NMR(DMSO$_{d6}$,300MHz) δ 10.12(bs,1H), 9.72(m,1H), 7.96(bd,J=7Hz,0.67H), 7.69(bd,J=7.5Hz,0.33H), 7.54(m,1H), 7.37-7.50(m,3H), 7.19-7.33(m,4H), 7.12(bd,J=7.5Hz,1H), 5.18(m,0.33H), 4.95(m,0.67H), 4.55(bd,J=7.5Hz,1H), 4.50(m,1H), 4.19(m,0.67H), 4.07(bq,J=7Hz,1.33H), 3.90(m,0.33H), 3.70(bd,J=16Hz,0.67H), 3.34bs,H$_2$O), 2.25-2.37(m,2H), 2.15(m,1H), 2.00(m,1H), 1.14(t,J=7Hz,2H), 1.07(t,J=7Hz,1H).

EXAMPLE 86

N-(2'-Methylphenylaminocarbonyl)-(γ-benzyl ester)-S-Glu-di-n-pentylamide

To a solution of the hydrochloride salt of (γ-benzyl ester)-S-Glu-di-n-pentylamide (0.1 g, 0.24 mmol) in THF (7 mL) was added TEA (40 μL, 0.3 mmol) and a slight excess of 1-methylphenylisocyanate (0.055 g, 0.42 mmol). The reaction mixture was stirred overnight at ambient temperature. The solvents were evaporated and residue purified by chromatography using EtOAc and hexane as the elutant mixture. Pure fractions were pooled and the volatiles removed in vacuo to yield an oily product (0.075 g) in 62% yield. MS(CI) m/e 510(m+H)+. $^1$H NMR(CDCl$_3$,300MHz) δ 0.8-0.95(m,6H), 1.1-1.35(m,8H), 1.36-1.5(m,4H), 1.72-1.83(m,1H), 2.0-2.12(m,1H), 2.21(s,3H), 2.38-2.60(m,2H), 2.97-3.08(m,1H), 3.15-3.3(m,1H), 3.4-3.55(m,2H), 4.9(m,1H), 5.1(s,2H), 6.02(d,J=9Hz,1H), 6.47(s,1H), 7.05(t,J=7Hz,1H), 7.08-7.19(m,2H), 7.35(m,5H), 7.48(d,J=9Hz,1H). C,H,N analysis calculated for C$_{30}$H$_{43}$N$_3$O$_4$ 0.25 H$_2$O: C 70.07, H 8.53, N 8.17; found C 69.79, H 8.30, N 8.18.

EXAMPLE 87

Methyl (γ-benzyl ester)-R-Glutamyl-S-phenylglycinate hydrochloride

The product of example 35 was deprotected in a similar manner to that in example 79. The product was concentrated under vacuum to an oil which was used without further purification.

EXAMPLE 88

Methyl N-(2'-Naphthoyl)-(γ-benzyl ester)-R-Glutamyl-S-phenylglycinate

The hydrochloride of example 87 (157 mg, 0.37 mmol) was coupled with 2-naphthoic acid as in example 80 to provide product (156.2 mg, 78% yield) after chromatography. mp=154°-6° C. $[\alpha]_D = +38.4°$ (c=0.24, acetone). MS(CI) m/e 539(m+H)+, 374, 347, 155. $^1$H NMR(CDCl$_3$,300MHz) δ 8.36(s,1H), 7.89(m,4H), 7.56(m,3H), 7.43(d,J=7Hz,1H), 7.32-7.40(m,10H), 5.55(d,J=7Hz,1H), 5.12(s,2H), 4.84(dt,J=4.8,7.5Hz,1H), 3.70(s,3H), 2.72(m,1H), 2.45(m,1H), 2.10-2.33(m,2H). C,H,N analysis calculated for C$_{32}$H$_{30}$N$_2$O$_6$ C 69.05, H 5.79, N 5.03; found C 69.26, H 5.74, N 4.90.

EXAMPLE 89

Methyl N-(2'-Naphthoyl)-R-Glutamyl-S-phenylglycinate

The product of example 88 (73 mg, 0.136 mmol) was subjected to hydrogenolysis as in example 21 using cyclohexadiene as the reductant and DMF (1 mL) to solubilize the substrate for transfer to the reaction vessel. Yield 48 mg (79%). mp=56°-63° C. $[\alpha]_D = +32.9°$ (c=0.34, MeOH). MS(CI) m/e 449(m+H)+, 329, 284, 273, 257, 155. $^1$H NMR(DMSO$_{d6}$,300MHz) δ 8.90(d,J=7Hz,1H), 8.64(d,J=8Hz,1H), 8.52(bs,1H), 7.95-8.06(m,4H), 7.58-7.67(m,2H), 7.35-7.42(m,6H), 5.48(d,J=7Hz,1H), 4.68(m,1H), 3.63(s,3H), 2.32(m,2H), 1.98(m,2H).

EXAMPLE 90

Methyl N-(3'-Quinolylcarbonyl)-(γ-benzyl ester)-R-Glutamyl-S-phenylglycinate

The hydrochloride of example 87 (221 mg, 0.528 mmol) was coupled with quinoline-3-carboxylic acid as in example 80 to provide product (170 mg, 63% yield) after chromatography. mp=136°-137.5° C. $[\alpha]_D = +37.9°$ (c=0.24, acetone). MS(CI) m/e 540(m+H)+, 480, 432, 375, 156. $^1$H NMR(CDCl$_3$,300MHz) δ 9.34(d,J=2Hz,1H), 8.62(d,J=2Hz,1H), 8.18(d,J=7.5Hz,1H), 7.90(dd,J=1,7.5Hz,1H), 7.83(m,1H), 7.70(bd,J=7Hz,1H), 7.6(m,1H), 7.54(bd,J=7Hz,1H), 7.28-7.40(m,10H), 5.55(d,J=7Hz,1H), 5.16(d,J=12Hz,1H), 5.12(d,J=12Hz,1H), 4.85(dt,J=5,7Hz,1H), 3.71(s,3H), 2.75(m,1H), 2.48(m,1H), 2.15-2.33(m,2H). C,H,N analysis calculated for C$_{31}$H$_{29}$N$_3$O$_6$: C 69.01, H 5.42, N 7.79; found C 68.63, H 5.46, N 7.76.

EXAMPLE 91

Methyl N-(3,-Quinolylcarbonyl)-R-Glutamyl-S-phenylglycinate

The product of example 90 (67 mg, 0.124 mmol) was subjected to hydrogenolysis as in example 21 using cyclohexadiene as the reductant and DMF (1 mL) to solubilize the substrate for transfer to the reaction vessel. Yield 28 mg (50%). mp=182°-185° C. [α]$_D$=+46.6° (c=0.075, MeOH). MS(CI) m/e 450(m+H)+, 285 256, 156. $^1$H NMR(DMSO$_{d6}$,300MHz) δ 9.30(d,J=2Hz,1H), 8.96(d,J=7Hz,1H), 8.90(m,2H), 8.11(m,2H), 7.88(m,1H), 7.71(m,1H), 7.39(m,5H), 5.49(d,J=7Hz,1H), 4.72(m,1H), 3.64(s,3H), 3.35(bs,H$_2$O), 2.32(m,2H), 1.98(m,2H). C,H,N analysis calculated for C$_{24}$H$_{23}$N$_3$O$_6$ 0.67 H$_2$O: C 62.48, H 5.31, N 9.11; found C 62.23, H 5.29, N 8.93.

EXAMPLE 92

Methyl N-(4',8'-Dihydroxyquinolyl-2-carbonyl)-(γ-benzyl ester)- R-Glutamyl-S-phenylglycinate The hydrochloride of example 87 (146 mg, 0.35 mmol) was coupled with 4,8-dihydroxyquinoline-2-carboxylic acid as in example 80 to provide product 65.6 mg, (33% yield) after chromatography. mp=234°-5° C. MS(CI) m/e 572(m+H)+, 385, 294, 277, 211, 192, 166. $^1$H NMR(DMSO$_{d6}$,300MHz) δ 10.08(bs,1H), 9.56(d,J=7Hz,1H), 9.00(d,J=7Hz,1H), 7.55(m,2H), 7.25-7.45(m,10H), 7.12(d,J=7Hz,1H), 5.48(d,J=7Hz,1H), 5.05(s,2H), 4.75(m,1H), 3.61(s,3H), 3.30(bs,H$_2$O), 2.43(m,2H), 2.10(m,2H). C,H,N analysis calculated for C$_{31}$H$_{29}$N$_3$O$_8$ 0.5 H$_2$O: C 64.13, H 5.21, N 7.24; found C 64.43, H 5.07, N 7.25.

EXAMPLE 93

Methyl N-(4',8'-Dihydroxyquinolyl-2-carbonyl)-R-Glutamyl-S-phenylglycinate

The product of example 92 (49.7 mg, 0.087 mmol) was subjected to hydrogenolysis as in example 21 using cyclohexadiene as the reductant and DMF (2 mL) to solubilize the substrate for transfer to the reaction vessel. Yield 31.4 mg (75%). MS(CI) m/e 482(m+H)+, 464, 317, 289, 277, 205. $^1$H NMR(DMSO$_{d6}$,300MHz) δ 9.56(m,1H), 8.96(bd,J=7Hz,1H), 7.57(bd,J=8Hz,1H), 7.50(bs,1H), 7.33-7.45(m,7H), 7.12(bd,J=8Hz,1H), 5.47(d,J=7Hz,1H), 4.71(m,1H), 3.62(s,3H), 3.3(bs,H$_2$O), 2.28(m,2H), 2.00(m,2H). C,H,N analysis calculated for C$_{24}$H$_{23}$N$_3$O$_8$ 0.33 H$_2$O: C 59.14, H 4.89, N 8.62; found C 59.07, H 4.95, N 8.39.

EXAMPLE 94

Methyl N-(t-Butyloxycarbonyl)-(γ-benzyl ester)-R-Glutamyl-S-leucinate

N-(t-Butyloxycarbonyl)-(γ-benzyl ester)-R-glutamic acid (1.077 grams, 3.0 mmol) and methyl-S-leucinate hydrochloride were coupled in a manner similar to that in example 21 to provide 1.28 grams (86% yield) of product after chromatography. mp=69°-71° C. [α]$_D$=−1.1° (c=0.62, acetone). MS(CI) m/e 482(m+NH$_4$)+, 465(m+H)+, 409, 365, 309, 292, 274, 257. $^1$H NMR(CDCl$_3$,300MHz) δ 7.36(m,5H), 6.55(m,1H), 5.30(m,1H), 5.14(s,2H), 4.56(m,1H), 4.19(m,1H), 3.72(s,3H), 2.56(dt,J=7,17Hz,1H), 2.47(dt,J=7,17Hz,1H), 2.17(m,1H), 1.97(m,1H), 1.50-1.67(m,3H), 1.41(s,9H), 0.92(d,J=6Hz,6H). C,H,N analysis calculated for C$_{24}$H$_{36}$N$_2$O$_7$ C 62.05, H 7.81, N 6.03; found C 61.98, H 7.80, N 5.96.

EXAMPLE 95

Methyl (γ-benzyl ester)-R-Glutamyl-S-leucinate hydrochloride

The product of example 94 (1.07 grams, 2.30 mmol) was treated with 6.0 mL of 4.5 N hydrochloric acid in dioxane. The hydrochloride was isolated as an oil as in example 87, yield 914 mg (99%). MS(CI) m/e 365(m+H)+, 192. $^1$H NMR(DMSO$_{d6}$, 300MHz) δ 9.05(d,J=7Hz,1H), 8.34(bs,3H), 7.32-7.42(m,5H), 5.11(s,2H), 4.28-4.36(m,1H), 3.91(t,J=6Hz,1H), 3.64(s,3H), 2.36-2.58(m,2H), 2.02-2.09(m,2H), 1.49-1.65(m,3H), 0.86(d,J=6Hz,3H), 0.82(d,J=6Hz,3H).

EXAMPLE 96

Methyl N-(2,-naphthoyl)-(γ-benzyl ester)-R-Glutamyl-S-leucinate

Naphthalene-2-carboxylic acid (121 mg, 0.70 mmol) and the product of example 95 (200 mg, 0.50 mmol) were coupled and extracted as in example 80. The resulting residue was chromatographed on silica gel eluted with a step gradient of 9:1 to 2:1 hexanes—EtOAc to give 149 mg, 0.29 mmol (44% yield). mp=95°-98° C. [α]$_D$=+17.3° (c=0.55, CHCl$_3$). MS(CI) m/e 519(m+H)+, 428, 411. $^1$H NMR(CDCl$_3$,300MHz) δ 0.94(dd,J=2,6Hz,6H), 1.55-1.71(m,2H), 2.13-2.38(m,3H), 2.55(dt,J=7,17Hz,1H), 2.72-2.82(m,1H), 3.67(s,3H), 4.54-4.65(m,1H), 4.78-4.84(m,1H), 5.13(s,2H), 6.91(d,J=8Hz,1H), 7.28-7.33(m,5H), 7.50-7.61(m,3H), 7.86-7.94(m,4H), 8.36(s,1H). C,H,N analysis calculated for C$_{30}$H$_{34}$N$_2$O$_6$ C 69.48, H 6.61, N 5.40; found C 69.21, H 6.71, N 5.33.

EXAMPLE 97

Methyl N-(2'-Naphthoyl)-R-Glutamyl-S-leucinate

The product of example 96 (74 mg, 0.14 mmol) was dissolved in 10 mL MeOH and treated with 20 mg of 10% Pd/C (prewetted with solvent under N$_2$) and 1 atmosphere of hydrogen gas. After 3 hours, the catalyst was filtered and rinsed with fresh solvent. The residue was dissolved in MeOH, filtered through a 0.5μ filter and then diluted with water. The aqueous mixture was frozen and lyophilized to give 31 mg, 0.072 mmol (52% yield). R$_f$=0.22 (80:20:1 CHCl$_3$—MeOH—NH$_4$OH). mp=58°-65° C. [α]$_D$=−31.8° (c=1.0, MeOH). MS(CI) m/e 429(m+H)+, 284. $^1$H NMR(DMSO$_{d6}$,300MHz) δ 0.83(d,J=6Hz,3H), 0.86(d,J=6Hz,3H), 1.43-1.63(m,3H), 1.94-2.03(m,2H), 2.33(bt,J=7Hz,2H), 3.62(s,3H), 4.28-4.36(m,1H), 4.56(q,J=7Hz,1H), 7.56-7.65(m,2H), 7.96-8.06(m,4H), 8.42(d,J=8Hz,1H), 8.52(s,1H), 8.83(d,7Hz,1H). C,H,N analysis calculated for C$_{23}$H$_{28}$N$_2$O$_6$ 0.6 H$_2$O: C 62.89, H 6.70, N 6.38; found C 62.75, H 6.51, N 6.44.

EXAMPLE 98

Methyl N-(3'-Quinolylcarbonyl)-(γ-benzyl ester)-R-Glutamyl-S-leucinate

Quinoline-3-carboxylic acid (139 mg, 0.8 mmol) and the product of example 95 (200 mg, 0.50 mmol) were coupled as in example 82. Silica gel chromatography of the residue eluted with a step gradient of 9:1 to 1:1 hexane—EtOAc gave 99 mg, 0.19 mmol (39% yield). R$_f$=0.22 (1:1 hexane—EtOAc). mp=105°-107° C. [α]$_D$=+16.9° (c=1.5, CHCl$_3$) MS(CI) m/e 520(m+H)+, 429, 412. $^1$H NMR(CDCl$_3$,300MHz) δ 0.93(d,J=2Hz,3H), 0.96(d,J=2Hz,3H), ,3H), 2.17-2.37(m,2H), 2.57(ddd,J=5,7,17Hz,1H), 2.80(ddd,J=5,8,17Hz,1H), 3.69(s,3H), 4.58-4.65(m,1H), 4.76-4.82(m,1H), 5.13(d,J=12Hz,1H), 5.18(d,J=12Hz,1H), 6.90(d,J=8Hz,1H), 7.28-7.35(m,5H), 7.63(dt,J=1,8Hz,1H), 7.76(d,J=7Hz,1H), 7.82(dt,J=1,7Hz,1H), 7.91(d,J=8Hz,1H), 8.16(d,J=8Hz,1H), 8.62(d,J=2Hz,1H), 9.36(d,J=2Hz,1H). C,H,N analysis calculated for C$_{29}$H$_{33}$N$_3$O$_6$ 0.3 H$_2$O: C 66.35, H 6.45, N 8.00; found C 66.34, H 6.43, N 7.96.

EXAMPLE 99

Methyl N-(3'-Quinolylcarbonyl)-R-Glutamyl-S-leucinate

The product of example 98 (100 mg, 0.192 mmol) was treated with 25 mg of 10% Pd/C (prewetted with EtOH under N$_2$) and 1 atmosphere of hydrogen gas in 25 mL of EtOH. Another 20 mg of catalyst was carefully added after 4 hours and the reaction was allowed to continue overnight. After filtration of the catalyst and evaporation of the solvent, the residue was chromatographed on silica gel eluted with a 9:1 CH$_2$Cl$_2$—EtOH to 80:20:1 CHCl$_3$—MeOH—NH$_4$OH step gradient. After evaporation of the product fractions, the residue was mixed with aqueous EtOH, frozen and lyophilized to give 39 mg, 0.092 mmol (48% yield). mp=194°-6° C. [α]$_D$=−26.6° (c=1.64, MeOH). MS(CI) m/e 430(m+H)+, 412, 285, 257, 199, 174, 156. $^1$H NMR(CDCl$_3$,300 MHz) δ 0.95(dd,J=5,6Hz,6H), 1.62-1.72(m,3H), 2.08-2.27(m,2H), 2.49-2.53(m,2H), 3.70(s,3H), 3.98-4.02(m,1H), 4.22(dd,J=6,8Hz,1H), 7.21(dt,J=1,8Hz,1H), 7.39(dt,J=1,7Hz,1H), 8.06-8.12(m,2H), 8.86(d,J=2Hz,1H), 9.28(d,J=2Hz,1H).

EXAMPLE 100

Methyl N-(4'8'-Dihydroxyquinolyl-2-carbonyl)-(γ-benzyl ester)-R-Glutamyl-S-leucinate 4,8-Dihydroxyquinoline-2-carboxylic acid (62 mg, 0.3 mmol), the product of example 95 (100 mg, 0.25 mmol), HOBt (41 mg, 0.3 mmol), and TEA (42 μL, 0.3 mmol) were dissolved in 5 mL DMF and treated with EDCI (57 mg, 0.3 mmol). After 3 days, the solvent was evaporated and the residue in EtOAc was extracted as in example 82. The residue from evaporation was chromatographed in silica gel eluted with a 1% to 5% EtOH in CH$_2$Cl$_2$ to give 108 mg, 0.196 mmol (78% yield) as a light yellow solid. mp=208°-10° C. [α]$_D$=−28.0° (c=0.46, MeOH). MS(FAB+) m/e 552(m+H)+, 374. $^1$H NMR(CDCl$_3$—CD$_3$OD,300MHz) δ 0.92(bd,J=5Hz,6H), 1.55-1.68(m,3H), 2.15-2.37(m,2H), 2.48-2.66(m,2H), 3.70(s,3H), 4.52-4.57(m,1H), 4.73(dd,J=5,12Hz,1H), 5.13(s,2H), 7.16(bd,J=7Hz,1H), 7.28-7.33(m,6H), 7.40(s,1H), 7.72(dd,J=1,8Hz,1H). C,H,N analysis calculated for C$_{29}$H$_{33}$N$_3$O$_8$ 0.25 H$_2$O C 2.64, H 6.07, N 7.56; found C 62.41, H 5.91, N 7.39.

EXAMPLE 101

Methyl N-(4',8'-Dihydroxyquinolyl-2-carbonyl)-R-Glutamyl-S-leucinate

The product of example 100 (50 mg, 0.091 mmol) was treated with 10 mg of 10% Pd/C in 5 mL MeOH as in example 97. After 2 hours, the catalyst was filtered and the solvent was evaporated. mp=228°-30° C. [α]$_D$=−42.0° (c=1.07, DMF). MS(CI) m/e 462(m+H)+. $^1$H NMR(DMSO$_{d6}$,300MHz) δ 0.83(d,J=6Hz,3H), 0.88(d,J=6Hz,3H), 1.43-1.66(m,3H), 1.42-2.15(m,2H), 2.32(bt,J=7Hz,2H), 3.61(s,3H), 4.29-4.36(m,1H), 4.56-4.63(m,1H), 7.10(dd,J=1,7Hz,1H), 7.40(t,J=8Hz,1H), 7.47(bs,1H), 7.56(dd,J=1,8Hz,1H), 8.45(d,J=7Hz,1H), 9.55(bd,J=7Hz,1H). C,H,N analysis calculated for C$_{22}$H$_{27}$N$_3$O$_8$ 1.2 H$_2$O: C 54.70, H 6.13, N 8.70; found C 54.63, H 5.79, N 8.30.

EXAMPLE 102

N-(t-Butyloxycarbonyl)-(γ-benzyl ester)-R-Glutamyl-bis(carboethoxymethyl)amide N-(t-Butyloxycarbonyl)-(γ-benzyl ester)-R-glutamic acid (1.98 gram, 5.9 mmol) and diethyl imidodiacetate (5.32 gram, 28.15 mol) were coupled in a manner similar to that in example 78 to provide 2.62 grams (88% yield) of product after chromatography. [α]$_D$=+16.5° (c=1.16, MeOH). MS(CI) m/e 526(m+NH$_4$)+, 509(m+H)+, 470, 453, 436, 423, 409, 380. $^1$H NMR(CDCl$_3$,300MHz) δ 7.35(m,5H), 5.31(bd,J=8Hz,1H), 5.17(d,J=16Hz,1H), 5.12(d,J=16Hz,1H), 4.70(dt,J=4,9Hz,1H), 4.38(bs,2H), 4.05-4.27(m,6H), 2.40-2.60(m,2H), 2.13(m,1H), 1.73(m,1H), 1.43(bs,9H), 1.28(t,J=7Hz,3H), 1.26(t,J=7Hz,3H).

EXAMPLE 103

(γ-Benzyl ester)-R-Glutamyl-bis(carboethoxymethyl)amide hydrochloride

The product of example 102 (2.16 gram, 4.25 mmol) was deprotected as in example 95 to provide 1.88 grams as an oil which was utilized as is. MS(CI) m/e 409(m+H)+, 391, 380, 363. $^1$H NMR(DMSO$_{d6}$,300MHz) δ 8.46(bs,3H), 7.30-7.41(m,5H), 5.12(s,2H), 4.36-4.52(m,3H), 4.02-4.23(m,6H), 2.63-2.73(m,1H), 2.56(dd,J=5,10Hz,1H), 1.85-2.12(m,2H), 1.15-1.23(m,6H).

EXAMPLE 104

N-(2'-Naphthoyl)-(γ-Benzyl ester)-R-Glutamyl-bis(carboethoxymethyl)amide

EDCI (96 mg, 0.50 mmol) was added to a solution of 2-naphthoic acid (87 mg, 0.50 mmol), the product of example 103 (200 mg, 0.45 mmol) and TEA (70 μL, 0.5 mmol) in 5 mL CH$_2$Cl$_2$ at room temperature overnight. After evaporation of the solvent, the residue was dissolved in EtOAc and extracted with 0.1 M citric acid(3×) and water(3×). The EtOAc was then dried over MgSO$_4$, filtered and the solvent evaporated in vacuo. The residue was chromatographed on silica gel eluted with 4:1 to 2:1 step gradient to give 193 mg, 0.34 mmol (76% yield) as an oil. [α]$_D$=+27.7° (c=0.73, MeOH). MS(CI) m/e 563 (m+H)+, 374. $^1$H NMR (CDCl$_3$,300MHz) δ 1.27(dt,J=1,7Hz,6H), 1.92-2.03(m,1H), 2.27-2.38(m,1H), 2.50(dt,J=6,17Hz,1H), 2.59-2.70(m,1H), 4.10(d,J=17Hz,1H), 4.15-4.23(m,4H), 4.30(d,J=17Hz,1H), 4.45(d,J=11Hz,1H), 4.50(d,J=17Hz,1H), 5.11(d,J=11Hz,1H), 5.15(d,J=11Hz,1H), 5.25-5.32(m,1H), 7.22(d,J=8Hz,1H), 7.29-7.35(m,5H), 7.51-7.60(m,2H), 7.82-7.93(m,4H), 8.32(s,1H). C,H,N analysis calculated for C$_{31}$H$_{34}$N$_2$O$_8$ 0.3 H$_2$O C 65.55, H 6.14, N 4.93; found C 65.52, H 6.17, N 4.90.

EXAMPLE 105

N-(2,-Naphthoyl)-R-Glutamyl-bis(carboethoxymethyl)amide

The product of example 104 (100 mg, 0.18 mmol) was dissolved in 10 mL EtOH and then treated with 25 mg of 10% Pd/C (prewetted with solvent under N$_2$) under 1 atmosphere H$_2$ (balloon) overnight. The catalyst was removed by filtration and the solvent was evaporated in vacuo. The residue was redissolved in EtOH and filtered through a 5μ filter. The filtrate was then mixed with water, frozen and lyophilized to yield an oil 67 mg, (0.14 mmol, 79% yield). R$_f$=0.35 (80:20:1 CHCl$_3$—MeOH—NH$_4$OH). [α]$_D$= +20.4° (c=1.41, MeOH). MS(FAB+) m/e 473(m+H)$^+$, 495(m+Na)$^+$, 284, 256. $^1$H NMR(DMSO$_{d6}$,300MHz) δ 1.10(t,J=7Hz,3H), 1.17(t,J=7Hz,3H), 1.83-2.08(m,2H), 2.32(bt,J=8Hz,2H), 3.86-4.11(m,5H), 4.19(d,J=17Hz,1H), 4.48(d,J=18Hz,1H), 4.55(d,J=18Hz,1H), 4.43-5.01(m,1H), 7.57-7.65(m,2H), 7.93-8.04(m,4H), 8.52(s,1H), 8.89(d,J=8Hz,1H). C,H,N analysis calculated for C$_{24}$H$_{28}$N$_2$O$_8$ 0.6 H$_2$O: C 59.65, H 6.09, N 5.80; found C 59.69, H 5.70, N 5.70.

EXAMPLE 106

N-(3'-Quinolylcarbonyl)-(γ-Benzyl ester)-R-Glutamyl-bis(carboethoxymethyl)amide

Quinoline-3-carboxylic acid (87 mg, 0.5 mmol) was coupled to the product of example 103 (200 mg, 0.45 mmol) as in example 104. Column chromatography on silica gel eluted with a 9:1 to 2:1 hexane—EtOAc step gradient yielded an oil 131 mg (0.23 mmol, 52% yield). [α]$_D$= +28.0° (c=0.55, MeOH). MS(CI) m/e 564(m+H)+. $^1$H NMR(CDCl$_3$,300MHz) δ 1.23-1.32(m,6H), 1.92-2.03(m,1H), 2.28-2.38(m,1H), 2.51(dt,J=6,17Hz,1H), 2.60-2.71(m,1H), 4.07-4.27(m,5H), 4.31(d,J=17Hz,1H), 4.49(s,2H), 5.13(d,J=11Hz,1H), 5.18(d,J=11Hz,1H), 5.25-5.32(m,1H), 7.28-7.38(m,6H), 7.62(dt,J=1,8Hz,1H), 7.82(dt,J=1,8Hz,1H), 7.90(dd,J=1,8Hz,1H), 8.15(d,J=8Hz,1H), 8.58(d,J=2Hz,1H), 9.32(d,J=2Hz,1H). C,H,N analysis calculated for C$_{30}$H$_{33}$N$_3$O$_8$ 0.5 H$_2$O: C 62.93, H 5.99, N 7.94; found C 62.95, H 6.09, N 7.22.

EXAMPLE 107

N-(3,-Quinolylcarbonyl)-R-Glutamyl-bis(carboethoxymethyl)amide

The product of example 106 (70 mg, 0.124 mmol) was treated with 20 mg of 10% Pd/C and 1 atmosphere hydrogen gas in 7 mL EtOH. After 6 hours, the catalyst was filtered and the solvent concentrated, mixed with water and then frozen and lyophilized to yield 49 mg (0.10 mmol, 84% yield). mp=48°-52° C. [α]$_D$= +17° (c=1.37, MeOH). MS(FAB+) m/e 474(m+H)$^+$, 496(m+Na)$^+$. $^1$H NMR(DMSO ,300MHz) δ 1.12(t,J=7Hz,3H), 1.17(t,J=7Hz,3H), 1.83-2.10(m,2H), 2.34(bt,J=7Hz,2H), 3.42-4.12(m,5H), 4.19(d,J=17Hz,1H), 4.51(d,J=17Hz,1H), 4.55(d,J=17Hz,1H), 4.95-5.02(m,1H), 7.71(dt,J=1,8Hz,1H), 7.88(dt,J=1,8Hz,1H), 8.10(d,J=8Hz,2H), 8.88(d,J=2Hz,1H), 9.18(d,J=7Hz,1H), 9.28(d,J=2Hz,1H). C,H,N analysis calculated for C$_{23}$H$_{27}$N$_3$O$_8$ 0.7 H$_2$O: C 56.83, H 5.89, N 8.65; found C 56.75, H 5.53, N 8.52.

EXAMPLE 108

N-(4,8,-Dihydroxyquinolyl-2-carbonyl)-(γ-Benzyl ester)-R-Glutamyl-bis(carboethoxymethyl)amide 4,8-Dihydroxyquinoline-2-carboxylic acid (103 mg, 0.50 mmol), the product of example 103 (202 mg, 0.45 mmol), HOBt (68 mg, 0.5 mmol) and TEA (70 μL, 0.5 mmol) were dissolved in 5 mL DMF and treated with EDCI (96 mg, 0.50 mmol) overnight. After evaporation of the solvent, the residue was extracted as in example 82. The residue was chromatographed on silica gel eluted with 1% to 6% EtOH in methylene chloride step gradient to yield 193 mg (0.32 mmol, 72% yield) of nearly pure product. A second silica gel column eluted with 4:1 to 1:3 hexane-EtOAc step gradient yielded pure product. mp=79°-82° C. [α]$_D$=23.9° (c=1.6, MeOH). MS(CI) m/e 596(m+H)$^+$, 407, 379. $^1$H NMR(DMSO$_{d6}$,500MHz) δ 1.18(t,J=6Hz,3H), 1.23(t,J=6Hz,3H), 1.98-2.05(m,1H), 2.13-2.20(m,1H), 2.37-2.47(m,2H), 3.82-3.94(m,2H), 4.00(d,J=16Hz,1H), 4.04(d,J=7Hz,1H), 4.07(d,J=7Hz,1H), 4.18(d,J=16Hz,1H), 4.38(d,J=17Hz,1H), 4.53(d,J=17Hz,1H), 4.98-5.03(m,1H), 5.05(d,J=11Hz,1H), 5.08(d,J=11Hz,1H), 7.08(d,J=8Hz,1H), 7.28-7.36(m,4H), 7.42(t,J=7Hz,1H), 7.52(s,1H), 7.54(d,J=7Hz,1H), 7.71(d,J=8Hz,1H), 10.04(s,1H), 11.75(bs,1H). C,H,N analysis calculated for C$_{30}$H$_{33}$N$_3$O$_{10}$ 0.5 H$_2$O: C 59.60, H 5.67, N 6.97; found C 59.69, H 5.56, N 6.88.

EXAMPLE 109

N-(4',8'-Dihydroxyquinolyl-2-carbonyl)-R-Glutamyl-bis(carboethoxymethyl)amide

The product of example 108 (22 mg, 0.37 mmol) was treated with mg of 10% Pd/C in 5 mL MeOH as in example 97. After 2 hours, the catalyst was filtered and the solvent was evaporated. The crude product was chromatographed on silica gel eluted with 70:30:1 EtOAc-hexanes-HOAc. [α]$_D$= +10.0° (c=0.21, MeOH). MS(CI) m/e 506(m+H)$^+$. $^1$H NMR(DMSO$_{d6}$,300MHz) 1.07-1.17(m,6H), 1.86-1.97(m,1H), 2.04-2.14(m,1H), 2.18-2.36(m,2H), 3.82-3.96(m,2H), 4.02-4.09(m,3H), 4.18(d,J=16Hz,1H), 4.42(d,J=18Hz,1H), 4.56(d,J=18Hz,1H), 4.92-5.00(m,1H), 7.08(dd,J=1,7Hz,1H), 7.39(t,J=8Hz,1H), 7.46(s,1H), 7.55(dd,J=1,8Hz,1H), 9.68(d,J=8Hz,1H), 12.0(bs,1H). C,H,N analysis calculated for C$_{23}$H$_{27}$N$_3$O$_{10}$ 1.5 H$_2$O: C 1.88, H 5.68, N 7.89; found C 52.32, H 5.51, N 7.33.

EXAMPLE 110

N-(2,-Indolylcarbonyl)-(Nγ-n-pentylamide)-R-Glu-N$^α$,N$^α$-di-n-pentyl amide

The product of example 4 (50 mg, 0.116 mmol) and n-amylamine (35 μL, 0.30 mmol) were dissolved in 5 mL CH$_2$Cl$_2$ and treated with EDCI (23 mg, 0.12 mmol). TEA (17 μL, 0.12 mmol) and additional EDCI (23 mg) were added after 1 day. After 2 days, the solvent was evaporated and the residue in EtOAc was washed with 0.1% citric acid, water, dried and evaporated. The crude residue was chromatographed on silica gel eluted with a 4:1 to 1:1 hexane—EtOAc stepped gradient to yield 26.7 mg, 0.054 mmol (46%). mp=103-5° C. $R_f=0.56(1:1$ hexane—EtOAc). MS(CI) m/e 499(m+H)$^+$, 341. $^1$H NMR(CDCl$_3$,300MHz) δ 0.92(t,J=7Hz,3H), 1.23-1.38(m,12H), 1.49-1.60(m,6H), 1.83-1.95(m,1H), 2.13-2.23(m,1H), 2.29-2.33(m,2H), 3.03(dt,J=7,14Hz,1H), 3.12-3.47(m,4H), 3.63(dt,J=7,14Hz,1H), 4.99(dt,J=2,9Hz,1H), 6.73(bt,J=5Hz,1H), 7.01(dd,J=1,2Hz,1H), 7.15(dt,J=1,7Hz,1H), 7.29(dt,J=1,7Hz,1H), 7.42(dd,J=1,8Hz,1H), 7.47(d,J=8Hz,1H), 7.66(dd,J=1,7Hz,1H), 9.12(s,1H). C,H,N analysis calculated for C$_{29}$H$_{46}$N$_4$O$_3$ C 69.84, H 9.30, N 11.24; found C 69.78, H 9.28, N 11.13.

EXAMPLE 111

N-(2'-Indolylcarbonyl)-[N$^\gamma$-(2,-phenylethylamide)]-R-Glu-N$^\alpha$,N$^\alpha$-di-n-pentyl amide The product of example 4 (50 mg, 0.116 mmol) was reacted with β-phenethylamine (38 μL, 0.30 mmol) in the same manner as in example 110. The reaction yielded 36 mg, 0.068 mmol (58%). MS(CI) m/e 533(m+H)$^+$, 376, 348. $^1$H NMR(CDCl$_3$,300MHz) δ 0.85-0.92(m,6H), 1.25-1.36(m,8H), 1.48-1.65(m,4H), 1.85-1.96(m,1H), 2.13-2.32(m,3H), 2.82(t,J=8Hz,2H), 3.02-3.22(m,2H), 3.37-3.65(m,4H), 5.02(dt,J=2,9Hz,1H), 6.54(t,J=5Hz,1H), 6.99(dd,J=1,2Hz,1H), 7.12-7.32(m,8H), 7.40-7.46(m,2H), 7.68(dd,J=1,7Hz,1H), 9.11(s,1H). C,H,N analysis calculated for C$_{32}$H$_{44}$N$_4$O$_3$ 0.3 H$_2$O: C 71.42, H 8.35, N 10.41; found C 71.46, H 8.32, N 10.43.

EXAMPLE 112

N-(4',8'-Dihydroxyquinolyl-2'-carbonyl)-(γ-benzyl ester)-R-Glu-di-n-pentylamide

To a solution of the hydrochloride of example 2 (1.0 grams, 2.42 mmol) in DMF (10mL) at 0° C. were added NMM (0.55 mL, 5 mmol), HOBt (0.33 gram, 2.42 mmol), 4,8-dihydroxyquinoline-2-carboxylic acid (0.5 gram, 2.44 mmol) and DCC (0.55 grams, 2.6 mmol). The reaction was stirred overnight with warming to ambient temperature. The solvents were evaporated in vacuo and the resulting residue was dissolved in EtOAc. The dicyclohexylurea was filtered away, the filtrate was concentrated and the residue chromatographed on silica gel using CHCl$_3$ and MeOH (18:1). The solvents were removed and the semisolid yellow residue dried under vacuum at ambient temperature. Product was isolated in 55% yield 0.75 grams. MS(CI) m/e 564(m+H)$^+$. $^1$H NMR(CDCl$_3$,300MHz) δ 0.85-0.95(m,6H), 1.22-1.42(m,8H), 1.55-1.75(m,4H), 1.75-2.0(m,2H), 2.5-2.62(m,1H), 2.65-2.8(m,1H), 3.05-3.20(m,1H), 3.30-3.52(m,2H), 3.64-3.78(m,1H), 5.0(m,1H), 5.2(s,2H), 6.95(m,2H), 7.15(m,7H), 7.6(d,J=9Hz,1H), 8.1(bs,1H), 9.2(bs,1H). C,H,N analysis calculated for C$_{32}$H$_{41}$N$_3$O$_6$ 0.25 H$_2$O: C 67.64, H 7.36, N 7.40; found C 67.62, H 7.03, N 7.66.

EXAMPLE 113

N-(4',8'-Dihydroxyquinolyl-2,-carbonyl)-R-Glu-N$^\alpha$,$^\alpha$-di-n-penty amide To a suspension of 0.3 grams 10% Pd/C in MeOH (15 mL) and cyclohexadiene (2 mL) under inert atmosphere (N$_2$) was added via cannula solution of the benzyl ester of example 112 (0.4 grams, 0.71 mmol) in MeOH. The reaction mixture was stirred overnight at ambient temperature. The mixture was filtered through celite and washed several times with MeOH. The filtrate and washings were combined and concentrated in vacuo. The product was purified by flash chromatography using EtOAc/hexane and HOAc (70:30:1) as the elutant mixture. Removal of the volatiles in vacuo provided pure product in 60% yield (0.2 grams). MS(CI) m/e 474(m+H)+ $^1$H NMR(DMSO$_{d6}$,300MHz) δ 0.75-0.88(m,6H), 1.1-1.35(m,8H), 1.4-1.65(m,4H), 1.95-2.10(m,2H), 2.35-2.42(m,2H), 3.1(m,1H), 3.2-3.4(m,3H), 5.0(m,1H), 7.10(d,J=9Hz,1H), 7.42(t,J=10Hz,1H), 7.49(bs,1H), 7.55(d,J=9Hz,1H), 9.6(bd,J=9Hz,1H), 10.1(bs,1H), 12.00(bs,1H). C,H,N analysis calculated for C$_{25}$H$_{35}$N$_3$O$_6$ H$_2$O HOAc: C 58.79, H 7.49, N 7.62; found C 58.78, H 7.04, N 7.87.

EXAMPLE 114

N-(2'-Indolylcarbonyl)-R-Glu-N$^\alpha$-methoxyamide-N$^\alpha$,-N$^\alpha$-di-n-pentylamide The product of example 4 (50 mg, 0.116 mmol) was reacted with methoxyamine hydrochloride (24 mg, 0.29 mmol) in the same manner as example 110. The reaction yielded 35 mg, 0.076 mmol (66%). $^1$H NMR(CDCl$_3$,300MHz) δ 0.89(t,J=7Hz,6H), 1.23-1.37(m,8H), 1.48-1.62(m,4H), 1.85-1.94(m,1H), 2.20(bs,1H), 2.24(bs,2H), 3.00-3.08(m,1H), 3.10-3.21(m,1H), 3.32-3.43(m,1H), 3.62(dt,J=8,13Hz,1H), 3.81(s,3H), 4.94(bt,J=8Hz,1H), 7.02(s,1H), 7.15(dt,J=1,8Hz,1H), 7.30(dt,J=1,7Hz,1H), 7.42(d,J=8Hz,1H), 7.62(bd,J=7Hz,1H), 7.67(d,J=8Hz,1H), 9.28(s,1H), 9.94(s,1H).

EXAMPLE 115

N-Benzyl-(γ-benzyl ester)-R-Glu-N$^\alpha$,N$^\alpha$-di-n pentylamide

The product of example 2 (413 mg, 1.0 mmol) was dissolved in 5 mL of dry ethanol and treated consecutively with TEA (139 μL, 1.0 mmol), benzaldehyde (127 μL, 1.25 mmol) and acetic acid (57 μL, 1.0 mmol) each at 10 minute intervals. Then sodium cyanoborohydride (126 mg, 2.0 mmol) was added in 4 portions over 30 minutes. Bubbling commenced immediately and the reaction became opaque. The reaction was allowed to stir overnight. The reaction was then poured into ethyl acetate, extracted with 0.5 M sodium bicarbonate and then dried over MgSO$_4$, filtered and the ethyl acetate evaporated in vacuo. The resultant oil was chromatographed on silica gel eluted with a 9:1 to 4:1 step gradient.

EXAMPLE 116

N-Benzyl-N-(3'-quinolylcarbonyl)-R-Glu-N$^\alpha$,N$^\alpha$-di-n-pentylamide

The product of example 115, quinoline-3-carboxylic acid and TEA were dissolved in methylene chloride and treated with BOPCl. The residue after evaporation of the solvent was extracted as in example 70 and then purified by column chromatography.

EXAMPLE 117

N-Methyl-N-(3'-quinolylcarbonyl)-(γ-benzyl ester)-R-Glu-N$^\alpha$,N$^\alpha$-di-n-pentylamide The product of example 5 (100 mg, 0.176 mmol) was dissolved in 5 mL of DMF and then treated with lithium bis(trimethylsilyl) amide (170 μL, 0.17 mmol, 1.0 M in THF) followed by methyl iodide (33 μL, 0.035 mmol). After 2 hours, the solvents were evaporated and the residue was extracted with 0.1 M citric acid and 0.5

M sodium bicarbonate. Column chromatography on silica gel eluted with 9:1 to 2:1 hexane-ethyl acetate step gradient yielded 48 mg of product (0.089 mmol, 52%).

EXAMPLE 118

N-(3'-Quinolylcarbonyl)-R-Glu-$N^\alpha$,$N^\alpha$-di-n-pentylamide Dicyclohexylamine salt The product of example 15 (880 mg, 2 mmol) was dissolved in 10 mL of methylene chloride and then treated with dicyclohexylamine (4 mL, 20 mmol). After complete mixing, hexane was added (200 mL) and a solid formed. The solid was collected and rinsed with fresh hexanes and then dried in vacuo. mp = 129°–131° C. MS(CI) m/e 442(m+H)+, 398 $^1$H NMR(DMSO$_{d6}$,300MHz) δ 0.83(d,J=7Hz,3H), 0.88(d,J=5Hz,3H), 1.12–1.32(m,20H), 1.42–1.70(m,8H), 1.82–1.92(m,6H), 2.26–2.32(m,2H), 2.67–2.74(m,2H), 3.02(quintet,J=7Hz,1H), 3.23–3.35(m,1H), 3.42–3.60(m,2H), 4.82–4.90(m,1H), 7.70(dt,J=1,7Hz,1H), 7.86(dt,J=1,7Hz,1H), 8.09(d,J=8Hz,2H), 8.90(d,J=2Hz,1H), 9.31(d,J=2Hz,1H), 9.50(d,J=7Hz,1H). C,H,N analysis calculated for $C_{37}H_{58}N_4O_4$: C 71.34, H 9.39, N 9.00; found C 71.50, H 9.40, N 8.91.

The compounds of Formula I antagonize CCK which makes the compounds useful in the treatment and prevention of disease states wherein CCK or gastrin may be involved, for example, qastrointestinal disorders such as irritable bowel syndrome, ulcers, excess pancreatic or gastric secretion, hyperinsulinemia, acute pancreatitis, cancers of the gall bladder and pancreas, motility disorders, pain (potentiation of opiate analgesia), central nervous system disorders caused by CCK's interaction with dopamine such as neuroleptic disorders, tardive dyskinesia, Parkinson's disease, psychosis or Gilles de la Tourette Syndrome, disorders of appetite regulatory systems, Zollinqer-Ellison syndrome, and central G cell hyperplasia.

The ability of the compounds of Formula I to interact with CCK receptors and to antagonize CCK can be demonstrated in vitro using the following protocols.

CCK$_8$ [Asp-Tyr(SO$_3$H)-Met-Gly-Trp-Met-Asp-Phe-NH$_2$] was purchased from Beckman Instruments (Palo Alto, Ca/) and Peptide International (Louisville, Ky.). Chymostatin, L-Try-Gly, puromycin, bestatin, EGTA, HEPES and BSA were purchased from Sigma Chemical Co. (St. Louis, Mo.). [$^{125}$I]BH-CCK$_8$ (specific activity, 2200 Ci/mmol) and Aquasol 2 scintillation cocktail were obtained from New England Nuclear (Boston, Ma.). Male guinea pigs, 250 to 325 g, were obtained from Scientific Small Animal Laboratory and Farm (Arlington Heights, Ill.). Collagenase, 300 units per mg, was purchased from Worthington (Frehold, N.J.)

Protocol For Radioligand Binding Experiments

1. Guinea Pig Cerebral Cortical and Pancreatic Membrane Preparations

Cortical and pancreatic membranes were prepared as described (Lin and Miller; J. Pharmacol. Exp. Ther. 232, 775–780, 1985). In brief, cortex and pancreas were removed and rinsed with ice cold saline. Visible fat and connective tissues were removed from the pancreas. Tissues were weighed and homogenized separately in approximately 25 mL of ice-cold 50 mM Tris-HCl buffer, pH 7.4 at 4° C., with a Brinkman Polytron for 30 sec, setting 7. The homogenates were centrifuged for 10 min at 1075 × g and pellets were discarded. The supernatants were saved and centrifuged at 38,730 × g for 20 min. The resultant pellets were rehomogenized in 25 mL of 50 mM Tris-HCl buffer with a Teflon-glass homogenizer, 5 up and down strokes. The homogenates were centrifuged again at 38,730 × g for 20 min. Pellets were then resuspended in 20 mM HEPES, containing 1 mM EGTA., 118 mM NaCl, 5 mM MgCl$_2$, 100 microM bestatin, 3 microM phosphoramidon, pH 7.4 at 22° C., with a Teflon-glass homogenizer, 15 up and down strokes. Resuspension volume for the cortex was 15–18 mL per gm of original wet weight and 60 mL per gm for the pancreas.

2. Incubation Conditions

[$^{125}$I]Bolton-Hunter CCK$_8$, and test compounds were diluted with HEPES-EGTA-salt buffer (see above) containing 0.5% bovine serum albumin (BSA). To 1 mL Skatron polystyrene tubes were added 25 microliters of test compounds, 25 miroliters of [$^{125}$I]BH-CCK$_8$, and 200 microliters of membrane suspension. The final BSA concentration was 0.1%. The cortical tissues were incubated at 30° C. for 150 min and pancreatic tissues were incubated at 37° C. for 30 min. Incubations were terminated by filtration using Skatron Cell Harvester and SS32 microfiber filter mats. The specific binding of [$^{125}$I]BH-CCK$_8$, defined as the difference between binding in the absence and presence of 1 microM CCK$_8$, was 85 90% of pancreas. IC$_{50}$'s were determined from the Hill analysis. The results of these binding assays are shown in Table I.

Protocol for Amylase

This assay was performed using the modified protocol of Lin et al., J. Pharmacol. Exp. Ther. 236, 734, 1986.

1. Guinea Pig Acini Preparation

Guinea pig acini were prepared by the method of Bruzzone et al. (Biochem. J. 226, 621–624, 1985) as follows. Pancreas was dissected out and connective tissues and blood vessels were removed. The pancreas was cut into small pieces (2mm) by a scissor and placed in a 15 mL conical plastic tube containing 2.5 mL of Krebs Ringer HEPES (KRH) buffer plus 400 units per mL of collagenase. The composition of the KRH buffer was: HEPES, 12.5 mM: NaCl, 118 mM; KCl, 4.8 mM; CaCl$_2$, 1 mM; KH 1.2 mM; MgSO$_4$, 1.2 mM; NaHCO$_3$, 5 mM; glucose, 10 mM, pH 7.4. The buffer was supplemented with MEM vitamins, 1% MEM amino acids and 0.001% aprotinin. The tube was shaken by hand until the suspension appeared homogeneous, usually 5 to 6 min. 5 mL of the KRH, without collagenase and with 0.1% BSA, were added and the tube was centrifuged at 50×g for 35 sec. The supernatant was discarded and 6 mL of the KRH were added to the cell pellet. Cells were triturated by a glass pipet and centrifuged at 50×g for 35 sec. This wash procedure was repeated once. The cell pellet from the last centrifugation step was then resuspended in 15 mL of KRH containing 0.1% BSA. The contents were filtered through a dual nylon mesh, size 275 and 75 micrometers. The filtrate, containing the acini, were centrifuged at 50× for 3 min. The acini were then resuspended in 5 mL of KRH-BSA buffer for 30 min at 37° C., under 100% O$_2$, with a change of fresh buffer at 15 min.

2. Amylase Assay

After the 30 min incubation time, the acini were resuspended in 100 volumes of KRH-BSA buffer, containing 3 microM phosphoramidon and 100 microM bestatin. While stirring, 400 microliters of acini were added to 1.5 mL microcentrifuge tubes containing 50 microliters of $CCK_8$, buffer, or test compounds. The final assay volume was 500 microliters. Tubes were vortexed and placed in a 37° C. water bath, under 100% $O_2$, for 30 min. Afterward, tubes were centrifuged at 10,000 g for 1 min. Amylase activity in the supernatant and the cell pellet were separately determined after appropriate dilutions in 0.1% Triton X-100, 10 mM NaH pH 7.4 by Abbott Amylase A-gent test using the Abbott Bichromatic Analyzer 200. The reference concentration for $CCK_8$ in determining the $IC_{50}$'s of the compounds of Formula I was $3 \times 10^{-10}M$. The results of this assay are shown in Table 2.

TABLE 1

| | $IC_{50}$ (nM) | |
|---|---|---|
| Compound of Example | $[^{125}I]$-BH-CCK Type-ACCK Receptor | $[^{125}I]$-BH-CCK Type-Bcck Receptor |
| 3 | 240 | 3500 |
| 4 | 20 | 1400 |
| 6 | 62 | 4200 |
| 8 | 200 | 19,000 |
| 10 | 34 | 6500 |
| 12 | 260 | 3200 |
| 13 | 92 | 5600 |
| 15 | 5.4 | 3500 |
| 18 | 820 | 2900 |
| 19 | 27 | 2600 |
| 21 | 210 | 6600 |
| 22 | 97 | 6660 |
| 23 | 98 | 3600 |
| 25 | 310 | >10,000 |
| 29 | 30 | 5100 |
| 34 | 30 | ~10,000 |
| 36 | 200 | 6300 |
| 37 | 49 | 1-10,000 |
| 38 | 900 | 7100 |
| 54 | 660 | >10,000 |
| 60 | 34 | 1-10,000 |
| 74 | 210 | 2000 |
| 82 | 250 | 10,000 |
| 83 | 44 | >10,000 |
| 84 | 28 | 620 |
| 85 | 100 | <10,000 |
| 89 | 140 | >10,000 |
| 91 | 68 | >10,000 |
| 93 | 100 | ≦10,000 |
| 106 | 93 | ~10,000 |
| 107 | 110 | >10,000 |
| 109 | 56 | 620 |

TABLE 2

| Compound of Example | $IC_{50}$ (nM) Inhibition of Amylase Release |
|---|---|
| 4 | 22 |
| 6 | 110 |
| 8 | 590 |
| 12 | 830 |
| 15 | 16 |
| 19 | 55 |
| 23 | 1300 |
| 29 | 130 |
| 34 | 53 |
| 74 | 1200 |

The results of the assays indicate that the compounds of the invention inhibit specific $[^{125}I]$—BH—CCK-8 receptor binding in the concentration range of $10^{-9}$ to $10^{-6}M$.

The ability of the compounds of Formula I to interact with CCK receptors and to antagonize CCK can be demonstrated in vivo using the following protocol.

Inhibition Of CCK Induced Gastric Emptying

Three fasted mice were dosed (p.o.) with the test compound. $CCK_8$ (80 micrograms/kg s.c.) was administered within 60 minutes and charcoal meal (0.1 mL of 10% suspension) was given orally 5 minutes later. The animals were sacrificed within an additional 5 minutes.

Gastric emptying, defined as the presence of charcoal within the intestine beyond the pyloric sphincter, is inhibited by $CCK_8$. Gastric emptying observed in more than 1 or 3 mice (greater than 1) indicates antagonism of $CCK_8$.

Gastric emptying was observed with a dose of 100 mg/kg of the compound of example 118 in three out of three mice.

The ability of the compounds of Formula I to antagonize CCK induced hyperinsulinemia can be demonstrated in vivo using the following protocol.

Measurement of Plasma Insulin Level Following Treatment with $CCK_8$ and a Compound of Formula I Male mice, 20-30 g, were used in all experiments. The animals were fed with laboratory lab chow and water ad libitum. The compound of Formula I (1 to 100 mg/kg in 0.2 mL of 0.9% saline) was administered i.p. Ten minutes later $CCK_8$ (0.2 to 200 nmole/kg in 0.2 mL of 0.9% saline) or saline was injected into the tail vein. Two minutes later the animals were sacrificed and blood was collected into 1.5 mL heparinized polypropylene tubes. The tubes were centrifuged at $10,000 \times g$ for 2 min. Insulin levels were determined in the supernatant (plasma) by an RIA method using kits from Radioassay Systems Laboratory (Carson, Ca.) or Novo Biolabs (Ma.).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil soluble or dispersible products are thereby obtained.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The pharmaceutically acceptable salts of the acid of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, trimethylamine, piperidine, pyrrolidine, benzylamine and the like, or a quaternary ammonium hydroxide such as tetramethylammonium hydroxide and the like.

When a compound of Formula I is used as an antagonist of CCK or gastrin in a human subject, the total daily dose administered in single or divided doses may be in amounts, for example, from 0.001 to 1000 mg a day and more usually 1 to 1000 mg. Dosage unit compositions may contain such amounts of submultiples thereof to make up the daily dose.

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, sex, diet, time of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsion, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula

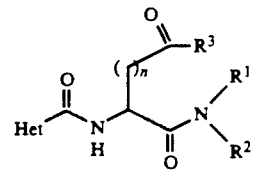

wherein
Het is a heterocyclic group selected from the group consisting of 2-indolyl, 3-indolyl, 5-fluoro-2-indolyl, 5-hydroxy-2-indoly, 2-quinolyl, 3-quinolyl, 6-quinolyl, 8-quinolyl, tetrahydro-3-quinolyl and tetrahydro-2-quinolyl;
n is 1, 2 or 3;
$R^1$ is —CH($R^5$)C(O)O$R^4$ wherein
(i) $C_1$-$C_8$-alkyl,
(ii) $C_2$-$C_8$-alkenyl,
(iii) cyclo-$C_3$-$C_8$-alkyl,
(iv) $C_2$-$C_8$-alkynyl,
(v) (CH$_2$)$_m$Ar, wherein m is 0, 1, 2, 3 or 4 and Ar is aryl, wherein aryl is a member selected from the group consisting of phenyl, naphthyl, 1,2,3,4-tetrahydronaphthyl, indanyl, indenyl, isoindenyl and fluorenyl, and
(vi) (CH$_2$)$_m$sAr wherein m is as defined above and sAr is a substituted aryl group, wherein the aryl group is substituted with one, two or three substituents selected from the group consisting of $C_1$-$C_8$-alkyl, $C_1$-$C_8$-alkoxy, thio-$C_1$-$C_8$-alkoxy, carboxy, carbo-$C_1$-$C_8$-alkoxy, nitro, trihalomethyl, hydroxy, amino and NH($C_1$-$C_8$-alkyl);
$R^5$ is selected from the group consisting of
(i) hydrogen,
(ii) Ar, as defined above,
(iii) sAr, as defined above,
(iv) $C_1$-$C_8$-alkyl,
(v) cyclo-$C_3$-$C_8$-alkyl, (vi) $(CH_2)_mAr$, wherein m and Ar are as defined above, (vii) $(CH_2)_m(sAr)$, wherein sAr and m are as defined above, and (viii) $(CH_2)_m$Hetcy, wherein m is as defined above and Hetcy is a member selected from the group consisting of
(a) 4-imidazolyl,
(b) 3-methyl-4-imidazole,
(c) 2-pyrazolyl,
(d) 4-oxazole,
(e) 4-thiazole,
(f) 3-indolyl,
(g) perhydroindanyl (Pic), and
(g) 1,2,3,4-tetrahydro-3-isoquinolyl (Tiq);

$R^2$ is selected from the group consisting of
(1) hydrogen
(2) $C_1$–$C_8$-alkenyl,
(3) $C_2$–$C_8$-alkenyl,
(4) cyclo-$C_3$–$C_8$-alkyl,
(5) adamantyl,
(6) Ar, as defined above,
(7) sAr, as defined above,
(8) Ar-$C_1$–$C_8$-alkyl, wherein Ar is as defined above,
(9) sAr-$C_1$–$C_8$-alkyl, wherein sAr is as define above,
(10) —$(CH_2)_p$-cyclo-$C_3$–$C_8$-alkyl, wherein p is 1, 2, 3 or 4,
(11) $CH(R^5)C(O)OR^4$, wherein $R^4$ and $R^5$ are as defined above,
(12) —$(CH_2)_m(C(O))_r$cyclo-$C_3$–$C_8$-alkyl wherein r is 0 or 1 and m is as defined above, provided that m is not 0 when r is 0,
(13) —$(CH_2)_m$CN, wherein m is as defined above,
(14) —$(CH_2)_m OR^6$, wherein m is as defined above and $R^6$ is selected from the group consisting of
(i) $C_1$–$C_8$-alkyl,
(ii) Ar, as defined above,
(iii) sAr, as defined above,
(iv) Ar-$C_1$–$C_8$-alkyl, wherein Ar is as defined above, and
(V) sAr-$C_1$–$C_8$-alkyl, wherein sAr is as defined above, and

(15) —$CH(R^5)C(O)NR^7R^8$, wherein $R^5$ is as defined above and $R^7$ and $R^8$ are independently selected from the group consisting of
(i) $C_1$–$C_8$-alkyl,
(ii) $C_2$–$C_8$-alkenyl,
(iii) cyclo-$C_3$–$C_8$-alkyl,
(iv) $C_2$–$C_8$-alkynyl,
(v) $(CH_2)_mAr$, wherein m and Ar are as defined above, and
(vi) $(CH_2)_m sAr$, wherein m and sAr are as defined above;

and $R^3$ is selected from the group consisting of
(1) —OH,
(2) —$OR^9$, wherein $R^9$ is selected from the group consisting of
(i) $C_1$–$C_8$-alkyl,
(ii) $C_2$–$C_8$-alkenyl,
(iii) cyclo-$C_3$–$C_8$-alkyl,
(iv) $C_2$–$C_8$-alkynyl,
(v) $(CH_2)_mAr$, wherein m and Ar are as defined above, and
(vi) $(CH_2)_m sAr$ wherein m and sAr are as defined above,
(3) —$NR^7R^8$, wherein $R^7$ and $R^8$ are as defined above, and
(4) tetrazolyl, 2. A compound according to claim 1, wherein Het is 2-indolyl, 3-indolyl, 5-fluoro, 2-indolyl or 5-hydroxy-2-indolyl, and n is 2.

3. A compound according to claim 1, wherein Het is 2-quinolyl, 3-quinolyl, 6-quinolyl, 8-quinolyl, tetrahydro-3-quinolyl or tetrahydro-2-quinolyl, and n is 2.

4. Methyl N-(2'-indolylcarbonyl)-R-glutamyl-S-α-phenylglycine; ethyl-(3'-quinolylcarbonyl)-R-glutamyl-(N-benzyl)glycinate; or methyl N-quinolylcarbonyl)-R-glutamyl-S-α-phenylglycine.

5. A pharmaceutical composition for blocking the physiological responses in the interaction of CCK with CCK Type-A receptors, comprising a pharmaceutically-acceptable carrier and a therapeutically-effective amount of a compound according to claim 1.

6. A pharmaceutical composition for the treatment or prevention of hyperinsulinemia or disorders of the gastrointestinal, central nervous, appetite regulating or pain regulating systems, comprising a pharmaceutically-acceptable carrier and a therapeutically-effective amount of a compound according to claim 1.

7. A method of blocking the effects of CCK comprising administering to a host in need of such treatment a therapeutically-effective amount of a compound according to claim 1.

8. A method of treating or preventing disorders of the gastrointestinal, central nervous, appetite regulating or pain regulating systems, comprising administering to a host in need of such treatment a therapeutically-effective amount of a compound according to claim 1.

9. A method of treating or preventing the hyperinsulinemia comprising administering to a host in need of such treatment a therapeutically-effective amount of a compound according to claim 1.

* * * * *

UNITED STATES PATENT AND TRADEMARK OFFICE
CERTIFICATE OF CORRECTION

PATENT NO. : 5,128,346

DATED : July 7, 1992

INVENTOR(S) : Alex M. Nadzan, James F. Kerwin, Chun W. Lin

It is certified that error appears in the above-indentified patent and that said Letters Patent is hereby corrected as shown below:

In column 1,   line 36, delete "CC", and insert --CCK--

In column 2,   line 40, delete "Ar" from the structure, and replace it with --Het--

In column 2,   line 63, delete "-$(CH_2)_m C(O))_4 NR_6 R_7$", and insert --$(CH_2)_m (C(O))_r NR_6 R_7$--

In column 3,   line 58, insert --$(C(O))_r (CH_2)_m R_6$, nitro, halogen--

In column 4,   line 3, delete "R", and insert --$R_6$--

In column 4,   line 39, insert --imidazolyl,-- between "pyrrolyl" and "pyrazolyl"

In column 4,   line 53, delete "amino", and insert --amino-$C_{1-4}$-alkyl,--

In column 5,   line 59, delete "pyrimidinyl", and insert --morpholinyl-- in column 5,   line 59, delete "oxadiazinyl", and insert --oxazinyl--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 7, line 68, delete "-(C(O))$_4$(CH$_2$)$_m$aryl,", and insert --(C(O))$_r$(CH$_2$)$_m$aryl--

In scheme 1, (columns 9-10), delete "H$_2$Pd/V P=Cbz" and insert --H$_2$Pd/C P=Cbz--

In column 14, line 49, delete "(4.9 g, 6.3 mmol)", and insert --(4.9g, 36.3 mmol)--

In column 14, line 65, delete "(d, 1H, J TM 12Hz", and insert --(d, 1H, J=12 Hz)--

In column 15, line 5, delete "N-(2,-Indolylcarbonyl)", and insert --N-(2'-Indolylcarbonyl)--

In column 15, line 30, delete "N-(2,-Quinolycarbonyl)", and insert --N-(2'-Quinolylcarbonyl)--

In column 15, line 59, delete "N-(2,-Quinolylcarbonyl", and insert --N-(2'-Quinolylcarbonyl)--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 17, line 2, delete "N-(2'-Quinoxalylcarbonyl)-r-benzyl", and insert --N-(2'-Quinoxalylcarbonyl)-γ-benzyl--

In column 17, line 18, delete "0.82-0 98(t,J=6Hz, 6H),", and insert --0.82-0.98(t,J=6H$_z$, 6H),--

In column 17, line 41, delete "443(m+)+", and insert --443(m+H)+ --

In column 17, line 65, delete "520(m+)+", and insert --520(m+H)+--

In column 20, line 7, insert --N-(2'-Indolylcarbonyl)-(β-benzyl ester)-R-Asp-di-n-pentylamide--

In column 21, line 51, delete "429(m+)+", and insert --429(m+H)+--

In column 21, line 59, delete "$C_{24}H_{36}N_4O_3$", and insert -- $C_{24}H_{36}N_4O_3$--

In column 22, line 5, delete "444(m+)+", and insert --444(m+H)+--

In column 22, line 29, delete "427(m+)+", and insert --427(m+H)+--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 23, line 37, insert --acetate and washed with three volumes of water, once with 1.0--, between "ethyl", and "N hydrochloric acid"

In column 23, line 45, delete "560(m+)+", and insert --560(m+H)+--

In column 23, line 57, insert --N-(2'-Indolylcarbonyl)-($\gamma$-benzyl ester)-R-Glu-dibenzylamide--

In column 24, line 4, delete "470(m+)+", and insert --470(m+H)+--

In column 24, lines 14 and 15, delete "R-Glutamic acid (692mg), EDCI (583", and insert -- -R-Glutamyl-R-phenylglycinate--

In column 24, line 29, delete "485(m+)+", and insert --485(m+H)+--

In column 24, line 61, delete "528(m+)+", and insert --528(m+H)+--

In column 25, line 30, delete "N-(6,-Quinolylcarbonyl)-", and insert --N-(6'-Quinolylcarbonyl)--

In column 26, line 2, delete "442(m+)+", and insert --442(m+H)+--

UNITED STATES PATENT AND TRADEMARK OFFICE
CERTIFICATE OF CORRECTION

PATENT NO. :  5,128,346  
DATED : July 7, 1992  
INVENTOR(S) : Alex M. Nadzan, James F. Kerwin, Chun W. Lin Page 5 of 10

It is certified that error appears in the above-indentified patent and that said Letters Patent is hereby corrected as shown below:

In column 27, line 8, delete "(m+)+", and insert --(m+H)+--

In column 27, line 20, delete "Boc(r-benzyl ester)", and insert --Boc(γ-benzyl ester)--

In column 27, line 60, delete "442(m+)+, and insert --442(m+H)+--

In column 28, line 49, delete "546(m+)+", and insert --546(m+H)+--

In column 29, line 5, delete "[δ]D=-24.4°", and insert [ ]$_D$=24.4°--.

In column 30, lines 27 and 40, delete "(3,-quinolyl)", and insert --(3'-quinolyl)--

In column 31, line 2, delete "(3,-quinolyl)", and insert --(3'-quinolyl)--

In column 31, line 46, delete "(1,-adamantyl)", and insert --(1'-adamantyl)--

In column 32, line 46, delete "(1,2'-diphenylethyl)", and insert --(1',2'-diphenylethyl)--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 33, lines 5 and 7, delete "(2,-Indolylcarbonyl)", and insert --(2'-Indolylcarbonyl)--

In column 33, line 11, insert after "ambient temperature", --was treated with 1 N NaOH(560 µL, 0.56 mmol). After three hours, the solvent--

In column 33, line 60, delete "2,-Indolylcarbonyl)", and insert --2'-Indolylcarbonyl)--

In column 36, line 14, delete "$C_{29}H_{25}N_5O_4$", and insert --$C_{29}H_{25}N_5O_4$--

In column 40, line 38, delete "$C_{33}H_{33}N_3O_6$", and insert --$C_{33}H_{33}N_3O_6$--

In column 41, line 14, delete "7.20-7.45(m,1H)", and insert --7.20-7.45(m,11H)--

In column 42, line 24, delete "$C_{32}H_{30}N_2O_6$", and insert --$C_{32}H_{30}N_2O_6$:--.

In column 43, line 29, delete "$C_{31}H_{29}N_3O_8O.5$", and insert --$C_{31}H_{29}N_3O_8\ 0.5$--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 43, line 67, delete "$C_{24}H_{36}N_2O_7$", and insert --$C_{24}H_{36}N_2O_7$:--.

In column 44, line 34, delete "$C_{30}H_{34}N_2O_6$", and insert --$C_{30}H_{34}N_2O_6$--

In column 44, line 56, delete "$C_{23}H_{28}N_2O_6$", and insert --$C_{23}H_{28}N_2O_6$--

In column 45, line 3, delete ",3H),", and insert --1.55-1.71(m,3H)--

In column 47, line 3, delete "$C_{31}H_{34}N_2O_8$ 0 3", and insert --$C_{31}H_{34}N_2O_8$ 0.3--

In column 47, line 49, delete "$C_{30}H_{33}N_3O_8$", and insert --$C_{30}H_{33}N_3O_8$--

In column 47, line 60, delete "$[\alpha]_D=+17°$", and insert --$[\alpha]_D=+17.1°$--

In column 47, line 62, delete "(DMSO,300MHz)", and insert --(DMSO$_{d6}$,300MHz),--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 48, line 2, delete "$C_{23}H_{27}N_3O_8$" and insert --$C_{23}H_{27}N_3O_8$--

In column 48, line 6, delete "N-(4,8-", and insert --N-(4',8'--

In column 48, line 33, delete "$C_{30}H_{33}N_3O_{10}$," and insert --$C_{30}H_{33}N_3O_{10}$--

In column 48, line 54, delete "$C_{23}H_{27}N_3O_{10}$", and insert --$C_{23}H_{27}N_3O_{10}$--

In column 49, line 12, delete "$C_{29}H_{46}N_4O_3$", and insert --$C_{29}H_{46}N_4O_3$:--.

In column 49, line 29, delete "$C_{32}H_{44}N_4O_3$", and insert --$C_{32}H_{44}N_4O_3$--

In column 50, line 16, delete "-R-Glu-N-", and insert "-R-Glu-N*"

In column 51, line 58, delete "membrances", and insert --membranes--

In column 52, line 6, after "mM NaCl,", insert --4.7 mM KCl,--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, James F. Kerwin, Chun W. Lin It is certified that error appears in the above-indentified patent and that said Letters Patent is hereby corrected as shown below:

In column 52, line 29, delete "85 90% of", and insert --85-90% of total binding in cortex and 90-95% in--

In column 52, line 35, delete "236,734,", and insert --236,729-734,--

In column 52, line 49, delete "KH 1.2 mM;", and insert --$KH_2PO_4$, 1.2 mM;--

In column 52, line 51, delete "with MEM", and insert --with 1% MEM--

In column 52, line 66, delete "50x for 3", and insert --50xg for 3--

In column 53, line 15, delete "NaH pH", and insert --$NaH_2PO_4$, pH--

In column 56, line 46, after "-$CH(R^5)C(O)OR^4$ wherein", and insert --$R^4$ is selected from the group consisting of--

In column 58, line 20, delete "(2)$C_1$-$C_8$-alkenyl," and insert --(2)$C_1$-$C_8$-alkyl,--

UNITED STATES PATENT AND TRADEMARK OFFICE
CERTIFICATE OF CORRECTION

PATENT NO. : 5,128,346
DATED : July 7, 1992
INVENTOR(S) : Alex M. Nadzan, et al

It is certified that error appears in the above-indentified patent and that said Letters Patent is hereby corrected as shown below:

In column 58, line 32, delete "in", and insert --to--

Signed and Sealed this

Twenty-seventh Day of September, 1994

Attest:

BRUCE LEHMAN

Attesting Officer    Commissioner of Patents and Trademarks